US009599626B2

(12) United States Patent
Desai

(10) Patent No.: US 9,599,626 B2
(45) Date of Patent: Mar. 21, 2017

(54) THERAPEUTIC AND DIAGNOSTIC METHOD FOR ATAXIA-TELANGIECTASIA

(71) Applicant: Shyamal D. Desai, Metairie, LA (US)

(72) Inventor: Shyamal D. Desai, Metairie, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/688,384

(22) Filed: Nov. 29, 2012

(65) Prior Publication Data

US 2014/0148496 A1   May 29, 2014
US 2016/0216279 A9   Jul. 28, 2016

Related U.S. Application Data

(60) Provisional application No. 61/565,715, filed on Dec. 1, 2011, provisional application No. 61/706,863, filed on Sep. 28, 2012.

(51) Int. Cl.

| C12N 15/11 | (2006.01) |
|---|---|
| G01N 33/68 | (2006.01) |
| A61K 31/713 | (2006.01) |
| A61K 31/52 | (2006.01) |

(52) U.S. Cl.
CPC ......... *G01N 33/6896* (2013.01); *A61K 31/52* (2013.01); *A61K 31/713* (2013.01); *G01N 2500/00* (2013.01); *G01N 2800/2835* (2013.01)

(58) Field of Classification Search
None
See application file for complete search history.

(56) References Cited

U.S. PATENT DOCUMENTS

| 2004/0185558 A1* | 9/2004 | Griguer ............... C12N 5/0062 435/368 |
| 2005/0019847 A1 | 1/2005 | Zhang et al. ................ 435/7.93 |
| 2008/0261226 A1 | 10/2008 | Wang et al. ..................... 435/6 |
| 2008/0317834 A1* | 12/2008 | Green et al. .................. 424/450 |
| 2010/0111874 A1 | 5/2010 | Liu et al. ....................... 424/9.2 |

OTHER PUBLICATIONS

Chen et al, ISG15, a ubiquitin-like interferon-stimulated gene, promotes hepatitis C virus production in vitro: implications for chronic infection and response to treatment, 2010, Journal of General Virology, 91: 382-388.*
WO 2005/116204, Dec. 2005. Because of the extreme length of document only front page and translation of relevant portion of a document (search result) are provided. 2 pages.*
Mu et al, A Proteomic Analysis of Ataxia Telangiectasia-mutated (ATM)/ATM-Rad3-related (ATR) Substrates Identifies the Ubiquitin-Proteasome System as a Regulator for DNA Damage Checkpoints, 2007, Journal of Biological Chemistry, vol. 282, 24: 17330-17334.*
Ritchie et al, Role of ISG15 protease UBP43 (USP18) in innate immunity to viral infection, 2004, Nature Medicine, vol. 10, 12: 1374-1378.*
Agamanolis, D. P. et al., "Ataxia-telangiectasia. Report of a case with Lewy bodies and vascular abnormalities within cerebral tissue," J. Neuropathol. Exp. Neurol. 38, 475-489 (1979).
Ambrose, M. et al., "Intrinsic mitochondrial dysfunction in ATM-deficient lymphoblastoid cells," Hum Mol Genet,, vol. 16, pp. 2154-2164 (2007).
Barlow, C. et al., "ATM is a cytoplasmic protein in mouse brain required to prevent lysosomal accumulation," Proc. Natl, Acad. Sci. U S A, vol. 97, pp. 871-876 (2000).
Biton, S. et al., "The neurological phenotype of ataxia-telangiectasia: solving a persistent puzzle," DNA Repair (Amst), vol. 7, pp. 1028-1038 (2008).
Boder, E., "Ataxia-telangiectasia: an overview," Kroc Found. Ser. vol. 19, pp. 1-63 (1985).
Bregman, D. B. et al., "UV-induced ubiquitination of RNA polymerase II: a novel modification deficient in Cockayne syndrome cells," Proc. Natl. Acad. Sci. U S A vol. 93, pp. 11586-11590 (1996).
Browne, S. E. et al., "Oxidative damage and mitochondrial dysfunction in neurodegenerative diseases," Biochem Soc Trans, vol. 22: pp. 1002-1006 (1994).
Cherra, S. J. et al., "Autophagy in neuroprotection and neurodegeneration: A question of balance," Future Neurol., vol. 3, pp. 309-323 (2008).
Chu, C. T., "Autophagic stress in neuronal injury and disease," J. Neuropathol. Exp. Neurol., vol. 65, pp. 423-432 (2006).
Chun, H. H. et al., "Ataxia-telangiectasia, an evolving phenotype," DNA Repair (Amst), vol. 3, pp. 1187-1196 (2004).
Ciechanover, A.,"Early work on the ubiquitin proteasome system, an interview with Aaron Ciechanover. Interview by CDD," Cell Death Differ, vol. 12, pp. 1167-1177 (2005).
Desai, S. D. et al., "Elevated expression of ISG15 in tumor cells interferes with the ubiquitin/26S proteasome pathway," Cancer Res., vol. 66, pp. 921-928 (2006).

(Continued)

*Primary Examiner* — Kate Poliakova-Georgantas
(74) *Attorney, Agent, or Firm* — John H. Runnels; Jeanne Davis

(57) ABSTRACT

ATM kinase is shown to regulate proteasome-mediated protein turnover through suppression of the expression of the ubiquitin-like protein ISG15 (Interferon Stimulated Gene 15). Silencing of the ISG15 pathway restored both the ubiquitin and autophagy pathways, and the UV-mediated degradation of their substrates in A-T cells. The ATM kinase negatively regulates the ISG15 pathway, and the constitutively elevated ISG15 pathway induces proteinopathy in A-T cells, and in A-T patients. These findings indicate that proteasome-mediated protein degradation is impaired in A-T cells due to elevated expression of the ISG15 conjugation pathway, which contributes to progressive neurodegeneration in A-T patients. The ISG15 pathway is a new target for both detection and treatment of A-T Inhibitors if ISG15 expression can be used to inhibit or attenuate neurodegeneration in A-T patients. In addition, an inhibitor of the early phase of autophagy, 3-MA, was shown to be effective in decreasing the impaired proteasome-mediated protein degradation in A-T cells, and thus would be effective in decreasing the neurodegeneration in A-T patients.

5 Claims, 31 Drawing Sheets

(56) References Cited

OTHER PUBLICATIONS

Desai, S. D. et al., "Ubiquitin/26S proteasome-mediated degradation of topoisomerase I as a resistance mechanism to camptothecin in tumor cells," Cancer Res., vol. 61, pp. 5926-5932 (2001).
Desai, S. D. et al., "Ubiquitin-dependent destruction of topoisomerase I is stimulated by the antitumor drug camptothecin," J. Biol. Chem., vol. 272, pp. 24159-24164 (1997).
Desai, S. D. et al., "ISG15 disrupts cytoskeletal architecture and promotes motility in human breast cancer cells," Exp. Biol. Med. (Maywood), vol. 237, pp. 38-49 (2012).
Desai, S. D. et al., "ISG15 as a novel tumor biomarker for drug sensitivity," Mol. Cancer Ther., vol. 7, pp. 1430-1439 (2008).
Desai, S. D. et al., "Transcription-dependent degradation of topoisomerase I-DNA covalent complexes," Mol. Cell Biol., vol. 23, pp. 2341-2350 (2003).
Desai, S.D. et al., "Rethinking neurodegeneration in Ataxia Telangiectasia: Role of proteinopathy," an abstract submitted for the 14th International Workshop on Ataxia-Telangiectasia and ATM (Feb. 7-11, 2012).
Easton, D. F., "Cancer risks in A-T heterozygotes," Int. J. Radiat. Biol., vol. 66, pp. S177-A182 (1994).
Eilam, R. et al., "Late degeneration of nigro-striatal neurons in ATM-/- mice," Neuroscience 121, 83-98 (2003).
Figueiredo-Pereira, M. E. et al., "The ubiquitin/proteasome pathway: friend or foe in zinc-, cadmium-, and H2O2-induced neuronal oxidative stress," Mol. Biol. Rep., vol. 26, pp. 65-69 (1999).
Frappart, P. O. et al., "Ataxia-telangiectasia and related diseases," Neuromolecular Med., vol. 8, pp. 495-511 (2006).
Ge, P. F. et al., "Inhibition of autophagy induced by proteasome inhibition increases cell death in human SHG-44 glioma cells," Acta Pharmacol. Sin., vol. 30, pp. 1046-1052 (2009).
Haas, A. L. et al., "Interferon induces a 15-kilodalton protein exhibiting marked homology to ubiquitin," J. Biol. Chem., vol. 262, pp. 11315-11323 (1987).
Herzog, K.H. et al., "Requirement for Atm in ionizing radiation-induced cell death in the developing central nervous system," Science, vol. 280: pp. 1089-1091 (1998).
Ikeda, F. et al., "Atypical ubiquitin chains: new molecular signals. 'Protein Modifications: Beyond the Usual Suspects' review series," EMBO Rep, vol. 9: pp. 536-542 (2008).
Johri, A. et al., "Mitochondrial dysfunction in neurodegenerative diseases," J Pharmacol Exp Ther, vol. 342 pp. 619-630 (2012).
Kabeya, Y et al., LC3, a mammalian homologue of yeast Apg8p, is localized in autophagosome membranes after processing. EMBO J., vol. 19, pp. 5720-5728 (2000).
Katyal, S. et al., "DNA strand breaks, neurodegeneration and aging in the brain," Mech. Ageing Dev., vol. 129, pp. 483-491 (2008).
Klionsky, D. J. et al., "Autophagy as a regulated pathway of cellular degradation," Science, vol. 290, pp. 1717-1721 (2000).
Klionsky, D. J. et al., "Guidelines for the use and interpretation of assays for monitoring autophagy in higher eukaryotes," Autophagy, vol. 4, pp. 151-175 (2008).
Komatsu, M. et al., "Physiological significance of selective degradation of p62 by autophagy," FEBS Lett., vol. 584, pp. 1374-1378 (2010).
Lavin, M. F. et al., "ATM: the protein encoded by the gene mutated in the radiosensitive syndrome ataxia-telangiectasia," Int. J. Radiat. Biol., vol. 75, pp. 1201-1214 (1999).
Lavin, M. F. et al., ATM signaling and genomic stability in response to DNA damage. Mutat. Res., vol. 569, pp. 123-132 (2005).
Lavin, M. F. et al., "Functional consequences of sequence alterations in the ATM gene," DNA Repair (Amst), vol. 3, pp. 1197-1205 (2004).
Lehman, N. L., "The ubiquitin proteasome system in neuropathology," Acta Neuropathol., vol. 118, pp. 329-347 (2009).
Lin, M. T. et al., "Mitochondrial dysfunction and oxidative stress in neurodegenerative diseases," Nature, vol. 443 pp. 787-795 (2006).
Liu, L. F., DNA topoisomerase poisons as antitumor drugs. Annu. Rev. Biochem., vol. 58, pp. 351-375 (1989).

Loeb, K. R. et al., "The interferon-inducible 15-kDa ubiquitin homolog conjugates to intracellular proteins," J. Biol. Chem., vol. 267, pp. 7806-7813 (1992).
Lu, F. et al., "ISG15 enhances the innate antiviral response by inhibition of IRF-3 degradation," Cell Mol Biol (Noisy-le-grand), vol. 52, pp. 29-41 (2006).
Malakhova, O. A. et al., "ISG15 inhibits Nedd4 ubiquitin E3 activity and enhances the innate antiviral response," J. Biol. Chem., vol. 283, pp. 8783-8787 (2008).
Maragakis, N. J. et al., "Mechanisms of Disease: astrocytes in neurodegenerative disease," Nat. Clin. Pract. Neurol., vol. 2, pp. 679-689 (2006).
Matsuoka, S. et al., "ATM and ATR substrate analysis reveals extensive protein networks responsive to DNA damage," Science, vol. 316, pp. 1160-1166 plus online supporting material (2007).
Menendez-Benito V. et al., Endoplasmic reticulum stress compromises the ubiquitin-proteasome system. Hum Mol Genet, vol. 14, pp. 2787-2799 (2005).
Metcalf, D. J. et al., "Autophagy and misfolded proteins in neurodegeneration," Exp Neurol., vol. 238, pp. 22-28 (2012).
Mizushima, N.,"Autophagy: process and function," Genes Dev., vol. 21, pp. 2861-2873 (2007).
Narasimhan, J. et al., "Conjugation of the 15-kDa interferon-induced ubiquitin homolog is distinct from that of ubiquitin," J. Biol. Chem., vol. 271, pp. 324-330 (1996).
Nedelsky, N. B. et al., "Autophagy and the ubiquitin-proteasome system: collaborators in neuroprotection," Biochim. Biophys. Acta., vol. 1782, pp. 691-699 (2008).
Okumura, A. et al., "Innate antiviral response targets HIV-1 release by the induction of ubiquitin-like protein ISG15," Proc Natl Acad Sci U S A, vol. 103, pp. 1440-1445 (2006).
Okumura, A. et al., "ISG15 inhibits Ebola VP40 VLP budding in an L-domain-dependent manner by blocking Nedd4 ligase activity," Proc. Natl. Acad. Sci. U S A, vol. 105, pp. 3974-3979 (2008).
Pandey, U. B. et al., "HDAC6 at the intersection of autophagy, the ubiquitin-proteasome system and neurodegeneration," Autophagy, vol. 3, pp. 643-645 (2007).
Pandey, U. B. et al., "HDAC6 rescues neurodegeneration and provides an essential link between autophagy and the UPS," Nature, vol. 447, pp. 859-863 (2007).
Pear, W. S. et al., "Production of high-titer helper-free retroviruses by transient transfection," Proc. Natl. Acad. Sci. U S A, vol. 90, pp. 8392-8396 (1993).
Rolig, R. L. et al., "Linking DNA damage and neurodegeneration," Trends Neurosci., vol. 23, pp. 417-424 (2000).
Ross, C. A. et al., "The ubiquitin-proteasome pathway in Parkinson's disease and other neurodegenerative diseases," Trends Cell Biol., vol. 14, pp. 703-711 (2004).
Rubinsztein, D. C., "Autophagy induction rescues toxicity mediated by proteasome inhibition," Neuron, vol. 54, pp. 854-856 (2007).
Sakaguchi, A. et al., "Functional compatibility between isoform alpha and beta of type II DNA topoisomerase," J Cell Sci, vol. 117, pp. 1047-1054 (2004).
Savitsky, K. et al., "A single ataxia telangiectasia gene with a product similar to PI-3 kinase," Science, vol. 268, pp. 1749-1753 (1995).
Schmitt, H. P., "Protein ubiquitination, degradation and the proteasome in neuro-degenerative disorders: no clear evidence for a significant pathogenetic role of proteasome failure in Alzheimer disease and related disorders," Med. Hypotheses, vol. 67, pp. 311-317 (2006).
Seglen, P. O. et al., "3-Methyladenine: specific inhibitor of autophagic/lysosomal protein degradation in isolated rat hepatocytes," Proc. Natl. Acad. Sci. U S A, vol. 79, pp. 1889-1892 (1982).
Sharma, A. et al., "Ultraviolet radiation stress triggers the down-regulation of essential replication factor Mcm10," J. Biol. Chem., vol. 285, pp. 8352-8362 (2010).
Shiloh, Y. et al., "Ataxia-telangiectasia and the ATM gene: linking neurodegeneration, immunodeficiency, and cancer to cell cycle checkpoints," J. Clin. Immunol., vol. 16, pp. 254-260 (1996).

(56) References Cited

OTHER PUBLICATIONS

Siddoo-Atwal, C. et al., "Elevation of interferon beta-inducible proteins in ataxia telangiectasia cells," Cancer Res., vol. 56: pp. 443-447 (1996).
Sun, X. et al., "Early diagnosis of ataxia-telangiectasia using radiosensitivity testing," J. Pediatr., vol. 140, pp. 724-731 (2002).
Takeuchi, T. et al., "ISG15 modification of Ubc13 suppresses its ubiquitin-conjugating activity," Biochem. Biophys. Res. Commun., vol. 336, pp. 9-13 (2005).
Takeuchi, T. et al., "Link between the Ubiquitin Conjugation System and the ISG15 Conjugation System: ISG15 Conjugation to the UbcH6 Ubiquitin E2 Enzyme," J Biochem (Tokyo), vol. 138, pp. 711-719 (2005).
Tanida, I. et al., "LC3 conjugation system in mammalian autophagy," Int. J. Biochem. Cell Biol., vol. 36, pp. 2503-2518 (2004).
Taylor, A. M. et al., "Ataxia telangiectasia: a human mutation with abnormal radiation sensitivity," Nature, vol. 258, pp. 427-429 (1975).
Thomson, T. M. et al., "Ubiquitin and SUMO signaling in DNA repair," Biochem. Soc. Trans., vol. 38, pp. 116-131 (2010).
Valentin-Vega, Y. A. et al., "Mitochondrial dysfunction in ataxia-telangiectasia," Blood, vol. 119, pp. 1490-1500 (2012).
Wang, R. et al., "Activation of interferon signaling pathways in spinal cord astrocytes from an ALS mouse model," Glia, vol. 59, pp. 946-958 (2011).
Wood, L.M. et al., "A novel role for ATM in regulating proteasome-mediated protein degradation through suppression of the ISG15 conjugation pathway," PLoS ONE, vol. 6, No. 1, pp. 1-12 (published Jan. 26, 2011).
Wu, X. et al., "ATM phosphorylation of Nijmegen breakage syndrome protein is required in a DNA damage response," Nature, vol. 405, pp. 477-482 (2000).
Wu, W. K., et al., "Induction of autophagy by proteasome inhibitor is associated with proliferative arrest in colon cancer cells," Biochem. Biophys. Res. Commun., vol. 374, pp. 258-263 (2008).
Wu, X. et al., Interactions of the Nijmegen breakage syndrome protein with ATM and BRCA1. Cold Spring Herb. Symp. Quant. Biol., vol. 65, pp. 535-545 (2000).
Yamamoto, A. et al., "Bafilomycin A1 prevents maturation of autophagic vacuoles by inhibiting fusion between autophagosomes and lysosomes in rat hepatoma cell line, H-4-II-E cells," Cell Struct. Funct., vol. 23, pp. 33-42 (1998).
Zhang, D. et al., Interferon-stimulated gene 15 and the protein ISGylation system. J Interferon Cytokine Res., vol. 31, pp. 119-130 (2011).
Zou, W. et al., "ISG15 modification of ubiquitin E2 Ubc13 disrupts its ability to form thioester bond with ubiquitin," Biochem. Biophys. Res. Commun., vol. 336, pp. 61-68 (2005).
Zou, W. et al., "Negative regulation of ISG15 E3 ligase EFP through its autoISGylation," Biochem. Biophys. Res. Commun., vol. 354, pp. 321-327 (2007).

* cited by examiner

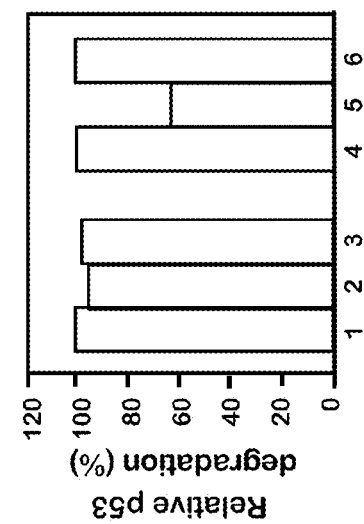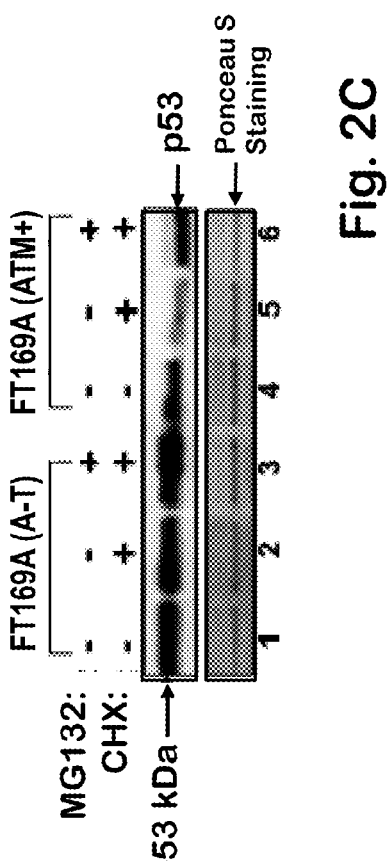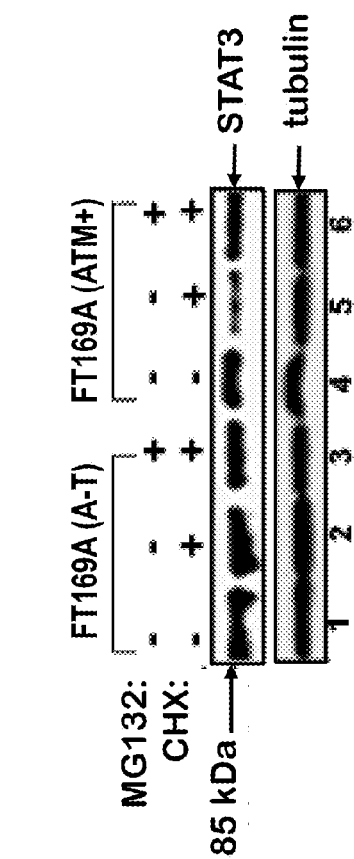
Fig. 2C
Fig. 2D

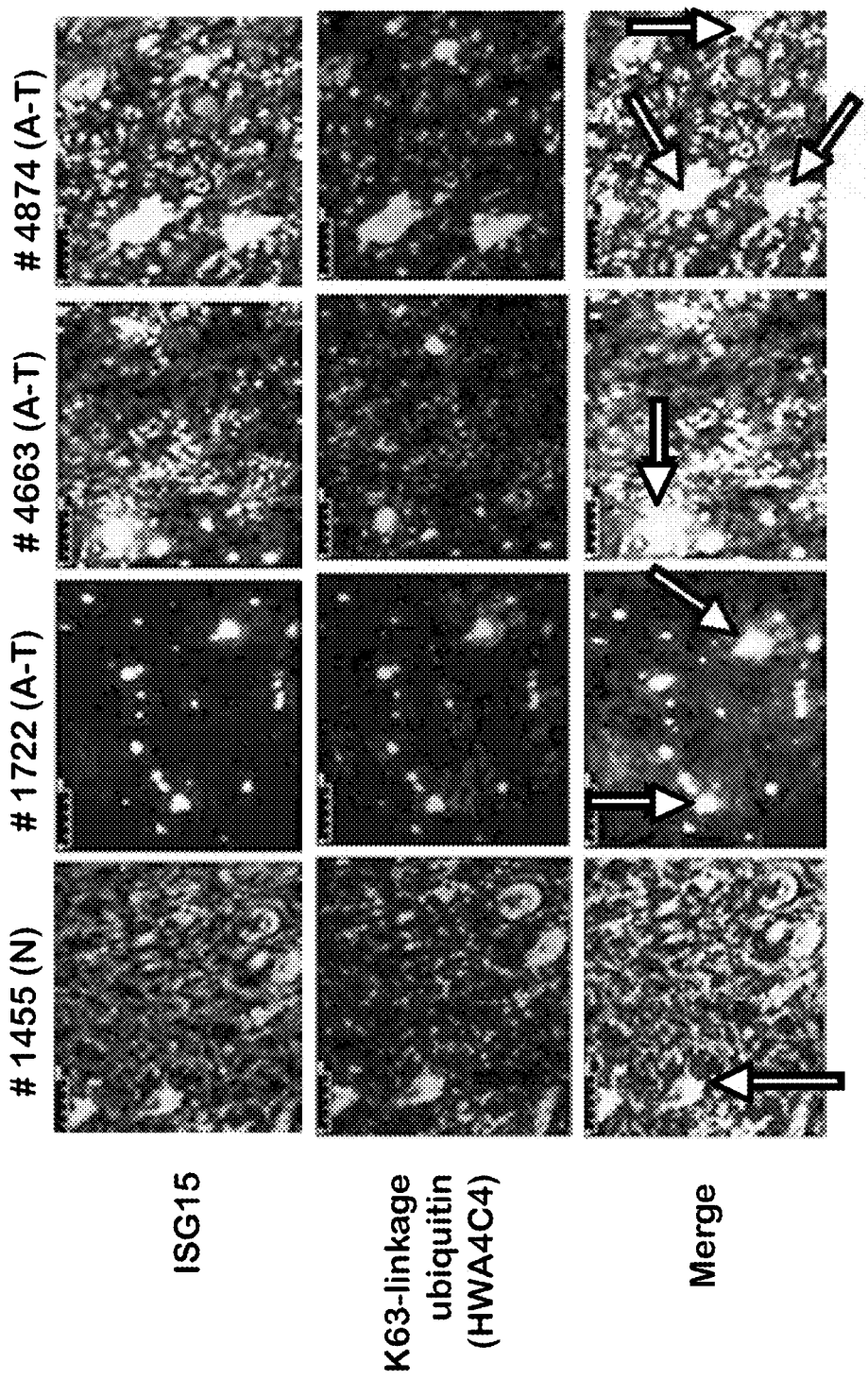

SEQUENCE LISTING

<160> NUMBER OF SEQ ID NOS: 3

<210> SEQ ID NO 1
<211> LENGTH: 498
<212> TYPE: DNA

<213> ORGANISM: Homo sapiens
<300> PUBLICATION INFORMATION:
<308> DATABASE ACCESSION NUMBER: Genbank AY168648
<309> DATABASE ENTRY DATE: 2002-12-22
<313> RELEVANT RESIDUES IN SEQ ID NO: (1)..(498)

<400> SEQUENCE: 1

```
atgggctggg acctgacggt gaagatgctg gcgggcaacg aattccaggt gtccctgagc    60
agctccatgt cggtgtcaga gctgaaggcg cagatcaccc agaagatcgg cgtgcacgcc   120
ttccagcagc gtctggctgt ccacccgagc ggtgtggcgc tgcaggacag ggtcccccctt  180
gccagccagg gctgggccc cggcagcacg gtcctgctgg tggtggacaa atgcgacgaa   240
cctctgaaca tcctggtgag gaataacaag ggccgcagca gcacctacga ggtgcggctg   300
acgcagaccg tggcccacct gaagcagcaa gtgagcgggc tggagggtgt gcaggacgac   360
ctgttctggc tgaccttcga ggggaagccc ctggaggacc agctcccgct gggggagtac   420
ggcctcaagc ccctgagcac cgtgttcatg aatctgcgcc tgcggggagg cggcacagag   480
cctggcgggc ggagctaa                                                 498
```

<210> SEQ ID NO 2
<211> LENGTH: 459
<212> TYPE: DNA
<213> ORGANISM: Homo sapiens
<300> PUBLICATION INFORMATION:
<308> DATABASE ACCESSION NUMBER: Genbank AF031141
<309> DATABASE ENTRY DATE: 1997-11-16
<313> RELEVANT RESIDUES IN SEQ ID NO: (1)..(459)

<400> SEQUENCE: 2

```
atggcgagca tgcgagtggt gaaggagctg gaggatcttc agaagaagcc tcccccatac    60
ctgcggaacc tgtccagcga tgatgccaat gtcctggtgt ggcacgctct cctcctaccc   120
gaccaacctc cctaccacct gaaagccttc aacctgcgca tcagcttccc gccggagtat   180
ccgttcaagc ctcccatgat caaattcaca accaagatct accacccaa cgtgacgag    240
aacggacaga tttgcctgcc catcatcagc agtgagaact ggaagccttg caccaagact   300
tgccaagtcc tggaggccct caatgtgctg gtgaatagac cgaatatcag ggagcccctg   360
cggatggacc tcgctgacct gctgacacag aatccggagc tgttcagaaa gaatgccgaa   420
gagttcaccc tccgattcgg agtggaccgg ccctcctaa                          459
```

<210> SEQ ID NO 3
<211> LENGTH: 12979
<212> TYPE: DNA
<213> ORGANISM: Homo sapiens
<220> FEATURE:
<221> NAME/KEY: misc_feature
<222> LOCATION: (5427)..(5427)
<223> OTHER INFORMATION: n is a, c, g, or t
<220> FEATURE:
<221> NAME/KEY: misc_feature
<222> LOCATION: (5460)..(5461)
<223> OTHER INFORMATION: n is a, c, g, or t
<220> FEATURE:
<221> NAME/KEY: misc_feature
<222> LOCATION: (12190)..(12190)
<223> OTHER INFORMATION: n is a, c, g, or t
<220> FEATURE:
<221> NAME/KEY: misc_feature
<222> LOCATION: (12192)..(12192)
<223> OTHER INFORMATION: n is a, c, g, or t
<220> FEATURE:
<221> NAME/KEY: misc_feature
<222> LOCATION: (12237)..(12240)
<223> OTHER INFORMATION: n is a, c, g, or t <300> PUBLICATION INFORMATION:
<308> DATABASE ACCESSION NUMBER: Genbank AF294032
<309> DATABASE ENTRY DATE: 2001-01-17
<313> RELEVANT RESIDUES IN SEQ ID NO: (1)..(12979)

<400> SEQUENCE: 3

| | | | | | |
|---|---|---|---|---|---|
| gaattccttg | agcccaggaa | gctgcagtga | gccacgtttg | taccattgca | ctccagcttg | 60 |
| ggagatagag | tgagaccctg | tctcaaaaaa | aaaaaaaaa | aaaaaaagaa | aaatttattt | 120 |
| ggcttacaga | tgtctgggct | gtacaagaag | tgtggcagca | gcatctgctt | ccagtgaagg | 180 |
| cattaggctc | cttctactca | gcagaagaca | acatgcagct | ggcatgtgca | gagaccacat | 240 |
| ggtaagagaa | gaagccaatg | ggggaatgca | atgggggggac | ggggagacac | acactttttt | 300 |
| tttttttttt | gagatggagt | ctcgctctgt | cacccaggct | ggagtgcagt | ggcgcgatct | 360 |
| cggctcactg | caagctctgc | ctcccgggtt | cacgccattc | tcctgcctca | gccgcccgag | 420 |
| tagctgggac | tacaggtgcc | caccaccacg | cccgctgat | ttttttgtatt | tttagtagag | 480 |
| atggggtttc | accatgttag | ccaggatggt | ctcgatctcc | tgacctcgtg | atctgcctgc | 540 |
| cttggcttcc | caaagtgctg | ggattacagg | catgagccac | catgcctgtc | cctttttttt | 600 |
| tttttttttt | tgagacaggg | gctgtcaccc | aggctggagt | gcactggcgt | ggtcatggct | 660 |
| cattgcacct | ttcacctcag | gctcaagaga | ccctcctacc | tcagcctcct | cagtagctgg | 720 |
| gactaaggaa | gtacaccacc | atgcccagct | aattatttttt | tttaagatgc | aatctcactc | 780 |
| tgttgcccag | gctgcactgc | agtggtacaa | tctcagctca | ctgcaacctc | cgcctcctgg | 840 |
| gttcaagcga | ttctcttgct | tcagcctcct | gagtagctgg | gattacagat | gcctgccacc | 900 |
| aggcccggct | aattttttgta | ttttttagtag | atacagggtt | tcgccatgtt | ggccaggctg | 960 |
| gtctcgaact | cctaacctaa | ggtgatccgc | ccatctcggc | ctcccaaagt | gctgggatta | 1020 |
| caggcatgag | ccaccgtgcc | tggcccatgc | ccagctaagt | taaaaaaatt | tttggctggg | 1080 |
| caaggtgatt | catacctgta | attccaacaa | tttgggaagc | taaggcaggc | agatcccatt | 1140 |
| tgagctcagg | aattggagac | catcttggac | aatatggcga | atcctgtct | ctacaaaata | 1200 |
| tacaaaaatt | agctgggtgt | ggtggcgctg | tgcctgtagt | cccagctact | ccagaggctg | 1260 |
| aggtgggagg | atggcttgag | cccgggaggc | agaggttgca | gtgagccaaa | atggtgacat | 1320 |
| tgcactccag | cctgggcaac | agagccagac | cctgtctcaa | aaaaaaaaa | aaaaagctct | 1380 |
| aaaaatagat | agtggtgata | gttagttaca | caacattgtg | aatgtactta | aatgtcactg | 1440 |
| aattatacac | ttaaatgttt | aaatggtaaa | ttctatctta | tgtatatttt | accacaattt | 1500 |
| aaaaattta | tctatttcta | ttttaatgag | agttttaaaa | agcaggaatg | gatattgaat | 1560 |
| ttccttaaat | actctttgga | gtctattaaa | gatagcattt | tacttcaaaa | tccagccctg | 1620 |
| gtttctgtac | ctagtacttc | tgtcacacca | gtaaatgtta | ttgaatgaaa | acaaacaaaa | 1680 |
| gaccataaag | acatacctct | tcacgttcac | taggattggt | gtcattttt | taaaaaaagg | 1740 |
| aaagaaaaat | aaccagtatt | ggcaacagtg | tggatatata | gaattttttg | tatattgctg | 1800 |
| gtaggaatat | aaaatagga | aaacggtttg | gtggttcctc | aaaaagttca | acataaaccc | 1860 |
| aggcgcggtg | gctcatgcct | gtaatcctag | cactttggga | ggctgaggtg | ggagaactgt | 1920 |
| ttgatcccag | gagtttgaga | ccagcctagg | caatatggtg | agacctcatc | tctacaaaaa | 1980 |
| attagctagg | catggtggcg | catgcctgta | gtcccagcta | cctgggaggc | taagacagaa | 2040 |
| agatcacttg | agcctggaag | ggagtttgag | gctgcagtga | gcccagattg | cgccactgca | 2100 |
| ctccagcctg | ggtgacagag | tgatatcctg | tctcaaaata | aataaataaa | taataaacaa | 2160 |

```
acacagaatt accatatgac ccagcaactc tactcctgtg tatatgccca aaaaagctga    2220
aagcccaggc actgtggctt acacctgtaa tcccagcact ttaggaggcc gaggcacttg    2280
accccaggat tttgagacca gcctgggcaa catagtactt gttcaagaat caggctgggc    2340
atggtggctc acacctgtaa tcccagcact ttgggaggcc aaggtgggag gatcacttga    2400
ggccaggcat tcgagaccag cctgggcaag atagcaatac ccaccccaa tctctacaaa     2460
agcaagtaat taattaggaa attagccaaa gccaggtgcg gtggctcacg cctgtagtcc    2520
cagcactttg ggaggctgag gtgggcagat tgcttgagtc cagagattcg agaccagcct    2580
aggcaacata tcaaaacccc gtctctacta aaagtaaaaa aagaaaaatt gcactttggg    2640
aggccaaggc gggggatca cctgatgtca ggagttcaag accagcctgg ccaacatggt     2700
gaaaccccat ctctacaaaa atacaaaagt tagccgggca tgatggcagt gtctgtaatc    2760
ccagctactc aggaggctgg gtcggaagaa tcatttgaat ccaggaggcg gaggttgcag    2820
tgaaccaaga ttgtgccatt gcattccagc ctgggtgaca gagcaagcct ccgtctcaaa    2880
aaaaaaaaaa aaaagaaaaa ttagccagat gtggtggtgc atgcctgtgg tcccagctac    2940
tcaggaggct gtggtgggag gattgcttga gcccaagaca ctgaggctgc agtgagccat    3000
gatcacacca ctgcactcca gcctaggcaa ccagagtgag accctgtctc aaaaacaaac    3060
aaacaaacaa aaaccacttt aacagggtat ggtggtgcac acctctagtc ccagctactt    3120
gggaggttga ggcagccgga tcacttgacc ccaggagatc gaggctgcag tccagcctgg    3180
gcaaccgagt gagactgtct caaaagaaa aaaaaaaaa aaaggacata gcagcactat      3240
tcacaaatcc aaaagttaga aataactcag atgtccatca acagatgaat ggataaacga    3300
attgtggtat atacatataa tggactatta ttcagccatt aaaaggaatg aaatattgat    3360
acaggctata aactctatga acattgaaaa cattctaagt gaaaggaaat agacataaga    3420
ggtcacattt tgcaattctt ttttttttt ttttttttt tgagactgag tctcactctg      3480
ttgcccaggc tggagcgcag tggctcgatc tcagctcact gcaacctcca tctcccgaat    3540
tcaagcaatt cttctgcctc agcctcccga gtagctggga ttacatgtag gcatgcacca    3600
ccatgcctgg ctaattttg tactttagt agagatgggg tttcaccatg ttggtcaggc      3660
tggtcttgaa ctccagacct caggtggtcc acccgccttg gcctcccaaa gtgctaggat    3720
tacaggtgtg agccaccatg cccggccaca tgtatggtaa ttattgaatg tgtttggtat    3780
gttcgttgtg ggtgatgaaa tattttggaa ctagatagac gtgatggttg aacaacactg    3840
tggatgcact aaatgccact gaattgtaca ctttaaaatt gttaacttta tgttacatga    3900
atttcaccta aattaacaac aacaacaaaa aagaacttaa gacagcactt ggtttggcta    3960
ttacgtagtt tcgtgacaaa cagtggtcca tctcccagag aactggcccc aggttcctaa    4020
gaaggcaaaa ggagacacag gacctctctg cactattttt tttgcaactt cttatgagtc    4080
tataattatt tcaaaataaa agtctaaaag gaaaataaga acatgtgtga atgtggctgc    4140
cccatgcctc ccaccctcag gtctgacact cagagactga tcacctcttg agagtcctgg    4200
aactcatccc aggttttaga ccctgaatgg cctgtctggg gctggcgtct ggaggcagga    4260
tcaggagcca gctcagagca tagtttaact ttcactttc ttttctccag aggagccagg     4320
aagagagctg tgaccagcag cgtcccttat tcgcttggcc ttggttcctg tttgcactgg    4380
ctacagcagg gcactggccc ctactgtcac cgccacctac acaaagaccc tatctctgag    4440
cgctgcagcc tactgttcag ccccaggttt gaggatggat gccctggacg cttcgaagct    4500
actggatgag gagctgtatt caagacagct gtgaggcccg aggtggggg tggagagtgg    4560
```

```
gatggtcttc agaccttgat ctacaactgc ttgccttctg cttcccatcc acaggtatgt    4620
gctgggctca cctgccatgc agaggattca gggagccagg gtcctggtgt caggcctgca    4680
gggcctgggg gccgaggtgg ccaagaactt ggttctgatg ggtgtgggca gcctcactct    4740
gcatgatccc caccccacct gctggtccga cctggctgcc caggtaagtg tcctgggct     4800 atgggctgcc agaccaagtg gggcacggcc caagaggagt gtctttgctc aggctgcact    4860
ggctctctcc ctagtttctc ctctcagagc aggacttgga aaggagcaga gccgaggcct    4920
ctcaagagct cttggctcag ctcaacagag ctgtccaggt cgtcgtgcac acgggtgaca    4980
tcactgagga cctgctgttg gacttccagg tcagctcagg cctgcagccc tcaagagcag    5040
gaagggctgg gcaatggttt tggccctgct gatcactgtg tccacccagg tggtggtgct    5100
gactgctgca aagctggagg agcagctgaa ggtgggcacc ttgtgtcata gcatggagt     5160 ttgctttctg gcggctgaca cccggggcct cgtggggtga gtaagactgc ctgcccagcc    5220
taccatatta cagccagcaa ctggcctcat gctgtcctca gctccaggct tgctccagtg    5280
cccctccaac cagcctcagg tctatcccag catgcctttc tgattctggt ccccagtcct    5340
gccctctggt tcctccaacc tagcctccag acctgctcca gtaaccctct caaattctag    5400
ttcccaagcc tctccttgca ttccttnccc aattctggcc ctctggccct gcctagtan     5460 ncctatcct  taagtacaat ctgtaagcca cctcagtgac ccctaccacc ccatctcagg    5520
cagttgttct gtgactttgg tgaggacttc actgtgcagg accccacaga ggcagaaccc    5580
ctgacagctg ccatccagca catctcccag gtgggtgctg agctgtaggc attcacccgc    5640
tgaccaagga gaggctgcca gggcctgtgg aaggcaggtc caggcaaccc tgagccaagc    5700
ctcctcctac ccagggctcc cctggcattc tcactctgag gaaagggggcc aatacccact   5760 acttccgtga tggagacttg gtgactttct cgggaattga gggaatggtt gagctcaacg    5820
actgtgatcc ccggtctatc cacgtgcggg gtaagccaat cccattccaa ttccaggtgc    5880
agggcccaag cctccactgg aagtgagcac agcctggccc ttgggatggg ttttctccc    5940 tccaccttct acaaggtgca gcaaggtttg ggacacagat gcaagatagg atggggtgtg    6000
ggaactactc aggctcaagg atcattactg actagactgg aactccctca gaggatgggg   6060
ccctggagat tggagacaca acaactttct ctcggtactt gcgtggtggg gctatcactg    6120
aagtcaagag acccaagact gtgagacatg tgagtgcaag tccatctgag gtaggggagc    6180
ttggtcgcct tgagggggccc atagcattct ggactagacc ctgagccagg tgcccttgca    6240
gaagtccctg gacacagccc tgctccagcc ccatgtggtg gcccagagct cccaggaagt    6300
tcaccatgcc cactgcctgc atcaggcctt ctgtgcactg cacaagttcc agcacctcca    6360
tggccggcca ccccagccct gggatcctgt gagtagtcct gttgctccca cccccagcct    6420
ctgtcattta ttggggtccc acctgccaga ggcaacaatg accattcaca aatccaagtc    6480
tgatctccca acactgcagc ctttagagta gagactggtt ccatggaagt gccaggcaca    6540
catcctgggg actcctgcta cacccgacc  cctcagatct gtgctggaag ctgcactcag    6600
attagtgaag cctcctggac tgctgtctgg tactgggcat cctctggtgg tgctgtgcag    6660
gctggcagca gggccaggcc ttcccaccca ggcttctgct tcctcttctg tggaacaggg    6720
tggatggagg gtggctggaa ggatttgagt caggagtaga gctcaggctg gggctactat    6780
gcccacagag tcctaccaac aggttgatgc agagactgtg gtgggcctgg cccgggacct    6840
ggaaccactg aagcggacag aggaagagcc actggaagag ccactggatg aggccctagt    6900
```

```
gcggacagtc gccctaagca gtgcaaggtg tcttgagcct atggtggcat gctgggtcag    6960
tagctgccca ggaagtgctg aaggtgggca gaggcatagg tgtgggggt actgggaaga     7020 tgtggagatc agtgtgtgtg tcagagggca cccagcgcta gagagcagcc ctggagcctt    7080
caccaacctg ggtgaagcct ccagccagga tctgaggggg gtcaggaggt ggcaggagtg    7140
cccagcctga agtgctgccc ctaggcaatc tccagaagtt catgcctctg gaccagtggc    7200
tttactttga tgccctcgat tgtcttccgg aagatgggga gctccttccc agtcctgagg    7260
actgtgccct gagaggcagc cgctatgatg gcaaattgc agtgtttggg gctggttttc     7320
aggagaaact gagacgccag cactacctcc tggtgagctg tggggtgaga ctgggggtgc    7380
ctttgggaga gccagcccag cccctctggc taaggctgtt cctgccaaca ggtgggcgct    7440
ggtgccattg gttgtgagct gctcaaagtc tttgccctag tgggactggg ggccgggaac    7500
agcgggggct tgactgttgt tgacatggac cacatagagc gctccaatct cagccgtcag    7560
ttcctcttca ggtcccagga cgttggtgtg agtgctgacc cctctccaca ctcctgcatc    7620
ccagaccgtc ctcccataca gcttcccacc caacatcttc ctgccttctt cccagagacc    7680
caaggcagag gtggctgcag cagctgcccg gggcctgaac ccagacttac aggtgatccc    7740
gctcacctac ccactggatc ccaccacaga gcacatctat ggggataact ttttctcccg    7800
tgtggatggt gtggctgctg ccctggacag tttccaggcc cgtgagtgct tgacttcgga    7860
ggtcagtccc ttgcccacag ctgtgccagt cccacttctg acccactgct ccctgccag    7920 ggcgctatgt ggctgctcgt tgcacccact atctgaagcc actgctggag caggcacat     7980 cgggcacctg ggcagtgct acagtattca tgccacatgt gactgaggcc tacagagccc    8040
ctgcctcagc tgcagcttct gaggatgccc cctaccctgt ctgtaccgtg cggtacttcc    8100
ctagcacagc cgagcacacc ctgcaggtag aagcaccct ggagactccc accccaccca     8160
gctcagccct cagctgcaga cctgttctcc acctgatacc tcattcttcc tccctcctcc    8220
acagtgggcc cggcatgagt ttgaagaact cttccgactg tctgcagaga ccatcaacca    8280
ccaccaacag taaggccacc aacagaggca gatgggagtc cagggctcca agcatgagtc    8340
tgcaggactc agtctcacac ttcctcctct ctctgcaggg cacacacctc cctggcagac    8400
atggatgagc cacagacact caccttactg aagccagtgc ttggggtcct gagagtgcgt    8460
ccacagaact ggcaagactg tgtggcgtgg gctcttggcc actggaaact ctgctttcat    8520
tatggcatca aacagctgct gaggcacttc ccacctaata aagtgtgtgg ctaggggttg    8580
ggacgctggg ggctcagggg gaccagactg agcccagcag cttctactta cctacctagg    8640
tgcttgagga tggaactccc ttctggtcag gtcccaaaca gtgtccccag cccttggagt    8700
ttgacaccaa ccaagtgagt gggattctgt agggagctcc aagatagaga tgtggcccct    8760
cagagcagag gtaggcattt ctgcattctg cagagatgca cagatgccca gagagagcca    8820
tgcttgtgca tatatgggtg tctacatgtg aggcaaaggc aggcactcaa acagatccac    8880
aaatggacag tgaccccacc catgcaccat gcctctctgt tctgctctct gctcttggtc    8940
tggctgcagg acacacacct cctctacgta ctggcagctg ccaacctgta tgcccagatg    9000
catgggctgc ctggctcaca ggactggact gcactcaggg agctgctgaa gctgctgcca    9060
cagcctgacc cccaacagat ggccccatc tttgctagta atctagagct ggcttcggct     9120
tctgctgagt ttggtgaggc tcctggccct ggccctcat gctgtctttc aaaggcctga     9180
acctgtcctg tcctcagcct gtgctgcaga aggaagatag ggcctagggg atctacagcc    9240
aatttgctac ctctcaggcc tcctaacctc actcctccat agtttcaggc ttatcctctg    9300
```

```
gtccctcagt aggtcttctc cctgctgcct accccacatc ccagttcttg tggcagattc   9360
ttggcaaaat aaataagtaa ataaataaag tccattggtt cctggggagt gtctagctat   9420
ggcctgcagg tgaggacagg gtcacagagg tcatgagcac acatgggtga agactggggc   9480
ttctagaggg gagattgtag cattaattaa gggggcttct tgatttgatc agggaatagt   9540
aagtgacagg cttggcaaag accaagaata ggcacagggc tccaagaaga gtgcaggaga   9600
caggggctaa ggactgcctc aacatcccct tccctgacag gccctgagca gcagaaggaa   9660
ctgaacaaag ccctggaagt ctggagtgtg ggccctcccc tgaagcctct gatgtttgag   9720
aaggtgggtg cccaagtggc agtgaggagt ggggctgggg agtttgtgga gaaaggtcag   9780
gagctaataa ggtagttttg gagccccttg gcctgaattc cacagctgca gtgttaacac   9840
tactttgact tgggccttac aggatgatga cagcaacttc catgtggact ttgtggtagc   9900
ggcagctagc ctgagatgtc agaactacgg gattccaccg gtcaaccgtg cccaggtaac   9960 cccaccccctt gaggcttggg cctggaggtg gagggcaaac cctggcccta cgccttgggc   10020
ccagaccaaa tctcttgtcc ttggcagagc aagcgaattg tgggccagat tatcccagcc   10080
attgccacca ctacagcagc tgtggcaggc ctgttgggcc tggagctgta taaggtggtg   10140
agtgggccac ggcctcgtag tgcctttcgc cacagctacc tacatctggc tgaaaactac   10200
ctcatccgct atatgccttt tgccccagcc atccagacgg ttgagcccat gatacccac    10260 ccttagccct actaggcctg ggtttcccct gcacctgccc atacaggccc caatctagct   10320
gccggctctc actgaaactc agactgtgca gaagtcctga agactccctc cagccctctt   10380
cctgctatga agccaggctg ggacctgtca gacacaggaa gcagccgtca gccatcccca   10440
cccccaatcc tccaaagccc aggatctggg ggagctgcag ctttaactca ttagtggagc   10500
cagacatccc ccacagtccc ctccttcctt ggagtacccc tgagggtagg tagtggggag   10560
gggaccaggg catcagccca gaaagagtct agcttccccc tgcatggtac ggggggccctg  10620 gcctacctcc tacaagctga gttaaaaggt aataggcttg ccactagagg tgtgggggtct  10680 gcagccctga gtgtatttgt gtcacagttg tgagtgcaac tggggtctgg gcatccccgg   10740
agtgtgggta tggaaggagc aagtttgcac atctgtgcat cagatgggag tgcagggctc   10800
ccatcttcct gtgtcctcaa tgtgggcatg catggagatg catgtgggca cacatgtgtg   10860
tgtttcctgg gcttgtgggc atttgtgttc ctgtgactgc agcgctgtga atgcctccag   10920
ccttgtgccc aggctctgca gttggcattt ccttggggca aggatgaggg tagaaggaat   10980
gccctcatga ggggagaggg cagaggtcat gggccagcac tgggtttctg ctgagcagcc   11040
tggggtccct ctggactagc acacagagcc cctttgtgag gcaccctgcc tctaaccagc   11100
atacaggctg cctttgtcca cagagtgaag caggtgaagg agaagccccc atctcacctc   11160
tagcctagtc tcagcttgac cccagtgtgt tttctcaggg gctgataagc accccctgtc   11220
ctggtctcta gatacctgcc agccatcctt ctgtccttag ctctaggtcc cagaacccca   11280
agactcttgg aaggaaggaa gggacaggag gaggaagcct ctatgcattg tatccctgct   11340
ggggtctctg ggacagtggg gcctggtgg tcactgtgcc cttttgcccct gtgtcccaat    11400 gagtagccca aggcactggc agtacataca agattggggg acaggatgtg cccccagct    11460 cccagccttg tctttgagga acaagcagct ttatcagagg ctgcaggggc cctgctctgg   11520
gtttcctcag gaagcaccac cgccgcatcc cccactctca caactggccc atgtgatgga   11580
tcgtctgttt ccctgtgcgg gccccatagc cccatttcct gtgctggccc cggcctggac   11640
```

```
ggggaggggg ctgagactct gggcccagat cccacctccc ccccaccccc caccccctgg    11700
ctcctgtttc ctgctagtcc agctcttccc ctaggaaagg ctgctggtaa ctgggatggg    11760
ggttgggggg aggtaagaag tctctgactc ctcctctacc tcatcccagt tccatcacct    11820
gaagtggacc tcttgggacc gtctgaaggt accagctggg cagcctgaga ggaccctgga    11880
gtcgctgctg gctcatcttc aggagcagca cgggttgagg gtgaggatcc tgctgcacgg    11940
ctcagccctg ctctatgcgg ccggatggtc acctgaaaag caggcccagc acctgcccct    12000
caggtgagcc cacttgggct ttagacaggc cccaccagtc cctggaggct ggggctaggg    12060
accacactgc cttttgtctt cccagcccca ttctgggccc ctcacacctt cccaagcatt    12120
ctttccccaa atggagccag caaacaggct ggaggtgggg tgagggccga gagctgagga    12180
ggagtcttcn anggagctcg tatttggcca gcccatggct cccacatgct gcacagnnnn    12240
ttcacagcca ctcctaagga cccatagctt cctgcctcct gcttggcctc atcagctgct    12300
cctaaaatag tttcagatgt ttcctgtctt gagcagctcc tgctcctggc ttgggctcct    12360
gacggcctgc cagcaccctc tctagtccat gccaggctgc cttctgcttg ccatggctca    12420
cctctccaat ctcccctaaa cccacccta ccagggtgac agaactggtt cagcagctga    12480
caggccaggc acctgctcct gggcagcggg tgttggtgct agagctgagc tgtgagggtg    12540
acgacgagga cactgccttc ccacctctgc actatgagct gtgacaaggc agccaccctg    12600
tcacctagct caatggagcc ccggatccca agccctgcat tgtaagccca cagtaggcac    12660
tcaataattg cttgttaaag gaaggcattg cagagaggac ggacgataga aaacagtgca    12720
ctaatgcaca cgggtgtgac atgggcatga cagggaccttt cacacagaga aaaaaagctc    12780
ttcagaagat ttgtctccct gggcagtgct cacagggctg gggctgcctc ttagtgcctc    12840
aggggtatgg agccaggaca gtctagaaaa aaggctttta ttgtcccagg ctggagggca    12900
gggtcagagg tagctgacat cattgcagat gatgggctgg cggctacgac agctcatgag    12960
agctgcaaag ctgagacat                                                12979
```

THERAPEUTIC AND DIAGNOSTIC METHOD FOR ATAXIA-TELANGIECTASIA

This application claims priority under 35 U.S.C. §119(e) from U.S. Provisional Application Ser. No. 61/565,715, filed 1 Dec. 2011, entitled "Therapeutic and Diagnostic Method for Ataxia-Telangiectasia," and from U.S. Provisional Application Ser. No. 61/706,863, filed 28 Sep. 2012, entitled "An Improvement to Targeting the ISG15 Pathway in Ataxia-Telangiectasia: A Novel Therapeutic Approach for Treating A-T;" the contents of both provisional applications are fully incorporated by reference herein.

This invention was made with government support under grant number R21NS060960 awarded by the National Institutes of Health/National Institute of Neurological Disorders and Stroke. The government has certain rights in the invention.

Ataxia-telangiectasia (A-T) is a childhood disease with an incident of 1 in 40,000 children in the U.S. and 1 in 200,000 worldwide each year (1-4). Ataxia refers to uncoordinated movements, such as walking, and telangiectasia is the enlargement of capillaries just below the surface of the skin, a feature characteristically exhibited by A-T patients (3). It is a rare inherited disorder that mainly affects nervous and immune systems (3). A-T patients are also at an increased risk of developing cancer (5). Affected individuals are very sensitive to radiation, including medical x-rays (6, 7). This feature has been attributed to the defective ATM gene (Ataxia Telangiectasia Mutated) in A-T patients (8). ATM is a serine/threonine protein kinase that is activated upon DNA damage (9). Activated ATM kinase phosphorylates several key proteins that initiate activation of the DNA damage checkpoints, cell cycle arrest, and DNA repair to favor cell survival (10). Therefore, a defect in ATM has severe consequences in DNA damaged cells, especially in terminally differentiated cells such as neurons (11). Indeed, a defective DNA repair pathway has been linked to the progressive neurodegeneration in A-T patients (11-14). Whether the defect in DNA repair is solely responsible for neurodegeneration in A-T is unknown.

Altered expression/mutations in genes involved in protein turnover pathways have been linked to neurodegeneration in other neurological diseases. Accumulation of misfolded protein deposits in affected brain regions are reported in neurodegenerative diseases including Alzheimer's, Parkinson's, Creutzfeldt-Jakob, and Huntington's disease (15, 16). In most cases, proteinaceous deposits were composed of ubiquitin conjugates, suggesting a failure in their degradation by the ubiquitin/26S proteasome, the major cellular proteolytic machinery responsible for targeted destruction of short-lived and abnormal proteins in mammalian cells (17). The potential accumulation of non-degraded ubiquitylated proteins in neurons of A-T patients has been indicated (12, 13, 18, 19). However, the events leading to the accumulation of non-degradable ubiquitylated proteins and the potential causal relationship to neuronal degeneration in A-T patients is unknown.

ISG15 (Interferon Stimulated Gene 15) protein is a member of the UBL (ubiquitin-like protein) class of proteins (21, 22), and can be induced upon interferon treatment (23). Intracellular ISG15 exists in two forms: (i) free and (ii) conjugated to target proteins. ISG15 is conjugated to its target proteins in an enzymatic cascade involving an E1 (UbE1L), E2 (UbcH8), and E3 (HERC5 and others) (21-23). Free ISG15 has been suggested to have cytokine-like activity (23). Conjugated ISG15 exerts its biological effect by inhibiting polyubiquitylation of cellular proteins (24-26).

ISG15 has been shown to inhibit the ubiquitin pathway by modulating the activities of the ubiquitin E2/E3 ligases (27-30). ISG15 inhibits the ubiquitylation of Gag and Tsg101 which prevents their interaction and blocks retroviral replication and release (67). In addition, ISG15 inhibits Nedd4 ubiquitin ligase and, consequently, the ubiquitylation of VP40 viral particles essential for budding of Ebola viruses (27). Furthermore, ISG15 inhibits ubiquitin-mediated degradation of IRF3, a transcription factor involved in the interferon response, and enhances innate antiviral immunity (68). ISG15 also inhibits polyubiquitylation by modulating the activities of selected ubiquitin E2 and E3 ligases (27-29, 69). In normal cells, the ISG15 pathway is not constitutively elevated. However, when aberrantly overexpressed, ISG15 may conjugate to and inhibit the activity of ubiquitin E2/E3 ligases as demonstrated with Nedd4 (27), UbcH6 (69), and UbcH13 (28, 29). ISG15 has also been shown to inhibit bulk polyubiquitylation and the subsequent 26S proteasome-mediated degradation of target proteins in breast cancer cells (24). Elevated expression of ISG15 suppresses camptothecin-induced proteasome-mediated degradation of topoisomerase I in breast cancer cells (37). ISG15 has been shown to be elevated and conjugated to cellular proteins in A-T cells (70).

Under conditions where proteasome function is compromised, the large ubiquitin containing protein aggregates have been shown to be cleared by autophagy (31-34); a second major proteolytic pathway that targets destruction of long-lived cellular proteins, larger macromolecular complexes, and defective organelles through lysosomes (35, 36).

U.S. Patent Application Publication No. 2005/0019847 discloses methods to identify compounds that alter the conjugation of ISG15 with target proteins, and methods to identify patients with a malcondition characterized by an altered level of ISG15-conjugated proteins.

U.S. Patent Application Publication No. 2008/0261226 discloses biomarkers and diagnostic methods of early detection of neural cell injury using a mouse model of amyotrophic lateral sclerosis.

U.S. Patent Application Publication No. 2010/0111874 discloses methods for treating and detecting cancer based on levels of ISG15.

BRIEF SUMMARY

I have demonstrated that ATM kinase regulates proteasome-mediated protein turnover through suppression of the expression of the ubiquitin-like protein ISG15 (Interferon Stimulated Gene 15). Using both ATM kinase deficient cells (A-T cells) and ATM kinase proficient cells (ATM+ cells), I have shown the following: (1) The ISG15 pathway is constitutively elevated in A-T cells, and suppressed in ATM+ cells; (2) autophagy is activated to compensate for impaired proteasome function in A-T cells, and is not activated in ATM+ cells; (3) ISG15 inhibits the ubiquitin pathway in A-T cells, while the ubiquitin pathway is functional in ATM+ cells; and (4) genotoxic stress (e.g., UV) induces bafilomycin (an autophagy inhibitor)-resistant degradation of the proteasome and autophagy substrates in A-T cells, and genotoxic stress induces only minimal degradation (which is protected by bafilomycin) of the proteasome and autophagy substrates in ATM+ cells. Silencing of the ISG15 pathway restored both the ubiquitin and autophagy pathways, and the UV-mediated degradation of their substrates in A-T cells. The above results lead to the conclusion that the ATM kinase negatively regulates the ISG15 pathway, and the constitutively elevated ISG15 pathway induces proteinopathy in A-T cells, and in A-T patients. These findings indicate for the first time that protein turnover is impaired in A-T cells due to elevated expression of the ISG15 conjugation pathway, which contributes to progressive neurodegeneration in A-T patients. Thus the ISG15 pathway (for both free ISG15 secreted in blood and intracellular ISG15 conjugates) is a new target for both detection and treatment of A-T. Modulators of the ISG15 pathway that lead to lowered expression of ISG15 can be used to inhibit or attenuate neurodegeneration in A-T patients. In addition, an inhibitor of the early phase of autophagy, 3-MA, and ISG15 shRNA were shown to be effective in restoration of the impaired protein turnover pathways in A-T cells, and thus would be effective in decreasing the neurodegeneration in A-T patients. I have also shown that defective mitophagy and macroautophagy in A-T patient cells is caused in part by elevated expression of ISG15 in A-T cells. In addition ISG15 inhibitors are expected to attenuate ISG15 expression with the concomitant improvement in the neurodegeneration of A-T patients. This improvement can be monitored by MRI, PET, or other imaging tools.

BRIEF DESCRIPTION OF DRAWINGS

FIG. 2C illustrates A-T and ATM+ cells treated with the protein synthesis inhibitor CHX in the presence (lanes 3 and 6) or absence (lanes 2 and 5) of the proteasome inhibitor MG132 (10 µM) for 6 h, and then cell lysates were analyzed by immunoblotting using an anti-p53 antibody. The intensity of the p53 bands was measured using a Kodak Image station 2000R (BioRad), and the results are shown in the bar graph (right panel). The filter used for immunoblotting was stained with Ponceau S to assure equal protein loading (lower panel). All of the experiments were repeated at least three times and the representative experiments are shown.

FIG. 2D illustrates A-T and ATM+ cells treated with the protein synthesis inhibitor CHX (10 µg/ml) in the presence (lanes 3 and 6) or absence (lanes 2 and 5) of the proteasome inhibitor MG132 (10 µM) for 6 h, and cell lysates were analyzed by immunoblotting using an anti-STAT3 antibody. Intensity of the STAT3 band was measured using Kodak Image station 2000R (BioRad), and the results are shown in the bar graph (right panel). The lower portion of the same membrane filter was immunostained with the anti-tubulin (lower panel) antibody. All of the experiments were repeated at least three times and the representative experiments are shown.

FIG. 7B illustrates the results from deparaffinized human brain tissue sections from the normal subject (UMB#1455) and A-T patients (UMB#1722, 4663) described in FIG. 7A, after being double stained with anti-ISG15 (polyclonal) and anti-K63-linkage specific polyubiquitin (monoclonal) (1:100) antibodies. After washing with PBS, sections were stained with Alexa Fluor 488 goat anti-rabbit IgG secondary antibody to detect ISG15 and goat polyclonal secondary antibody to mouse IgG (Cy5®) to detect Lys63-linked polyubiquitin conjugated proteins. Sections were mounted in gold antifade mounting medium and examined using Nikon E600 epifluorescence microscope (Nikon) (20× magnification, scale bar, 100 um). Arrows in the third panel indicate ubiquitin/ISG15 double-positive inclusions in the merged A-T brain sections.

FIGS. 10B and 10D show average values (±SEM) of % degradation of LC3 (FIG. 10B) or p62 (FIG. 10D) from three independent experiments. All control values (−UV and +Bafl) were normalized to 100%, and values for experimental treatments were expressed as percent variations over control.

In FIG. 17B, bar 1: No drug and +Bafl controls; bar 2:+UV; and bar 3: +Bafl +UV.

FIG. 19A, bars 1: No drug and +Bafl controls; bars 2:+UV; and bars 3: +Bafl +UV.

In FIG. 19B, bars 1: No drug and +Bafl controls; bars 2:+UV; and bars 3: +Bafl +UV.

DETAILED DESCRIPTION

Figure 1A:
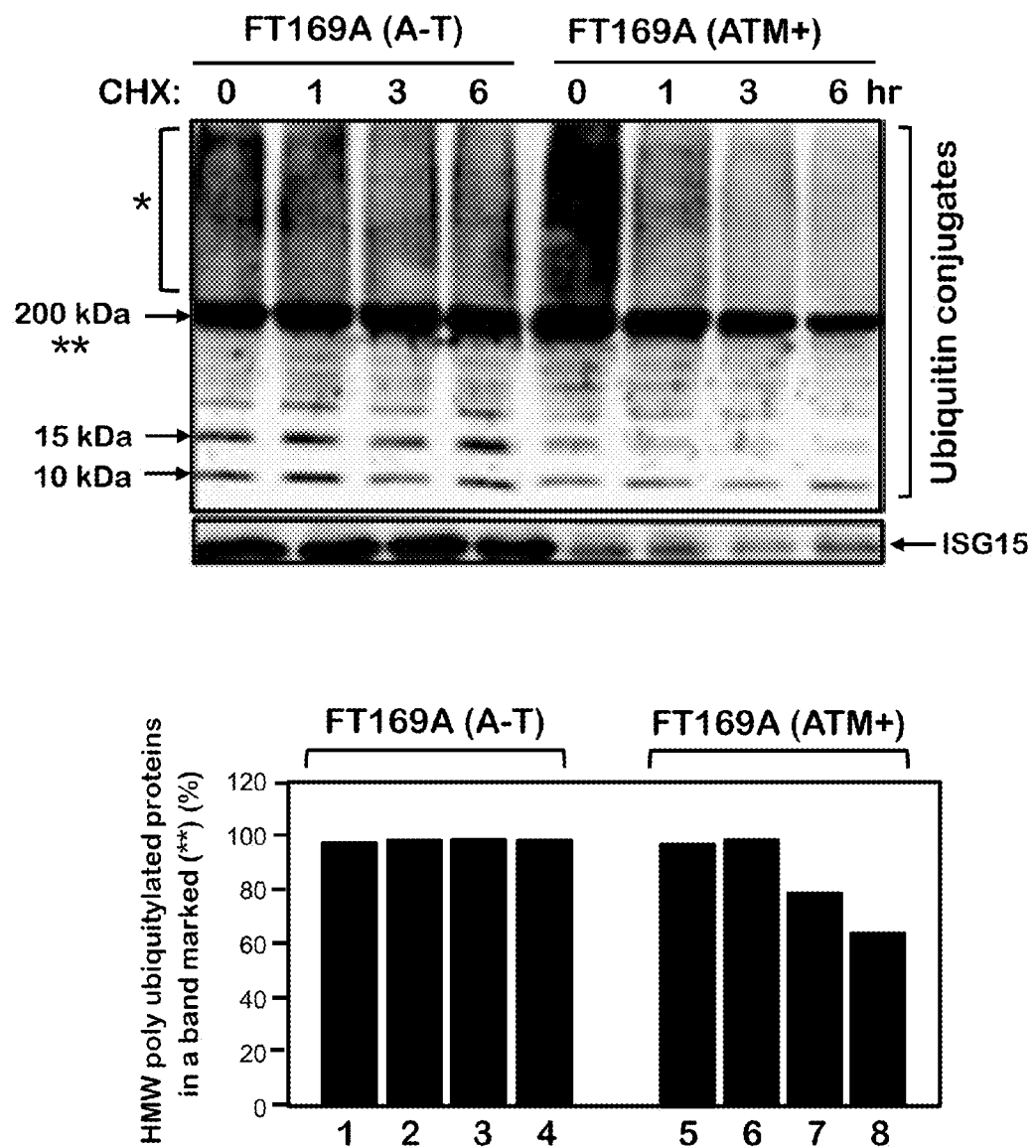
FIG. 1A illustrates cell lysates from A-T cells and ATM+ cells treated with the protein synthesis inhibitor CHX for 0, 1, 3, and 6 hours, and analyzed using discontinuous (15%) SDS-PAGE followed by immunoblotting with anti-ubiquitin antibody. The symbols * and  mark the position of high-molecular-weight (HMW) polyubiquitylated proteins. Quantitation of the high-molecular-weight (HMW) polyubiquitylated proteins (shown as ) is shown in the bar graph.

Ataxia-telangiectasia (A-T) is a childhood disease with diverse clinical manifestations that results from inactivation of the ATM (Ataxia telangiectasia mutated) kinase. I have demonstrated that targeted proteasome-mediated degradation is impaired in A-T cells. In addition, reduced protein turnover in A-T cells is associated with elevated expression of ISG15, an ubiquitin-like protein shown to antagonize the ubiquitin pathway. Furthermore, ATM acts as a suppresser of the ISG15 pathway. These results indicate a novel functional role for ATM in protein turnover through suppression of constitutively activated ISG15 pathway in normal cells. Due to the inactivation of ATM kinase, ISG15 pathway is elevated which, in turn, inhibits ubiquitin-mediated protein turnover in A-T cells.

As shown below, ISG15 was elevated in A-T astroglial cells and brain tissue obtained from ATM knockout mice and in A-T patients. In addition, the presence of ubiquitin/ISG15 double-positive inclusions was found in brain sections obtained from A-T patients. These results support that ablation of ATM kinase leads to the elevated expression of ISG15. A clinical treatment for A-T patients would be the use of drugs that inhibit/modulate the ISG15 pathway to decrease ISG15 expression that would prevent proteinopathy associated with A-T and, consequently, neurodegeneration.

I have also shown that the basal autophagy pathway is activated in the ubiquitin pathway-compromised A-T cells. Genotoxic stress (e.g., UV radiation), but not metabolic stress (e.g., serum deprivation), induced irrepressible degradation of polyubiquitylated proteins in the ubiquitin pathway compromised A-T cells, but not in ATM+ cells. The proteasome inhibitor MG132 and autophagy inhibitor Bafilomycin A1 (Bafl A1) blocked the UV-induced degradation of the proteasome and autophagy substrates in ATM+ cells, but neither worked in A-T cells. In addition, camptothecin, another genotoxic agent, triggered Bafl A1-resistant degradation of polyubiquitylated proteins in A-T cells. Together, these results indicate that genotoxins induce aberrant degradation of autophagic flux in A-T cells. Without wishing to be bound by this theory, I believe that autophagy provides an alternate compensatory route for degradation of the proteasome and autophagy substrates in the ubiquitin pathway compromised A-T cells.

As seen in the Examples below, I have shown that the constitutively elevated ISG15 impairs targeted proteasome-mediated degradation in A-T cells, and that basal autophagy is activated in human A-T cells and brains of A-T patients. To test if the impairment of the proteasome and autophagy pathways is due to the increased expression of the ISG15 pathway, I silenced ISG15 expression in A-T cells and then monitored the status of protein turnover pathways in ISG15-silenced A-T cells. I found that ISG15-specific siRNA restored the proteasome function, also attenuated basally and genotoxin-activated autophagy in A-T cells. These results indicate that the deregulation of the protein turnover pathways is a consequence of the elevated expression of ISG15 in A-T cells, and thus indicate a causal contribution of the ISG15-mediated defective protein turnover in A-T neurodegeneration.

Selective inhibitors of ISG15 expression include, but are not limited to, agents such as microRNA, shRNA, siRNA, antisense, or ribozyme molecules specifically targeted to a nucleic acid molecule encoding ISG15 (e.g., GENBANK Accession No. AY168648; human ISG15 mRNA sequence). Such agents can be designed based upon routine guidelines well-known in the art. For siRNA target sites in a gene of interest can be 19-27 nucleotides in length (e.g., the siRNA used below targeted nucleotides numbered from 232-250 in Accession No. AY168648). (See Example 1 below, and U.S. Patent Application Publication No. 2009/0131357).

Selective inhibitors of the ISG15 pathway include, but are not limited to, agents such as microRNA, shRNA, antisense, or ribozyme molecules specifically targeted to a nucleic acid molecule encoding UbcH8 (E2-ISG15; e.g., GENBANK Accession No. AF031141 (human UBcH8 mRNA sequence)), UbE1L (E1-ISG15; e.g., GENBANK Accession No. AF294032 (human UbE1L mRNA sequence)), and any one of the several E3 ligases that conjugates ISG15 to the cellular proteins in A-T cells.

I have also demonstrated that ISG15 is elevated in various lymphoblast and fibroblast cells. ISG15 is also highly elevated in the murine $Atm^{-/-}$ and $Atm^{-/-}$ cerebellum, the specific brain region affected by A-T disease. On the other hand, very little expression of ISG15 was seen in the cortex of mice. In agreement with these results, ISG15 was shown to be elevated in brain tissues obtained from different patients diagnosed with A-T disease. In contrast, ISG15 was minimally expressed in normal cells, as well as mice and human brain tissues. Together, these results indicate that ISG15 is constitutively elevated in Ataxia Telangiectasia disease.

I have discovered that "ISG15 proteinopathy" mechanism is an underlying cause of A-T neurodegeneration that is distinct from the current central dogma that defective DNA repair contributes to cerebellar neurodegeneration in A-T patients. One embodiment of the invention is directed towards methods to diagnose A-T using ISG15 (in serum); autophagy markers such as LC3-I and II, lysosomes, and autophagic vacuoles; and mitophagy markers such as complex-I, decreased mitochondrial membrane potential, increased levels of mitochondrial superoxide, and mitochondrial mass in samples from A-T patients as prognostic/diagnostic markers, and to treat A-T by targeting the elevated ISG15 pathway in A-T patients. The samples from A-T patients could include, for example, blood cells, plasma, serum, blood mononuclear cells.

Detection of ISG15 and autophagy (macroautophagy and mitophagy) markers in A-T mice and/or human cerebellar tissue sections, skin primary fibroblast cells, cerebrospinal fluid (CSF), peripheral blood cells, and blood serum can also be conducted using procedures that are well known in the field and similar to those described below in the Examples.

The presence of ISG15 in the serum can be used as a diagnostic/prognostic marker for A-T disease. Consistent with this belief, the most consistent laboratory marker alphafetoprotein (AFP) is elevated in A-T patients after the age of two years. Another embodiment of the invention would be to routinely test for ISG15 along with AFP as a serum markers for A-T diagnosis using ELISA and/or immunoblotting analysis.

Another embodiment of the invention is based on the finding that autophagy is elevated in A-T patients. The detection of the autophagy and mitophagy markers (LC3I and II proteins, lysosomes, autophagic vacuoles, various mitochondrial markers) using immunostaining and/or electron microscopy in peripheral blood and skin fibroblast cells obtained from the A-T patients can be used as prognostic/ diagnostic markers for A-T. In addition, these markers can be used to evaluate the therapeutic response of various drugs during or after treatment.

Another embodiment of the invention is based on the finding that the ubiquitin pathway is attenuated in A-T cells. Levels of the substrates of the ubiquitin pathway can be tested in peripheral blood cells obtained from the A-T patients and used as prognostic and/or diagnostic markers for A-T. In addition, these markers can be used to evaluate the therapeutic response of various drugs during and/or after treatment.

I will also develop a high-throughput assay to identify potential inhibitors of ISG15 expression in vitro using a cell culture model. For this purpose stable clones of A-T cells expressing ISG15p-fused to luciferase will be generated. Using these cells small molecule inhibitors will be screened that can inhibit the expression of ISG15-luciferase using immunofluorescence and/or Western blotting analysis. Commercially available chemical and natural compound libraries will be used for this experiment.

Alternatively, ISG15 in the medium can be monitored using ELISA or similar monitoring techniques. For high throughput screening of small molecule inhibitors, A-T cells (for example, fibroblast, astrocytes, etc.) will be plated into 96 well plates at 4000 cells/well. The following day, compounds will be added as described above. The plates will then be incubated at 37° C. in a $CO_2$ incubator for various times (2-4 days). ELISA will be performed on the culture media to detect ISG15 using anti-ISG15. Hits will be identified as those compounds that inhibited the ISG15 readout (luciferase and ELISA) by greater than three standard deviations of the mean of the compounds on each plate as compared to the untreated control. These compounds will be selected and their activity will be confirmed using the same assay.

The invention also provides methods for screening for inhibitors of the ISG15 pathway (ISG15 and its conjugating enzymes UbE1L, UbcH8, and one of the several identified and unidentified E3 ligases) that could decrease neurodegeneration in A-T patients using western blotting analysis.

In another embodiment ex vivo brain slices from A-T mice models will be used to test the effect of potential inhibitors that would inhibit ISG15 expression or neurodegeneration by monitoring the decrease in ISG15 concentration or the change in autophagic structures (vacuoles, lysosomes) in the presence/absence of genotoxic stress using electron microscope or immunoblotting assays.

In addition, these inhibitors will also be tested for ability to attenuate the expression of the "ISG15 pathway enzymes" (UbE1L, UbcH8 and E3 ligases (identified and as yet unidentified) since ISG15 conjugation contributes to the defective protein turnover in A-T cells.

In another embodiment, the presence of elevated ISG15 in serum can be used to diagnose A-T patients prone to developing neurodegeneration.

In another embodiment, neurodegeneration in A-T patients can be ameliorated or inhibited using compounds that decrease the expression of ISG15, or that restore protein turnover (restores ubiquitin and autophagy pathways) in the absence/presence of genotoxic stress (e.g., UV).

A-T patients are also at an increased risk of developing cancer, particularly cancer of immune system cells (lymphoma) and blood cells (leukemia); however, many patients are also predisposed to solid tumors. Since the ISG15 pathway is also elevated in cancer, and ISG15 shRNA reverses cancer phenotypes, I propose that inhibitors of the ISG15 pathway could also be used to reduce cancer-risks in A-T patients.

As used herein, an "effective amount" of a compound is an amount, that when administered to a patient (whether as a single dose or as a time course of treatment) inhibits or reduces the expression of ISG15 or that decreases autophagy to a clinically significant degree; or alternatively, to a statistically significant degree as compared to a control. "Statistical significance" means significance at the $P<0.05$ level, or such other measure of statistical significance as would be used by those of skill in the art of biomedical statistics in the context of a particular type of treatment.

By "treating" is meant the medical management of a subject, e.g. an animal or human, with the intent that a prevention, cure, stabilization, or amelioration of the symptoms or condition will result. This term includes active treatment, that is, treatment directed specifically toward improvement of the disorder; palliative treatment, that is, treatment designed for the relief of symptoms rather than the curing of the disorder; preventive treatment, that is, treatment directed to prevention of disorder; and supportive treatment, that is, treatment employed to supplement another specific therapy directed toward the improvement of the disorder. The term "treatment" also includes symptomatic treatment, that is, treatment directed toward constitutional symptoms of the disorder. "Treating" a condition with the compounds of the invention involves administering such a compound, alone or in combination and by any appropriate means, to an A-T patient or an animal with similar symptoms. The effectiveness of a treatment can be monitored in any method known to monitor neurodegeneration, including without limitation, use of MRI or PET imaging techniques.

Part A: Role for ATM in Regulating Proteasome-Mediated Protein Degradation through Suppression of ISG15 Conjugation Pathway Example 1

Materials and Methods

Human tissues and Animal Studies. Frozen human midbrain tissues containing specifically substantia nigra were obtained postmortem from patients with confirmed A-T disease and control individuals (without any known disease). Slides with paraffin-embedded sections of the midbrain tissues were used in immunoflorescence study. Human brain tissues and tissue sections were obtained from the NICHD Brain and Tissue Bank for Developmental Disorders at the University of Maryland under protocols approved by the University of Maryland Institutional Review Board.

Animal study was carried out in strict accordance with the recommendations in the Guide for the Care and Use of Laboratory Animals of the National Institutes of Health. The protocol was approved by the Louisiana State University Health Sciences Center—NO Institutional Animal Care and Use Committee under its assurance with the Office of Laboratory Animal Welfare of the National Institutes of Health.

Cells. Normal lymphoblast L40 and A-T lymphoblast L3 (ATM−) cells, as well as FT169A (ATM+) and FT169A (ATM−) fibroblast cells, were obtained from Dr. Y. Shiloh at Tel Aviv University, Ramat Aviv, Israel. FT169A (ATM−) cells were derived from FT169A cells (ataxia telangiectasia cells) by stable transfection with the expression vector alone as described (71). FT169A (ATM+) cells were derived from FT169A cells by stable transfection with full-length ATM cDNA (71). The lymphoblast and fibroblast cells (normal and A-T) were obtained from the American Type Culture Collection (ATCC), Manassas, Va. FT169A (ATM+) FT169A (ATM–) cells were cultured in DMEM (Dulbecco's Modified Eagle Medium; Cellgro, Manassas, Va.) supplemented with hygromycin B (50 µg/ml) (Cellgro). L40 and L3 cells were cultured in RPMI (Roswell Park Memorial Institute; Cellgro). All other normal and A-T fibroblast cells were cultured in DMEM and lymphoblast cells were cultured in RPMI medium according to ATCC instructions.

Immunoblotting and immunofluorescence analysis. Analysis of ISG15 in cultured cells: Cells ($5\times10^5$) were cultured in 35 mm tissue culture plates. Cells were then lysed using a SDS-PAGE sample buffer. Cell lysates were analyzed by SDS-PAGE in 15% (unless indicated otherwise) gel and immunoblotted according to the published procedure (48). Cell lysates were analyzed by immunoblotting with anti-ISG15 (raised against human ISG15) as described (23), anti-ubiquitin (Sigma-Aldrich-Aldrich, St. Louis, Mo.), anti-HA (gift from Dr. Walworth at RWJMS/UMDNJ), anti-p53 (Santa Cruz Biotechnology, Santa Cruz, Calif.), anti-STAT3 (Cell Signaling Technology, Danvers, Mass.), and anti-GFP (Abcam, Cambridge, Mass.) antibodies as indicated using the ECL Western procedure (Pierce, Rockford, Ill.) and the Kodak Image Station 2000R.

Analysis of ISG15 expression in brain tissues of Atm knockout mice: Atm knockout mice are described (72). Brain tissues were obtained from 3 week-old wild type (WT) or Atm knockout littermates and stored in liquid nitrogen prior to processing. For detecting ISG15 and its conjugates, frozen tissues were weighed, cut into small pieces, and placed in test tubes containing SDS gel sample buffer. Tissue samples were then sonicated with a Tissue-Tearor (Biospec Products, Inc.; Bartlesville, Okla.). Sonicated samples were immediately boiled for 10 minutes at 100° C. and then centrifuged at 13,000×g for 10 minutes. Cleared supernatants containing SDS-solubilized protein extracts were analyzed by SDS-PAGE in 15% gel and immunoblotted using anti-ISG15 raised against mouse ISG15 (a gift from Dr. Knobeloch, Institute of Molecular Pharmacology, Berlin, Germany).

Analysis of ISG15 expression in primary cortical astrocytes: Primary cortical astrocytes prepared from the brains of postnatal day-4 wild type and Atm knockout littermates were maintained as monolayers in DMEM/F12 (1:1 mix) supplemented with a 15% fetal calf serum, 2 mM L-glutamine, 100 U/ml penicillin, 100 µg/ml streptomycin, and 10 ng/ml of mouse epidermal growth factor (Sigma-Aldrich) and were used at passage 2. Cells were lysed using an SDS gel sample buffer. SDS-PAGE analysis and immunoblotting using mouse anti-ISG15 were carried out as described above.

Analysis of ISG15 expression in brain tissues of A-T patients by Western Blotting: Frozen tissues were stored at –80° C. until use. Tissue processing and ISG15 analysis in tissue lysates were carried out as described above.

Analysis of ISG15 expression in brain tissue sections by immunofluorescence staining: For double immunofluorescence, tissue sections were deparaffinized in xylene and incubated with the ISG15 (polyclonal) (1:100) and polyubiquitin (K63-linkage-specific) (monoclonal HWA4C4 (Enzo Life Sciences; Farmingdale, N.Y.)) primary antibodies (1:100) and for 1 hour. After washing in PBS, sections were stained with Alexa Fluor 488 goat anti-rabbit IgG secondary antibody (Invitrogen; Grand Island, N.Y.) and goat polyclonal secondary antibody to mouse IgG (Cy5®) (Abcam). Sections were mounted in gold antifade mounting medium (Invitrogen) and examined using Nikon E600 epifluorescence microscope (Nikon) (20× magnification). All the operations were performed at room temperature.

siRNA Knockdown of ISG15. A 21-nucleotide duplex siRNA targeting ISG15, and control siRNA were purchased from Dharmacon Research, Inc. (Lafayette, Colo.). The siRNA targeting ISG15 corresponds to region 232-250 (Accession# AY168648). The siRNA transfection protocol was followed with slight modifications as described (73). FT169A (ATM–) cells were cultured to semi-confluency and transfected with ISG15 siRNA using Oligofectamine (Invitrogen). Seventy-two hours after siRNA transfection, cells were further transfected with HA-ubiquitin expression plasmid using PolyFect (Qiagen) for another 24 hours.

siRNA knockdown of UbcH8. A 21-nucleotide duplex siRNA targeting UbcH8 siRNA was purchased from Dharmacon Research, Inc. The siRNA targeting UbcH8 corresponds to the region 237-255 (Accession# AF031141). The UbcH8 siRNA transfection, followed by HA-ubiquitin transfection, into FT169A cells was carried out as described above.

Example 2

Protein Polyubiquitylation and Degradation is Reduced in Cells Deficient in ATM

To test whether the defective ubiquitin-mediated degradation of cellular proteins contributes to neurodegeneration in A-T, the rate of degradation of overall cellular polyubiquitylated proteins was monitored in FT169A (A-T) (ATM null) and FT169A (ATM+) (ATM reconstituted FT169A) isogenic cells as described (71) using the protein synthesis inhibitor cycloheximide (CHX) (Sigma-Aldrich). In FIG. 1A, FT169A (A-T) (lanes 1-4) and FT169A (ATM+) (lanes 5-8) cells were treated with the protein synthesis inhibitor CHX (10 µg/ml) for 0, 1, 3, and 6 hours. Cell lysates were analyzed using discontinuous (15%) SDS-PAGE followed by immunoblotting with anti-ubiquitin antibody. The symbols * and  mark the position of high-molecular-weight (HMW) polyubiquitylated proteins. Quantitation of the high-molecular-weight (HMW) polyubiquitylated proteins (shown as ) is shown in the bar graph.

As shown in FIG. 1A, the level of polyubiquitylated proteins (see protein species marked by * (smear of high molecular weight (HMW) ubiquitin-conjugated (polyubiquitylated) proteins and ** (high molecular weight polyubiquitylated proteins migrating as a compressed band) remained relatively unchanged in FT169A (A-T) cells up to six hours in the presence of CHX (compare lanes 1 and 4 and lower panel for quantification), suggesting minimal turnover of polyubiquitylated proteins in A-T cells. By contrast, the level of polyubiquitylated proteins (marked by* and **) was reduced by more than 30% within 6 hours in FT169A (ATM+) cells under the same conditions (FIG. 1A, compare lanes 5 and 8 and lower panel for the quantification). An increased steady state level of the high molecular weight (HMW) ubiquitin-conjugated (polyubiquitylated) proteins (marked by *) was also seen in FT169A (ATM+) as compared to FT169A (A-T) cells (FIG. 1A, compare lanes 1 and 5) in Western analysis using anti-ubiquitin antibodies. The same membrane shown in FIG. 1A was stripped and re-probed with anti-ISG15 antibodies. The band intensities of the ISG15 protein remained the same in FT169A (A-T) (lanes 1-4) and (ATM+) (lanes 5-8) cells (note that ISG15 protein levels are low in ATM+ as compared to A-T cells (see discussion below)) treated with CHX. These results revealed that targeted degradation of the polyubiquitylated proteins is specifically altered in A-T cells.

Figure 1B:
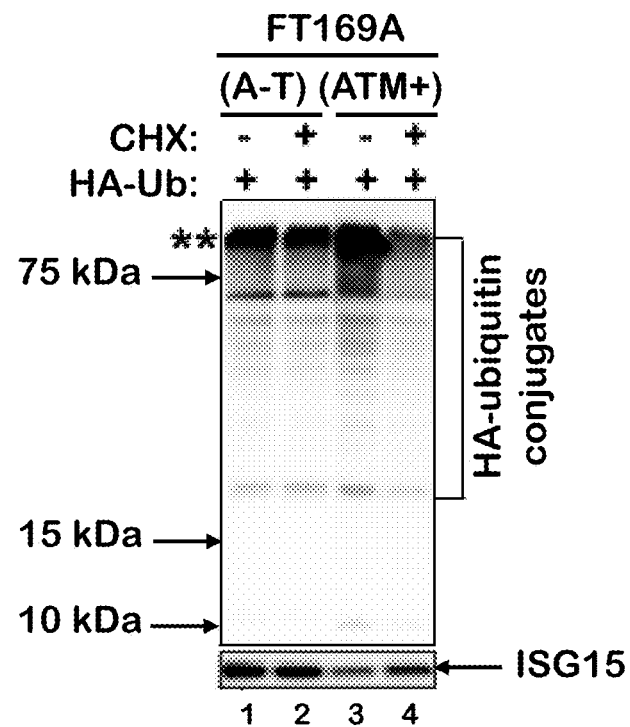
FIG. 1B illustrates both A-T and ATM+ cells transfected with HA-ubiquitin, then treated with the protein synthesis inhibitor CHX (marked on top of each lane) for 6 hours, and then lysates analyzed using 15% SDS-PAGE followed by immunoblotting with anti-HA antibody. The symbol  marks the position of polyubiquitylated proteins (compressed due to the gel electrophoresis conditions). Quantitation of the high-molecular-weight (HMW) polyubiquitylated proteins (shown as ) is shown in the bar graph.
Figure 1B:
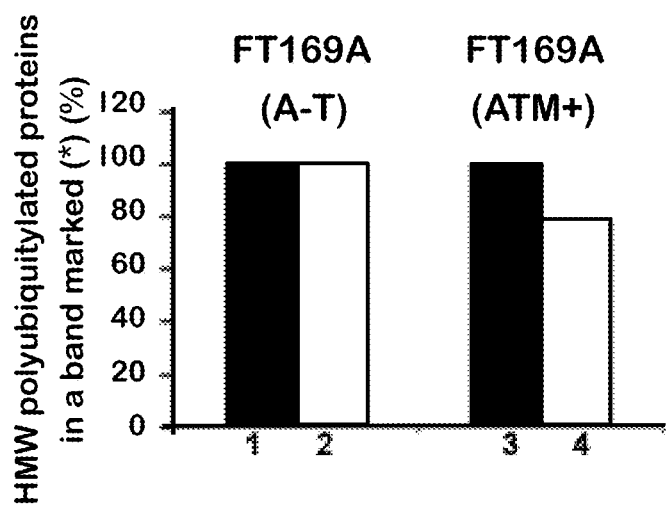

The ubiquitin antibody used in the above experiment is known to cross-react with free, but not conjugated, ISG15/UCRP (44). In order to rule out the possibility that the polyubiquitylated proteins (see species marked by *) identified in FIG. 1A are not due to a cross-reaction with the ISG15 protein and/or other UBL-protein conjugates, HA-tagged ubiquitin cDNA was transfected into FT169A (A-T) and FT169A (ATM+) cells. The amount of polyubiquitylated proteins, and the rate of turnover of these polyubiquitylated proteins (see the HMW protein species marked by ) were then determined under the same conditions as in FIG. 1A, except that anti-HA, rather than an anti-ubiquitin antibody was used in immunoblotting. As shown in FIG. 1B, FT169A (A-T) (lanes 1 and 2) and FT169A (ATM+) (lanes 3 and 4) cells were transfected with HA-ubiquitin as described above in Example 1. Forty-eight hours post-transfection, cells were treated with the protein synthesis inhibitor CHX (marked on top of each lane) for 6 hours. Cell lysates were analyzed using 15% SDS-PAGE followed by immunoblotting with anti-HA antibody. The symbol  marks the position of polyubiquitylated proteins (compressed due to the gel electrophoresis conditions). Quantitation of the high-molecular-weight (HMW) polyubiquitylated proteins (shown as **) is shown in the bar graph.

As shown in FIG. 1B, the amount of HMW HA-ubiquitin-conjugated (polyubiquitylated) proteins (marked by **) was elevated in FT169A (ATM+) as compared to FT169A (A-T) cells (FIG. 1B, compare lanes 1 and 4), consistent with results obtained by measuring the endogenous polyubiquitylated proteins in FT169A (A-T) and FT169A (ATM+) cells shown in FIG. 1A. The difference in the migration of polyubiquitylated proteins seen in FIG. 1A (migrating as a smear * and a compressed band ) and FIG. 1B (migrating as a compressed band ) is due to the different gel systems used in these experiments (5 and 15% discontinuous gel vs. 15% gel respectively). The turnover of HA-ubiquitin-conjugated proteins (species marked by **), measured in the presence of CHX (10 μg/ml) for 6 hours, was negligible in FT169A (A-T) cells (FIG. 1B, compare lanes 1 and 2 and lower panels for quantification). By contrast, a significant amount of HA-ubiquitin-conjugated proteins were degraded in FT169A (ATM+) cells within 6 hours under the same conditions (FIG. 1B, compare lanes 3 and 4 and lower panels for quantification).

Figure 1C:
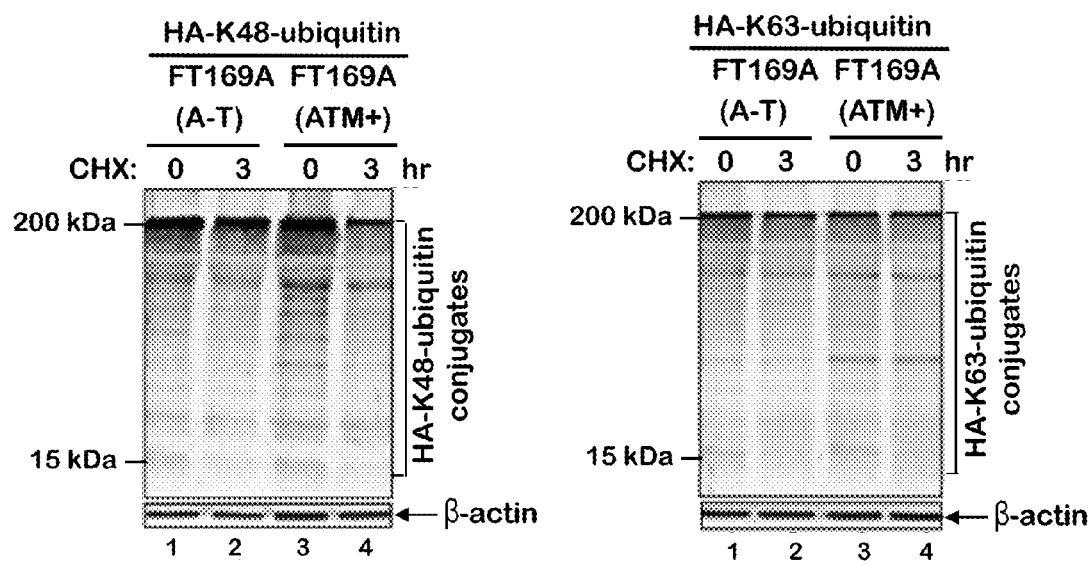
FIG. 1C illustrates A-T and ATM+ cells transfected with HA-Lys48-only (left panel) and Lys63-only (right panel) ubiquitin constructs, then treated with the protein synthesis inhibitor CHX (marked on the top of each lane) for 3 hours, and analyzed by immunoblotting with anti-HA antibodies. The HA-K48-ubiquitin conjugates (left panel) and HA-K63-ubiquitin conjugates (right pane) are shown. All the experiments were repeated at least three times and the representative experiments are shown.
Figure 1D:
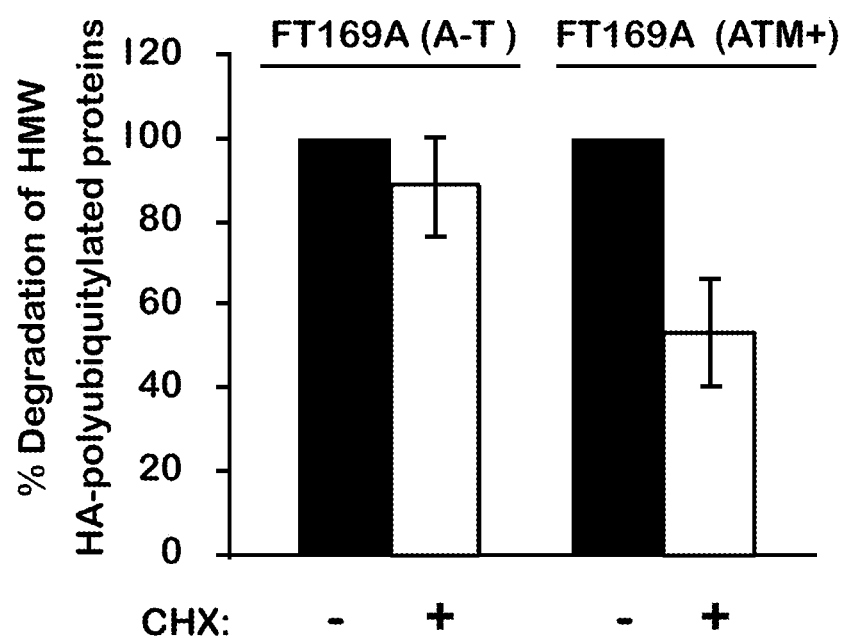
FIG. 1D illustrates A-T and ATM+ cells transfected with HA-ubiquitin, and treated with the protein synthesis inhibitor CHX for 6 hours and then analyzed by immunoblotting with anti-HA antibodies, and the value is the average rate of degradation of high molecular weight (HMW) HA-polyubiquitylated proteins (error bar represents S.E.M.) in A-T and ATM+ cells measured using the Kodak image station 2000R from three independent experiments.

For FIG. 1D, FT169A (A-T) and FT169A cells were transfected with HA-ubiquitin as described above. Forty-eight hours post-transfection, cells were treated with the protein synthesis inhibitor CHX for 6 hours and then analyzed by immunoblotting with anti-HA antibodies. The high molecular weight HA-polyubiquitylated proteins (in 200 kDa compressed band (see band marked as ** in FIG. 1B)) were detected with HA antibodies. Average rate of degradation of high molecular weight (HMW) HA-polyubiquitylated proteins (error bar represents S.E.M.) in FT169A (A-T) and FT169A (ATM+) cells measured using the Kodak image station 2000R from three independent experiments is shown in the bar graph in FIG. 1D.

The same membrane shown in FIG. 1B was stripped and re-probed with anti-ISG15 antibodies. The band intensities of the ISG15 protein remained unaltered in FT169A (A-T) (lanes 1-2) and (ATM+) (lanes 3-4) cells treated with CHX. These results revealed that targeted degradation of the HA-polyubiquitylated proteins is specifically altered in A-T cells. These results obtained with anti-HA-ubiquitin antibody are consistent with results obtained from the use of an anti-ubiquitin antibody (see Western blots (upper panels) and bar graphs showing quantitation of a 200 kDa band (**) (lower panels) comprised of polyubiquitylated proteins in FIGS. 1A, 1B and 1D), suggesting that ATM regulates both the amount and the rate of degradation of polyubiquitylated proteins.

The ubiquitin sequence contains seven lysine residues (at positions 6, 11, 27, 29, 33, 48, and 63) and polyubiquitin chain assembly can occur at any of these lysine residues (74). Lys48-linked polyubiquitylated proteins are targeted for destruction via the 26S proteasome (74). On the other hand, a protein modification with Lys63-linked ubiquitin chains has been implicated in the non-proteolytic regulation of signaling pathways (74). To test if the proteasome-mediated degradation of cellular proteins is impaired in A-T cells, the steady state levels of HA-tagged Lys48- and Lys63-linked polyubiquitylated proteins was examined in FT169A (A-T) and FT169A (ATM+) cells in the presence of CHX. For this purpose, the HA-Lys48-only and HA-Lys63-only constructs were transfected into FT169A (A-T) and FT169A (ATM+) cells. The amount of polyubiquitylated proteins and the rate of turnover of polyubiquitylated proteins (see the HMW protein species marked by *) were determined under the same conditions as in FIG. 1B using the anti-HA antibody in immunoblotting. In FIG. 1C, FT169A (A-T) and FT169A (ATM+) cells were transfected with HA-Lys48-only (left panel) and Lys63-only (right panel) ubiquitin constructs. Thirty hours post-transfection, cells were treated with the protein synthesis inhibitor CHX (marked on the top of each lane) for 3 hours and then analyzed by immunoblotting with anti-HA antibodies as described above. All the experiments were repeated at least three times and representative experiments are shown.

As shown in FIG. 1C, the level of HA-Lys48-linked polyubiquitylated proteins remained relatively unchanged in A-T cells up to three hours in the presence of CHX (FIG. 1C, left panel, compare lanes 1 and 2), suggesting minimal turnover of Lys48-linked polyubiquitylated proteins in A-T cells. On the other hand, the cellular pool of Lys48-linked polyubiquitylated proteins was reduced by more than 70% within 3 hours in FT169A (ATM+) cells under the same conditions (FIG. 1C, left panel, compare lanes 3 and 4). By contrast, the levels of non-proteolytic HA-Lys63-linked polyubiquitylated proteins remained unchanged in both FT169A (A-T) and FT169A (ATM+) cells treated with CHX for 3 hours (FIG. 1C, right panel, compare lanes 1-4). These results suggest that targeted proteasome-mediated degradation of polyubiquitylated proteins is impaired in A-T cells.

Figure 2A:
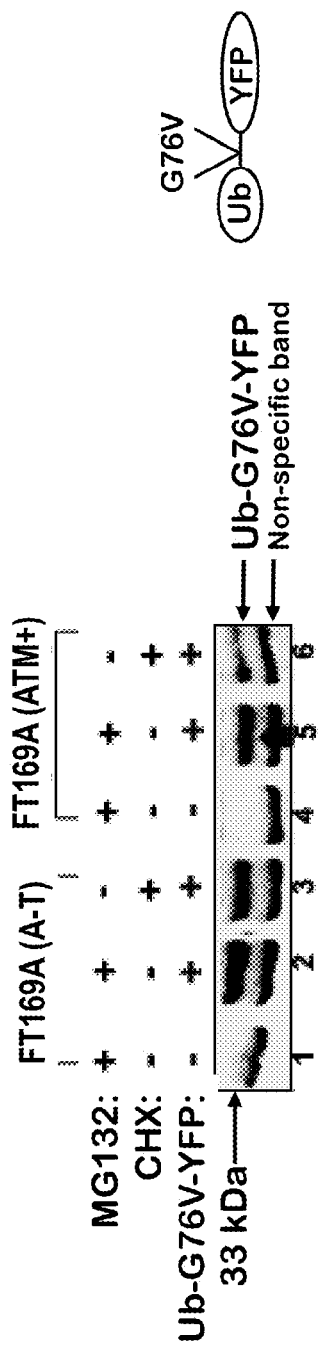
FIGS. 2A and 2B illustrate A-T and ATM+ cells transfected with fluorescent reporter proteasome substrates (the ubiquitin fusion degradation substrate, UbG76V-YFP (FIG. 2A), and the N-end rule substrate, ubiquitin-arginine-YFP (Ub-R-YFP) (FIG. 2B) for 12 hours. Proteasome inhibitor MG132 (0.5 µM) was then added to the transfection medium and cells were allowed to grow for an additional 12 hours. After washing (to remove MG132), cells were treated with protein synthesis inhibitor CHX for 3 hours, and then the fluorescent reporter levels were detected with GFP antibodies.
Figure 2B:
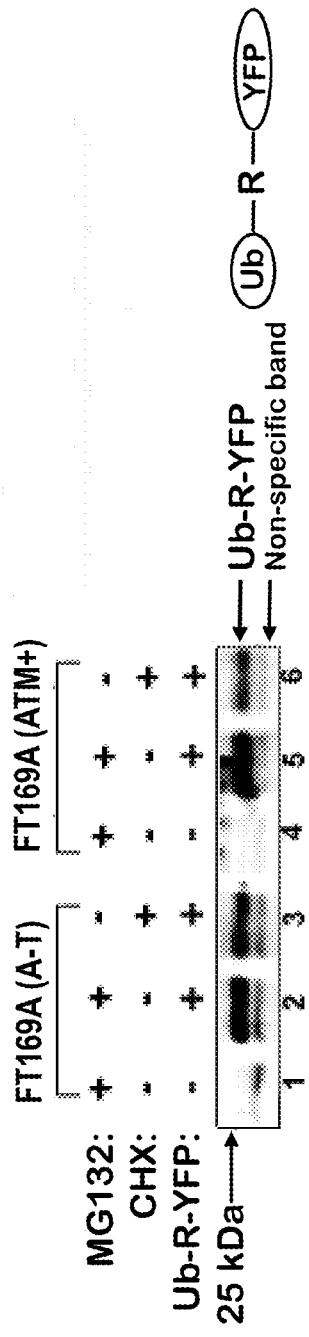

To further determine whether proteasome-mediated degradation of cellular proteins are regulated by ATM, the steady state levels of two fluorescent reporter proteasome substrates (the N-end rule substrate, ubiquitin-arginine-YFP (Ub-R-YFP), and the ubiquitin fusion degradation substrate, UbG76V-YFP (gift from Dr. Nico Dantuma, Karolinska Institutet, Stockholm, Sweden and described previously (75), were measured in FT169A (A-T) and FT169A (ATM+) cells in the presence of CHX. Cells expressing these reporter substrates are known to respond to functional impairment of the ubiquitin/proteasome pathway by accumulation of the readily detectable fluorescent reporter substrate (75). Since these fluorescent substrates are short lived and are degraded rapidly by the proteasome in vivo, cells expressing reporter YFP-substrates were pretreated with the reversible proteasome inhibitor MG132 to enhance their accumulation. After 24 hours, cells were washed to remove MG132-mediated block in proteasome inhibition. The fate of these accumulated YFP-substrates was then monitored in the presence of CHX and in the absence of MG132, and Western blotting using anti-GFP antibodies (YFP differs from GFP due to a mutation at T203Y. Antibodies raised against full-length GFP can therefore detect YFP protein). The results are shown in FIGS. 2A and 2B. FT169A (A-T) and FT169A (ATM+) cells were transfected with fluorescent reporter proteasome substrates (the ubiquitin fusion degradation substrate, UbG76V-YFP (FIG. 2A), and the N-end rule substrate, ubiquitin-arginine-YFP (Ub-R-YFP) (FIG. 2B) for 12 hours. Proteasome inhibitor MG132 (0.5 µM) was then added to the transfection medium and cells were allowed to grow for an additional 12 hours. After washing (to remove MG132), cells were treated with protein synthesis inhibitor CHX (10 µg/ml) for 3 hours. The fluorescent reporter levels were detected with GFP antibodies.

As shown in FIGS. 2A and 2B (lanes 2 and 3), little turnover of both UbG76V-YFP and Ub-R-YFP was observed in FT169A (A-T) cells in the presence of CHX for up to three hours. By contrast, both of these YFP-substrates were rapidly degraded within 3 hours of CHX treatment in FT169A (ATM+) cells (FIGS. 2A and 2B, lanes 5 and 6). Turnover of non-specific bands remained unaltered under the same conditions in both of the cases and served as an internal control.

Figure 2F:
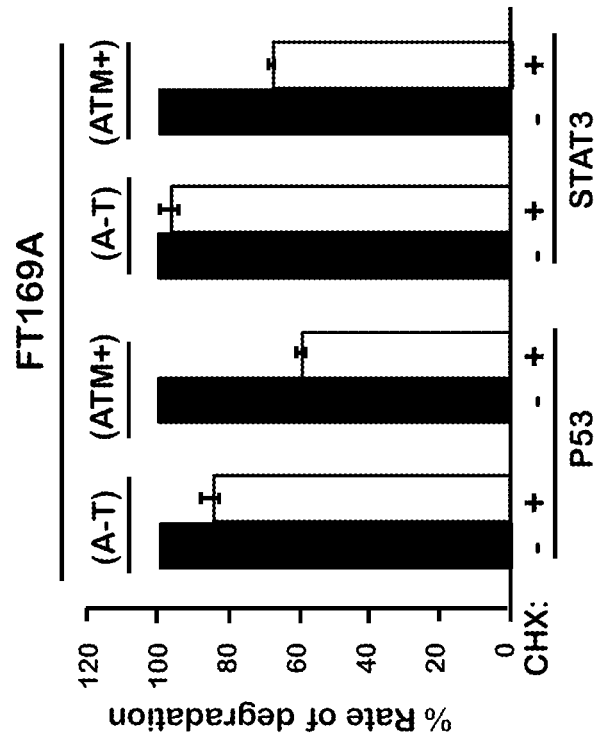
FIG. 2F illustrates A-T and ATM+ cells treated with the protein synthesis inhibitor CHX for 6 h, and the cell lysates were analyzed by immunoblotting using an anti-p53 and/or STAT3 antibody. The average rate of degradation of p53 and STAT3 proteins (error bar represents S.E.M.) in A-T and ATM+ cells were measured using the Kodak image station 2000R, and the results from three independent experiments is shown in the bar graph.
Figure 2E:
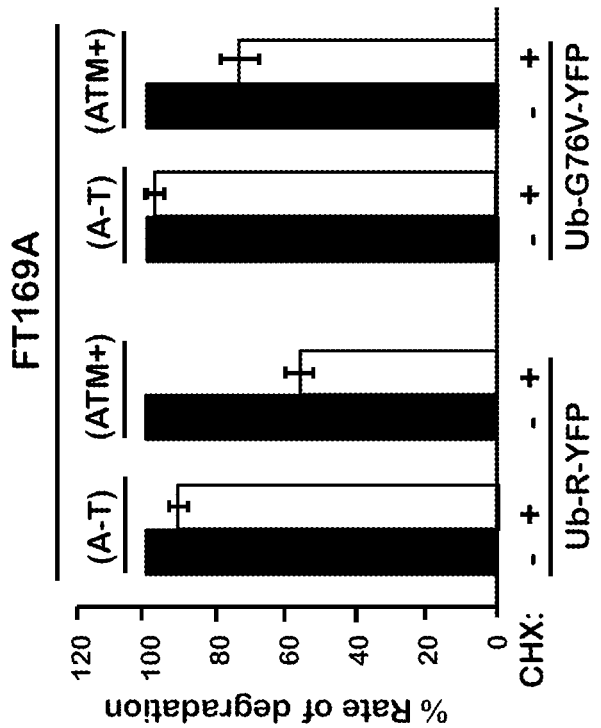
FIG. 2E illustrates A-T and ATM+ transfected with fluorescent reporter proteasome substrates (the ubiquitin fusion degradation substrate, UbG76V-YFP, and the N-end rule substrate, ubiquitin-arginine-YFP (Ub-R-YFP) for 12 h, then treated with the proteasome inhibitor MG132, and cells were allowed to grow for an additional 12 h. After washing (to remove MG132), cells were treated with protein synthesis inhibitor CHX for 3 h, and then the fluorescent reporter levels were detected with GFP antibodies. Average rate of degradation of Ub-G76V-YFP and Ub-R-YFP proteins (error bar represents S.E.M.) in FT169A (A-T) and FT169A (ATM+) cells were measured using the Kodak image station 2000R from three independent experiments, and the results shown in the bar graph.

In FIG. 2E, FT169A (A-T) and FT169A (ATM+) cells were transfected with fluorescent reporter proteasome substrates (the ubiquitin fusion degradation substrate, UbG76V-YFP, and the N-end rule substrate, ubiquitin-arginine-YFP (Ub-R-YFP) for 12 hours. Proteasome inhibitor MG132 (0.5 µM) was then added to the transfection medium and cells were allowed to grow for an additional 12 hours. After washing (to remove MG132), cells were treated with protein synthesis inhibitor CHX (10 µg/ml) for three hours. The fluorescent reporter levels were detected with GFP antibodies. The average rate of degradation of Ub-G76V-YFP and Ub-R-YFP proteins (error bar represents S.E.M.) in FT169A (A-T) and FT169A (ATM+) cells were measured using the Kodak image station 2000R. Results from three independent experiments are shown in FIG. 2E.

Both p53 and STAT3 are known targets of the ubiquitin/26S proteasome pathway. To determine whether steady state level of these proteins is regulated by ATM, turnover of both p53 and STAT3 were measured. In FIG. 2C, FT169A (A-T) and FT169A (ATM+) cells were treated with the protein synthesis inhibitor CHX (10 µg/ml) in the presence (lanes 3 and 6) or absence (lanes 2 and 5) of the proteasome inhibitor MG132 (10 µM) for 6 hours. Cell lysates were analyzed by immunoblotting using an anti-p53 antibody (upper row). The intensity of the p53 bands was measured using a Kodak Image station 2000R (BioRad). Results are shown in the bar graph (right panel). The filter used for immunoblotting was stained with Ponceau S to assure equal protein loading (lower row). As shown in FIG. 2 C (upper row, lanes 1 and 2), little turnover of p53 was observed in FT169A (A-T) cells in the presence of CHX for up to six hours. By contrast, p53 protein was rapidly degraded within 6 hours of CHX treatment in FT169A (ATM+) cells (FIG. 2C, lanes 4 and 5, and bar graph for p53 band quantization). The turnover of p53 in the presence of CHX was blocked by the proteasome inhibitor MG132 (10 µM), indicating that p53 turnover was mediated by the 26S proteasome (FIG. 2C, compare lanes 5 and 6) in ATM+ cells.

In FIG. 2D, FT169A (A-T) (lanes 1-3) and FT169A (ATM+) (lanes 4-6) cells were treated with the protein synthesis inhibitor CHX (10 µg/ml) in the presence (lanes 3 and 6) or absence (lanes 2 and 5) of the proteasome inhibitor MG132 (10 µM) for 6 hours. Cell lysates were analyzed by immunoblotting using an anti-STAT3 antibody as described above. Intensity of the STAT3 band was measured using Kodak Image station 2000R (BioRad). Results are shown in the bar graph (right panel). The lower portion of the same membrane filter was immunostained with the anti-tubulin (lower row) antibody. All of the experiments were repeated at least three times and the representative experiments are shown.

In FIG. 2F, FT169A (A-T) and FT169A (ATM+) cells were treated with the protein synthesis inhibitor CHX (10 µg/ml) for 6 hours. Cell lysates were analyzed by immunoblotting using an anti-p53 and/or STAT3 antibody. An average rate of degradation of p53 and STAT3 proteins (error bar represents S.E.M.) in FT169A (A-T) and FT169A (ATM+) cells were measured using the Kodak image station 2000R. The results from three independent experiments are shown in FIG. 2F. These results indicate that targeted proteasome-mediated degradation of the proteasome substrates, in this case the artificial proteasome substrates, is impaired in A-T cells. FIG. 2F shows the average (+/−SEM) rate of degradation of p53 and STAT3 proteins in FT169A (A-T) and (ATM+) cells from three independent experiments. These results indicate that ubiquitin/26S proteasome pathway is impaired in A-T cells. This is the first time that the ubiquitin/26S proteasome pathway was shown to be impaired in A-T cells.

Example 3

ATM Negatively Regulates the ISG15 Pathway.

Figure 3A:
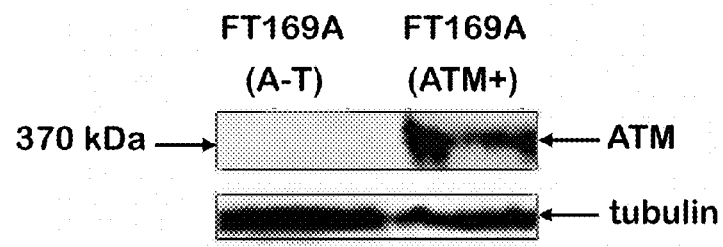
FIGS. 3A-3C illustrate extracts from A-T and ATM+ cells analyzed by 5% (FIG. 3A) or 15% (FIG. 3B) SDS-PAGE, followed by immunoblotting using either anti-ATM (FIG. 3A) or anti-ISG15 antibody (FIG. 3B). The same membranes shown in FIGS. 3A and 3B were stripped and re-probed with anti-tubulin antibody to assure equal protein loading. Average band intensity of the free ISG15 protein (error bar represents SEM) from three independent experiments was quantified using Kodak Image Station 2000R, and the results are shown in the bar graph in FIG. 3C.
Figure 3B:
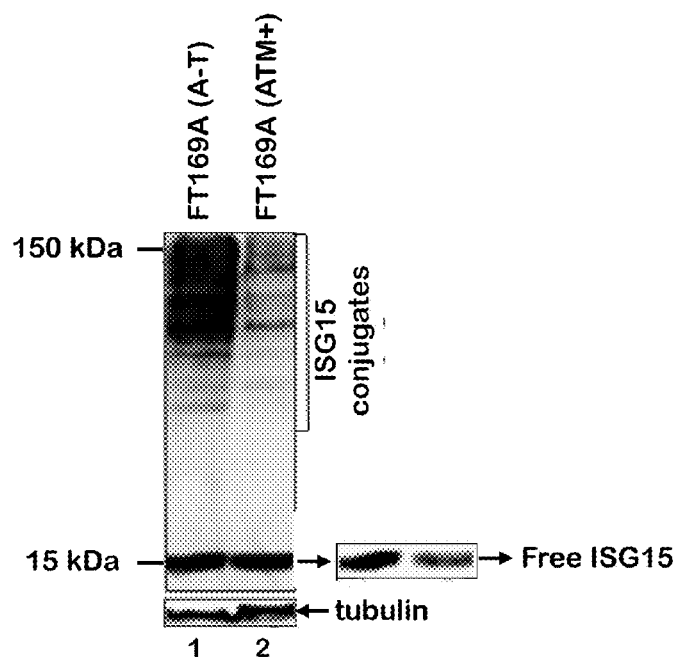
Figure 3C:
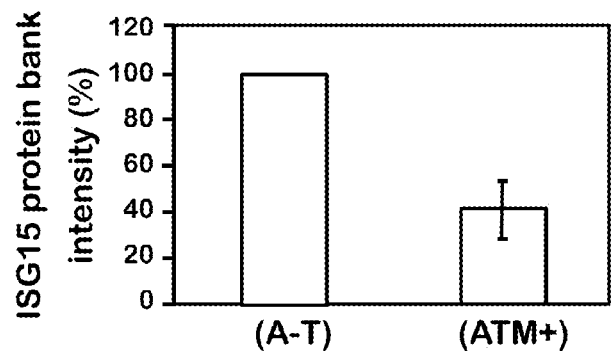

Previous studies have shown that ISG15 is increased in A-T lymphoblasts (70). Overexpression of ISG15 in tumor cells has been linked to reduced protein polyubiquitylation and turnover (24). To determine whether overexpression of the ISG15 pathway is responsible for reduced protein polyubiquitylation in FT169A (A-T) cells as shown above, the levels of ISG15 and its conjugates were measured in ATM null FT169A (A-T) and ATM-reconstituted FT169A (ATM+) cells using anti-ISG15 antibodies by Western analysis. In FIGS. 3A-3C, extracts of FT169A (A-T) and FT169A (ATM+) cells were analyzed by 5% (FIG. 3A) or 15% (FIG. 3B) SDS-PAGE, followed by immunoblotting using either anti-ATM (FIG. 3A) or anti-ISG15 antibody (FIG. 3B). The same membrane shown in FIG. 3B was stripped and re-probed with anti-tubulin antibody to assure equal protein loading. The average band intensity of the free ISG15 protein (error bar represents SEM) from three independent experiments was quantified using Kodak Image Station 2000R, and the results are shown in FIG. 3C.

As shown in FIG. 3A, no detectable ATM protein is present in FT169A (A-T) fibroblast cells. By contrast, ATM protein is readily detected in their corresponding wild type cells (i.e. FT169A (ATM+) cells). The levels of both free ISG15 and ISG15 conjugates were significantly higher in FT169A (A-T) cells than in their corresponding wild type FT169A (ATM+) cells (FIG. 3B). The bar graph in FIG. 3C shows the average (+/−SEM) band intensities of free ISG15 proteins in FT169A (A-T) and (ATM+) cells from three independent experiments.

These results using A-T fibroblast cells indicate that ISG15 is overexpressed in A-T lymphoblast cells. These results, together with results shown in FIGS. 1A-1D and 2A-2F, indicate that overexpression of the ISG15 pathway results in reduced protein polyubiquitylation and turnover of cellular proteins in A-T cells.

Example 4 siRNA-Mediated Knockdown of ISG15 and UbcH8 Increases Protein Polyubiquitylation and Degradation in A-T Cells.

To further determine whether overexpression of ISG15 and its conjugates in A-T cells are responsible for reduced protein polyubiquitylation and turnover, ISG15 and UbcH8 (the cognate E2 for ISG15 conjugation) siRNAs were employed to knockdown the expression of ISG15 and ISG15 conjugates, respectively, in FT169A (A-T) cells. Seventy-two hours after siRNA transfections, cells were further transfected with HA-ubiquitin cDNA for 24 hours.

Figure 4A:
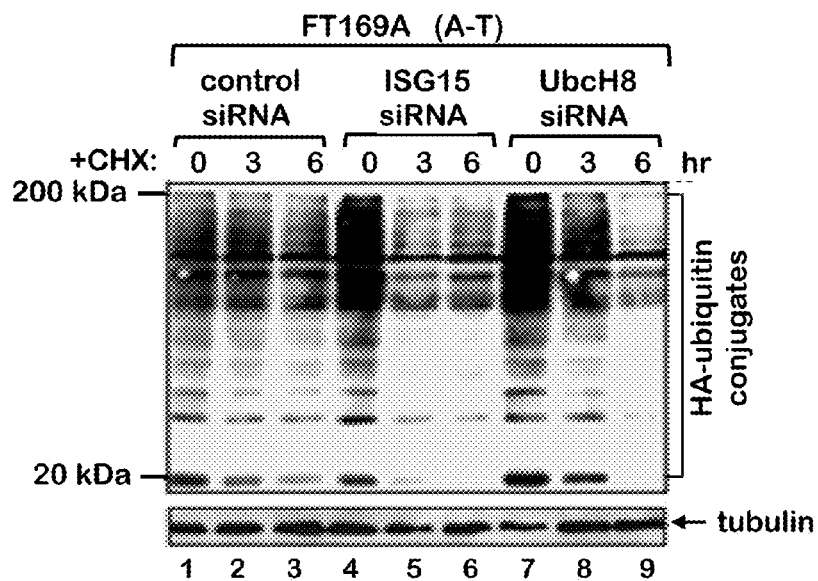
FIGS. 4A-C illustrate A-T cells treated with either control (lanes 1-3), ISG15 (lanes 4-6) or UbcH8 (lanes 7-9) siRNAs for 72 h, followed by transfection with an HA-ubiquitin expression vector for 24 h. Cells were then treated with protein synthesis inhibitor CHX for various times (lanes 2, 3, 5, 6, 8 and 9), and then lysed with 2×SDS gel sample buffer. Cell lysates were analyzed by immunoblotting using anti-HA antibody (FIG. 4A). The same membrane shown in FIG. 4A was stripped and re-probed with anti-tubulin antibody to assure equal protein loading (FIG. 4A, bottom panel). For FIG. 4B, the same samples shown in lanes 1, 4, and 7 were reloaded on a separate gel (15%), followed by immunoblotting using an anti-ISG15 antibody. For FIG. 4C, the same samples shown in lanes 1 and 7 along with purified UbcH8 enzyme were reloaded on a separate gel (15%), followed by immunoblotting using the anti-UbcH8 antibody.

In FIG. 4A, FT169A (A-T) cells were treated with either control (lanes 1-3), ISG15 (lanes 4-6) or UbcH8 (lanes 7-9) siRNAs for 72 hours followed by transfection with an HA-ubiquitin expression vector for 24 hours. Cells were treated with protein synthesis inhibitor CHX (10 µg/ml) for various times (lanes 2, 3, 5, 6, 8 and 9). Cells were then lysed with 2×SDS gel sample buffer. Cell lysates were then analyzed by immunoblotting using anti-HA antibody (FIG. 4A). The same membrane shown in FIG. 4A was stripped and re-probed with anti-tubulin antibody to assure equal protein loading (FIG. 4A, lower panel). The average rate of degradation of HA-polyubiquitylated proteins (error bar represents S.E.M.) in ISG15 or UbcH8 siRNA treated FT169A (A-T) cells measured using the Kodak image station 2000R from three independent experiments is shown in the bar graph presented in FIG. 4G.

Figure 4B:
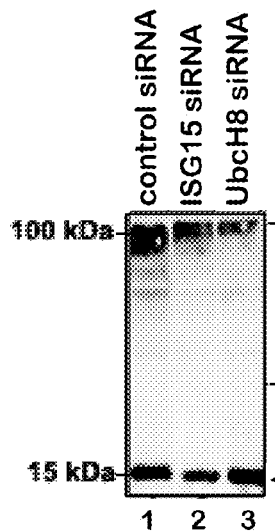
Figure 4C:
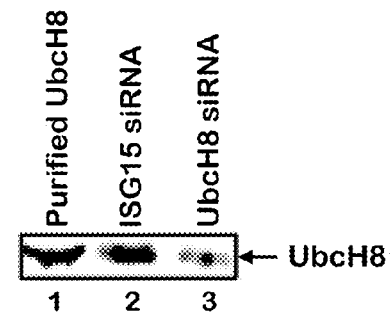

The same samples shown in lanes 1, 4, and 7 of FIG. 4A were reloaded on a separate gel (15%), followed by immunoblotting using an anti-ISG15 antibody, and the results presented in FIG. 4B. The same samples shown in lanes 1 and 7, FIG. 4A, along with purified UbcH8 enzyme were reloaded on a separate gel (15%), followed by immunoblotting using the anti-UbcH8 antibody, and the results shown in FIG. 4C.

Figure 4D:
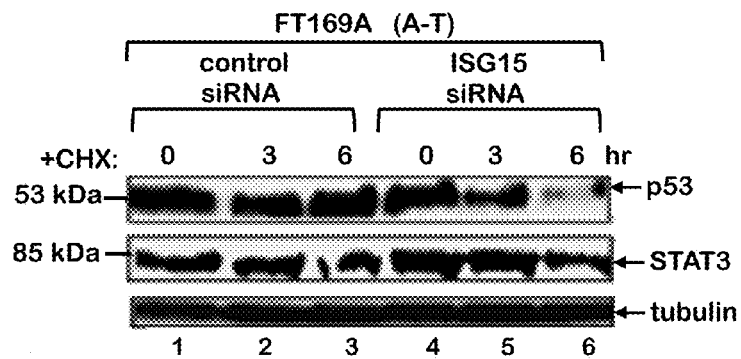
FIGS. 4D-4F illustrate A-T cells transfected with ISG15 siRNA for 72 h, and then treated with the protein synthesis inhibitor CHX for 3 and 6 h. Cell lysates were then analyzed by immunoblotting using anti-p53 (top panel), anti-STAT3 (middle panel) or anti-tubulin (lower panel) antibodies as shown in FIG. 4D. The p53 and STAT3 bands shown in the first and second panels were quantified using the Kodak Image Station 2000R, and the results shown in FIGS. 4E (p53) and 4F (STAT3). All the experiments were repeated at least three times.
Figure 4E:
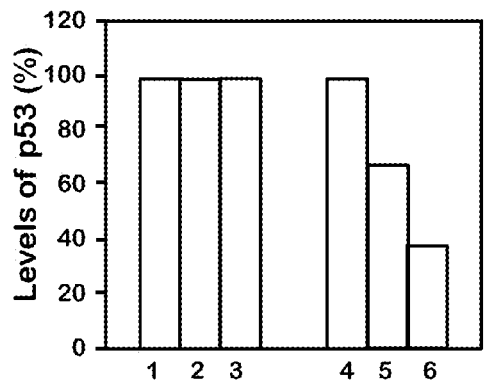
Figure 4F:
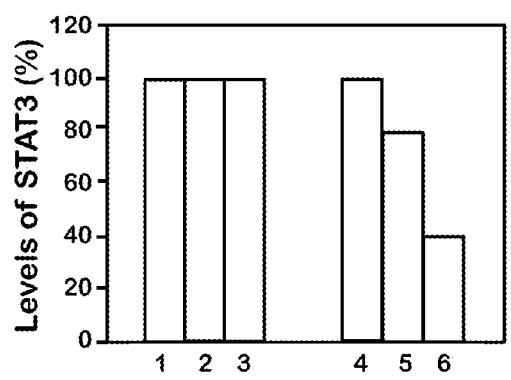
Figure 4G:
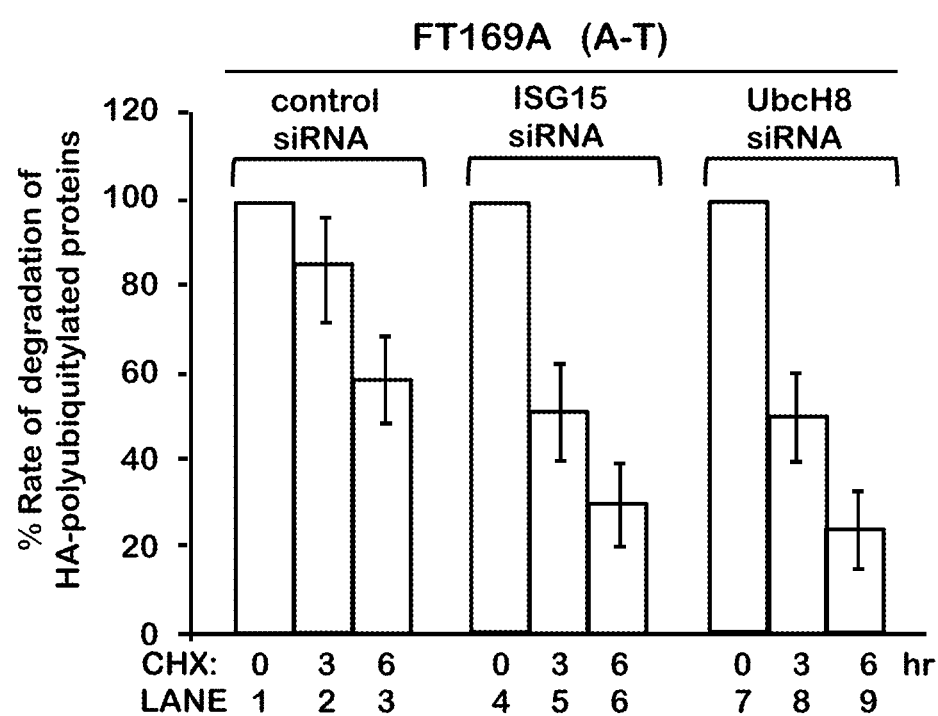
FIG. 4G illustrates A-T cells transfected with ISG15 or UbcH8 siRNA for 72 h, and then treated with the protein synthesis inhibitor CHX for 3 and 6 h. Cell lysates were analyzed by immunoblotting using anti-HA antibodies. The average rate of degradation of HA-polyubiquitylated proteins (error bar represents S.E.M.) in ISG15 or UbcH8 siRNA treated A-T cells measured using the Kodak image station 2000R from three independent experiments is shown in FIG. 4G.

In FIG. 4D, FT169A (A-T) cells were transfected with ISG15 siRNA for 72 hours. Cells were then treated with the protein synthesis inhibitor CHX (10 µg/ml) for 3 and 6 hours. Cell lysates were then analyzed by immunoblotting using anti-p53 (top panel), anti-STAT3 (middle panel) or anti-tubulin (lower panel) antibodies. The p53 and STAT3 bands shown in the first and second panels were quantified using the Kodak Image Station 2000R, and the quantification for p53 and STAT3 is shown in FIGS. 4E and 4F, respectively. All the experiments were repeated at least three times and the representative experiments are shown.

ISG15 siRNA significantly reduced ISG15 expression (70% decrease in the ISG15 band intensity) as revealed by immunoblotting using anti-ISG15 antibody (FIG. 4B, compare lanes 1 and 2). UbcH8 siRNA, on the other hand, significantly reduced the amount of ISG15-protein conjugates without affecting the expression level of free ISG15, as revealed by immunoblotting using anti-ISG15 antibody (FIG. 4B, compare lanes 2 and 3). Western blotting analysis of FT169A (A-T) cells transfected with UbcH8 siRNA showed that the expression level of UbcH8 was reduced by 70% (as judged by the decrease in the UbcH8 band intensity) as compared to FT169A (A-T) cells transfected with control siRNA (FIG. 4C). By contrast, under the same conditions, the amount of HA-ubiquitylated HMW proteins (reflecting polyubiquitylated proteins), revealed by immunoblotting with anti-HA antibodies, was greatly increased in cells treated with either ISG15 or UbcH8 siRNA than in cells treated with control siRNA (FIG. 4A, compare lane 1 with lanes 4 and 7). The turnover of polyubiquitylated proteins was then measured in the presence of CHX (see FIG. 4A). As shown in FIG. 4A, the turnover of HA-ubiquitin-conjugated proteins was negligible in FT169A (A-T) cells (overexpressing ISG15) treated with CHX (10 µg/ml) for 6 hours (compare lanes 1 and 3). By contrast, about two thirds of HA-ubiquitin-conjugated proteins were degraded in FT169A (A-T) cells transfected with either ISG15-specific (FIG. 4A, compare lanes 4 and 6) or UbcH8-specific siRNA (FIG. 4A, compare lanes 7 and 9) within 6 hours under the same conditions. The same membrane filter as shown in FIG. 4A was stripped and re-probed with anti-tubulin to assure equal protein loading (FIG. 4A, lower panel). The turnover of p53 and STAT3, which is reduced in FT169A (A-T) cells transfected with control siRNA, was shown to be restored in FT169A (A-T) cells transfected with ISG15 siRNA (FIG. 4D first and second panel, and FIGS. 4E and 4F for quantitation). These results indicated that protein ISGylation results in reduced protein polyubiquitylation and turnover of cellular proteins in A-T cells. It is also possible that the free ISG15 pool plays an independent role in regulating protein polyubiquitylation and turnover in A-T cells.

Example 5

Expression of ISG15 and its Conjugates is Elevated in Cells Deficient in ATM.

Figure 5:
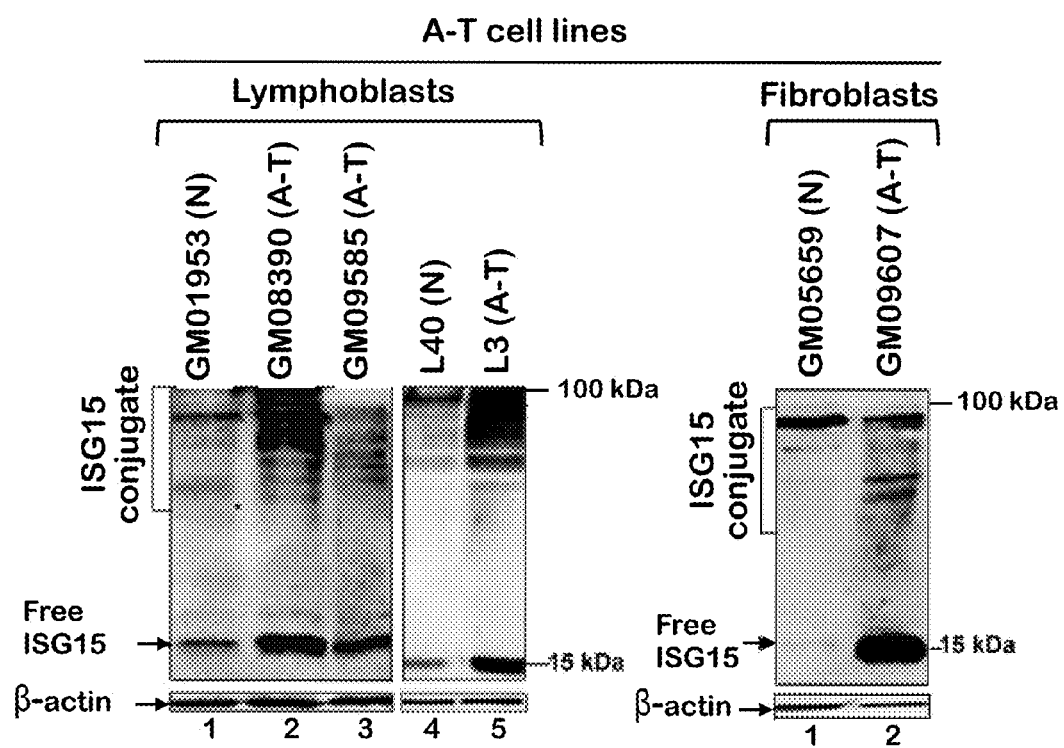
FIG. 5 illustrates normal (N) and Ataxia Telangiectasia (A-T) lymphoblast (left panel) and fibroblast (right panel) cell lysates analyzed by 15% SDS-PAGE, followed by immunoblotting using anti-ISG15 antibody (upper panels). The same membrane shown in the upper panels was stripped and re-probed using anti-β-actin antibody (lower panels). The experiment was repeated at least three times, and a representative experiment is shown.

The levels of ISG15 and its conjugates were measured in several other lymphoblast and fibroblast cell lines derived from A-T patients (A-T) and normal individuals (N). In FIG. 5, Normal (N) and Ataxia Telangiectasia (A-T) lymphoblast (left panel) and fibroblast (right panel) cells were analyzed by 15% SDS-PAGE, followed by immunoblotting using anti-ISG15 antibody (upper panels). The same membrane shown in the upper panels was stripped and re-probed using anti-β-actin antibody (lower panels). The experiment was repeated at least three times and the representative experiment is shown.

As shown in FIG. 5, the levels of ISG15 and its conjugates as measured by immunoblotting using anti-ISG15 antibodies were higher in A-T lymphoblast (left panel, lanes 2, 3 and 5) and fibroblast (right panel, lane 2) cells. On the other hand, very little ISG15 expression (free and conjugated form) was seen in both lymphoblast and fibroblast cells derived from normal cells (left panel, lanes 1 and 4, and right panel, lane 1). These results, together with the results shown in FIGS. 3A-3C, strongly suggest that ATM negatively regulates the expression of ISG15 and its conjugates.

Example 6

Expression of ISG15 and its Conjugates is Elevated in Brains of ATM Knockout Mice and A-T Human Patients.

Figure 6A:
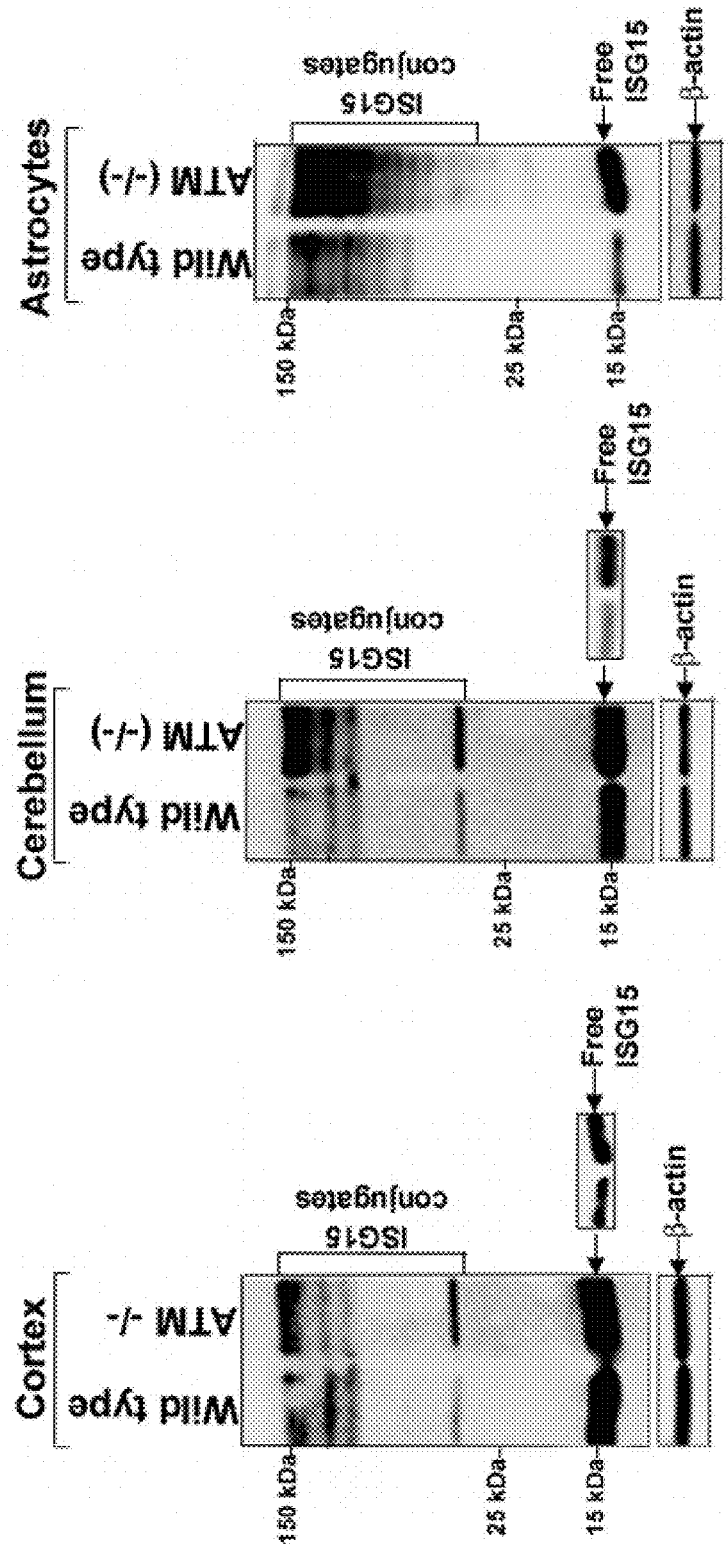
FIG. 6A illustrate lysates from cortex (left panel) and cerebellum (middle panel) tissues, as well as primary cortical astrocytes (right panel), from brains of ATM knockout mice immunoblotted using anti-ISG15 antibodies. All membrane filters were immunostained with anti-tubulin antibody (lower panels). The brain tissue lysates of two animals were pooled and loaded on SDS-PAGE. The experiment was repeated twice with reproducible results.

The results from Examples 2-4 indicate that the ISG15-mediated impairment of protein degradation in A-T neurons could be the basis of the progressive neurodegeneration in A-T patients. To test whether ISG15 expression is elevated in vivo, the expression of ISG15 and its conjugates was assessed in various regions of brain tissues obtained from wild type and ATM knockout mice. In FIG. 6A, lysates from cortex (left panel), cerebellum (middle panel) tissues, and primary cortical astrocytes (right panel), were immunoblotted using anti-ISG15 antibodies as described in Example 1. All membrane filters were immunostained with anti-tubulin antibody (lower panels). The brain tissue lysates of two animals were pooled and loaded on SDS-PAGE. The experiment was repeated two times with reproducible results.

The levels of free ISG15 (see inserts showing lower exposure) and its conjugates were increased in the cortex (FIG. 6A, first panel) and cerebellum (FIG. 6A, second panel) isolated from ATM knockout as compared to wild-type mice. In addition, ATM knockout astrocytes exhibited a striking increase in ISG15 and its conjugates over that from astrocytes derived from wild-type mice (FIG. 6A, third panel).

Figure 6B:
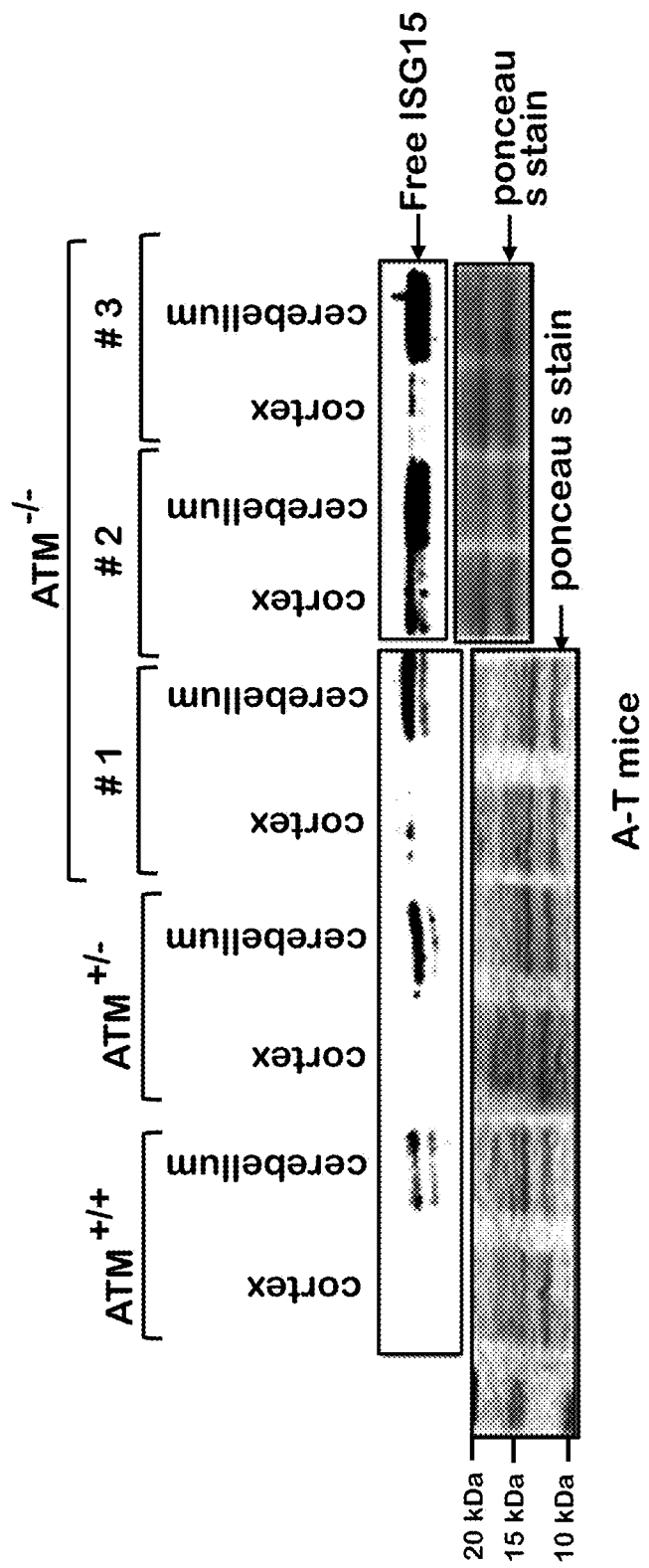
FIG. 6B illustrates lysates from specific brain regions isolated from Atm+ and Atm+/− mice immunoblotted using anti-ISG15 antibodies, and using Ponceau's stain to indicate equal protein loading.

ISG15 was also shown to be elevated in the murine $Atm^+$ and $Atm^{-/-}$ cerebellum, the specific brain region affected by A-T disease. Brains from the two strains of mice were assessed as described above, and the results shown in FIG. 6B. Very little expression of ISG15 was seen in the cortex.

Figure 7A:
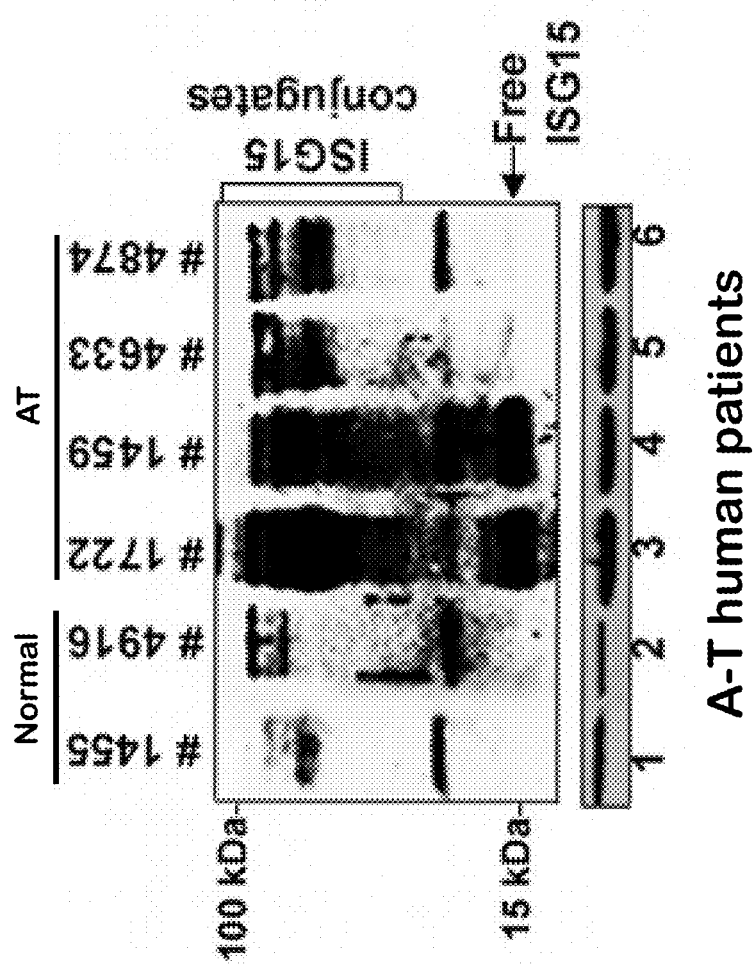
FIG. 7A illustrates frozen mid-brain postmortem tissues from two normal individual (UMB#1455 and 4916) and four A-T patients (UMB #s 1722, 1459, 4663 and 4874), after weighing and sonicating in a SDS sample buffer, and analyzed using anti-ISG15 antibodies. As a loading control, lysates were also immunoblotted against β-actin.

To further examine if ISG15 expression is elevated in vivo, mid-brain regions (specifically containing substantia nigra) obtained postmortem from four different A-T human patients (with confirmed A-T disease (UMB#s 1722, 1459, 4663, and 4874)) and two control individuals (without any disease (UMB#s 1455 and 4916)) were assessed for ISG15 expression by Western blotting using anti-ISG15 antibodies. In FIG. 7A, frozen mid-brain postmortem tissues from two normal individuals (UMB#1455 and 4916) and four A-T patients (UMB #s 1722, 1459, 4663 and 4874) were weighed and sonicated in a SDS sample buffer. Sonicated samples were immediately boiled for 10 min at 100° C. and centrifuged at 13,000×g for 10 min. Cleared supernatants were analyzed using anti-ISG15 antibodies. As a loading control, lysates were also immunoblotted against β-actin.

As shown in FIG. 7 A, ISG15 and its conjugates were highly elevated in two A-T patients (lanes 3 and 4), and moderately elevated in two other A-T patients (lanes 5 and 6). On the other hand, ISG15 expression was modest in brain tissue obtained from normal individuals (lanes 1 and 2).

A double immunofluorescence analysis was performed on the mid-brain tissue sections (containing specifically substantia nigra) obtained from a normal individual (UMB#1455) and A-T patients (UMB#1722, #4663, and #4874) shown in FIG. 7A, using ISG15 (green) and Lys63-linkage-specific polyubiquitin (red) antibodies (FIG. 7B). In FIG. 7B, the deparaffinized human brain tissue sections from the normal subject (UMB#1455) and A-T patients (UMB#1722, 4663) described in FIG. 7A. were double stained with anti-ISG15 (polyclonal) and anti-K63-linkage specific polyubiquitin (monoclonal) (1:100) antibodies. After washing with PBS, sections were stained with Alexa Fluor 488 goat anti-rabbit IgG secondary antibody to detect ISG15 (green) and goat polyclonal secondary antibody to mouse IgG (Cy5®) to detect Lys63-linked polyubiquitin conjugated proteins (red). Sections were mounted in gold antifade mounting medium and examined using Nikon E600 epifluorescence microscope (Nikon) (20× magnification, scale bar, 100 um). One slide each of the deparaffinized human brain tissue sections of A-T patients and normal individuals (obtained from the NICHD Brain and Tissue Bank for Developmental Disorders at the University of Maryland) was used in the experiment. Arrows indicate ubiquitin/ISG15 double-positive inclusions in the merged A-T brain sections.

As shown in FIG. 7 B, the dramatic increase in both ubiquitin/ISG15 double-positive inclusions (see arrows in merged images) was found in the mid-brain sections obtained from all three A-T patients tested. In contrast, no such inclusions were found in brain sections of the normal individual. An immunofluorescence study was also performed on the mid-brain section obtained from another normal subject (UMB#4669); consistent with the results similar to that shown in FIG. 7B for normal subject UMB#1455; i.e., no ISG15 containing inclusion bodies were found in the brain sections obtained from this normal individual using ISG15-specific antibodies (results not shown). The presence of ISG15/Lys63-linkage specific polyubiquitin containing inclusion bodies in the A-T patient's brain sections further indicates the involvement of a defective ubiquitin-proteasome system in A-T neurodegeneration.

Part B: ISG15 Deregulates Autophagy in Genotoxin-Treated Ataxia Telangiectasia Cells Example 7

Materials and Methods

Cells: FT169A (A-T) and FT169A (ATM+) fibroblast cells were obtained from Dr. Y. Shiloh at Tel Aviv University, Ramat Aviv, Israel. FT169A (A-T) cells were derived from FT169A cells (ATM null) by stable transfection with the expression vector alone as previously described (39). FT169A (ATM+) cells were derived from FT169A cells by stable transfection with full-length ATM cDNA (39). Both FT169A (A-T) and (ATM+) fibroblast cells were cultured in complete DMEM (Cellgro) supplemented with hygromycin B (100 µg/ml) (Cellgro).

Human Tissues. Human brain tissues and tissue sections were obtained from the NICHD Brain and Tissue Bank for Developmental Disorders at the University of Maryland (supported by NICHD contract # N01-HD-4-3368 and N01-HD-4-3383) under ethics protocols approved by the University of Maryland Institutional Review Board. Frozen human mid-brain tissues containing specifically substantia nigra were obtained postmortem from patients with confirmed A-T disease and control individuals (without any known disease). Slides with paraffin-embedded sections of the midbrain tissues were used in immunofluorescence study.

Construction of lentiviral ISG15 shRNA stable transfectants of FT169A (A-T) cell: Preparation of lentiviral particles was done as described (40). Briefly, five shRNA constructs (TRCN0000007420-5) for the ISG15 in a pLKO1 vector and one control non-targeting shRNA lentiviral vector (SHC002V) were purchased from Sigma-Aldrich. Amongst the five shRNA constructs tested, TRCN0000007422 NM_005101.1-295S1C1 shRNA that showed efficient ISG15 knocked-down (>75%) in FT169A cells was used for the production of lentiviral particles. Lentiviral particles were generated by transfecting HEK293T cells with the lentiviral shRNA vector (pLKO.1-Puro harboring ISG15 or SHC002V vector harboring control shRNA), together with the packaging (psPax2) and an envelope (pMD2.G) vector (Addgene; Cambridge, Mass.) using standard calcium phosphate precipitation as described (41). Six to eight hours post-transfections, cells were washed once and replenished with the fresh DMEM medium, and allowed to grow for additional 48 hrs. The viral supernatants were then harvested and filtered through a 0.45-µm pore size filter. For transduction, FT169A (A-T) cells (65,000 cells/ml) were plated in a 6 well tissue culture plate 24 h prior to the lentiviral infection. The next day, culture medium was replaced with the 1 ml of fresh medium containing 6.5 µg/ml of polybrene (Chemicon International; Temecula, Calif.). Cells were infected with lentiviral particles containing ISG15 or control shRNA and incubated in a tissue culture incubator overnight. After 12 h of incubation, all transduced cells were replenished with the fresh culture media without polybrene. Two days post-transduction, cells were split (1:5)

and allowed to grow under normal conditions (37° C. and 5% $CO_2$). Selection medium that contained 6.5 µg/ml puromycin dihydrochloride (Sigma-Aldrich) was then added to the cells 48 h after replating. Individual colonies were picked following 5 weeks of puromycin selection and screened for ISG15 expression by Western blotting analysis using anti-ISG15 antisera.

Immunoblotting and immunofluorescence analysis: Immunoblotting analysis of proteins in cultured cells: Cells (5×105) were cultured in 35 mm tissue culture plates. After various experimental treatments, cells were lysed using a SDS-PAGE sample buffer. Cell lysates were then analyzed by SDS-PAGE (10% for p62 or 15% for LC3 and polyubiquitin conjugates) and immunoblotting analysis using either anti-ISG15 (raised against human ISG15 (23)), anti-ubiquitin (Sigma-Aldrich), anti-HA (gift from Dr. Walworth at Robert Wood Johnson Medical School/University of Medicine and Dentistry of New Jersey; Piscataway, N.J.)), anti-LC3 (MBL International Corporation; Woburn, Mass.), or p62 (Sigma-Aldrich) antibodies, as indicated, using the ECL Western procedure (Pierce) and the BioRad VersaDoc Imaging System.

Immunoblotting Analysis of HA-ubiquitin conjugated proteins in cells exposed to UV radiation. Cells (5×105) were transfected with a hemagglutinin (HA)-ubiquitin plasmid using the PolyFect transfection reagent (Qiagen; Valencia, Calif.) as described (24). Twenty-four h after transfection, cells were treated with either proteasome inhibitor MG132 (1 µM) (Boston Biochemicals; Cambridge, Mass.) or autophagy inhibitor Bafilomycin A1 (Bafl) (1 nM) (Sigma-Aldrich) or 3-Methyladenine (3-MA) (100 nM) for 18 h. Cells were exposed to UV radiation (25 mJoules, using BioRad GS Gene Linker™ UV Chamber) and/or left untreated. Cells were then allowed to recover in the presence of inhibitors for 3 hr. Cell lysis, SDS-PAGE, and immunoblotting analysis to detect HA-ubiquitin conjugated proteins using anti-HA antibodies was carried out as described above.

Immunofluorescence analysis in cells: LC3 expression. Cells (100,000/point) were cultured on fibronectin-coated glass coverslips. Next day, cells were fixed in 4% paraformaldehyde. After washing with phosphate-buffered saline (PBS) (2×5 min), cells were incubated with 100 µg/ml Digitonin for 15 min at room temperature. Cells were then washed with PBS (2×5 min) and immunostained for LC3 (MBL International Corporation) for 1 h at room temperature. After washing with phosphate-buffered saline (PBS) (2×5 min), cells were incubated with Alexa-Fluor 488 goat anti-mouse IgG secondary antibody (1:100) (Invitrogen) for 1 h. Cells were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations; Santa Monica, Calif.).

Autophagasome, lysosome and autophagolysosomes staining. Cells (100,000/point) were cultured on fibronectin-coated glass coverslips. Cells were treated with autophagy inhibitor Bafl (1 nM) (Sigma-Aldrich) for 18 hr. Cells were then exposed to UV radiation and allowed to recover in the presence of inhibitors for 3 h. Cells were then washed (2×1 min) with PBS and co-stained with Cyt-ID® (Cyt-ID® Autophagy Detection Kit from Enzo Lifesciences; Farmingdale, N.Y.) and Lyso Tracker® Red DND-99 (Invitrogen) for 30 min at 37° C. in a $CO_2$ incubator following manufacturer's protocol. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations).

Immunoblotting Analysis of LC3 expression in brain tissues of A-T patients by Western blotting. Frozen tissues were stored at −80° C. until use. For detecting LC3, frozen tissues were weighed, cut into small pieces, and placed in test tubes containing SDS sample buffer. Tissue samples were then sonicated with a Tissue-Tearor (Biospec Products, Inc.; Bartlesville, Okla.). Sonicated samples were immediately boiled for 10 minutes at 100° C. and subsequently centrifuged at 13,000×g for 10 min. Cleared supernatants containing SDS-solubilized protein extracts were analyzed by 15% SDS-PAGE and immunoblotted using anti-LC3 as described above.

Immunofluorescence analysis in A-T brain tissue sections. For double immunofluorescence, tissue sections were deparaffinized in xylene and incubated with the GFAP (Abcam) and LC3 (MBL International Corporation) primary antibodies (1:100) for 1 hr. After washing in PBS, sections were stained with Alexa Fluor 488 goat anti-rabbit IgG secondary antibody (Invitrogen) and goat polyclonal secondary antibody to mouse IgG (Cy5 ®) (Abcam). Sections were mounted in gold antifade mounting medium (Invitrogen) and examined using Nikon E600 epifluorescence microscope (Nikon). All the operations were performed at room temperature.

Example 8

Figure 8A:
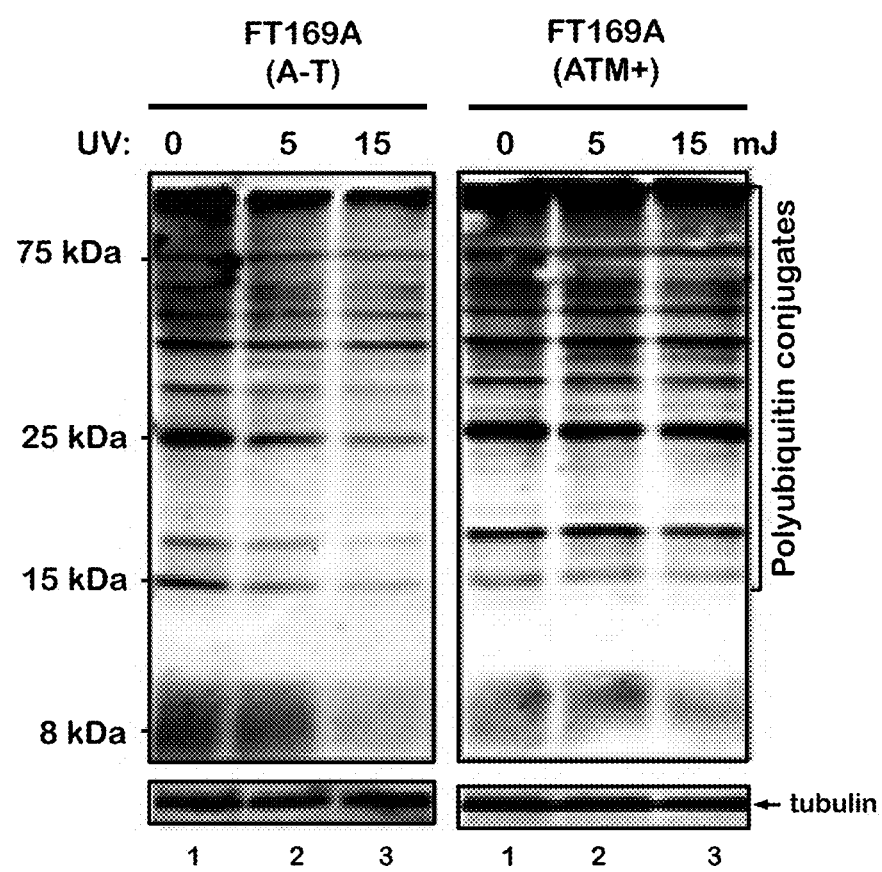
FIG. 8A illustrates A-T and ATM+ cells exposed to different doses of UV and allowed to recover for 3 h. Cells were lysed and lysates were analyzed by Western blotting for polyubiquitylated proteins and tubulin using anti-ubiquitin and anti-tubulin antibodies respectively. The results are shown in FIG. 8A.

UV Induces Degradation of Polyubiquitylated Proteins in A-T but not in ATM+ Cells Previous studies using the FT169A (A-T) (ATM null; henceforth referred to as A-T) and FT169A (ATM+) (ATM reconstituted FT169A; henceforth referred to as ATM+) isogenic pair of fibroblast cells have demonstrated that ISG15, a ubiquitin-like protein known to antagonize the ubiquitin pathway, is elevated and inhibits the ubiquitin pathway in A-T cells (24). The ubiquitin pathway plays a key role in ATM-dependent DNA repair (42). Because A-T cells are defective in both the DNA repair (due to the defective ATM kinase) (43) and ubiquitin (due to the constitutively elevated ISG15 pathway) pathways (20), UV, a genotoxic stressor known to induce DNA damage, was examined for its effect on the global protein polyubiquitylation and their subsequent degradation in A-T cells. In FIG. 8A, A-T and ATM+ cells were exposed to different doses of UV and allowed to recover for three hours. Cells were lysed and lysates were analyzed by Western blotting for polyubiquitylated proteins and tubulin using anti-ubiquitin and anti-tubulin antibodies respectively.

As shown in FIG. 8A, the steady state levels of the endogenous polyubiquitylated proteins and free ubiquitin rapidly decreased in A-T cells exposed to different doses of UV radiation and detected 3 hours post-radiation survival (FIG. 8A, left panel, compare lane 1 with lanes 2 and 3). By contrast, very little decrease in the steady state levels of polyubiquitylated proteins was seen in ATM+ cells under the same conditions (FIG. 8A, right panel, compare lane 1 with lanes 2 and 3). These results reveal that the steady-state levels of polyubiquitylated proteins are decreased in UV-treated A-T but not in ATM+ cells.

Figure 8B:
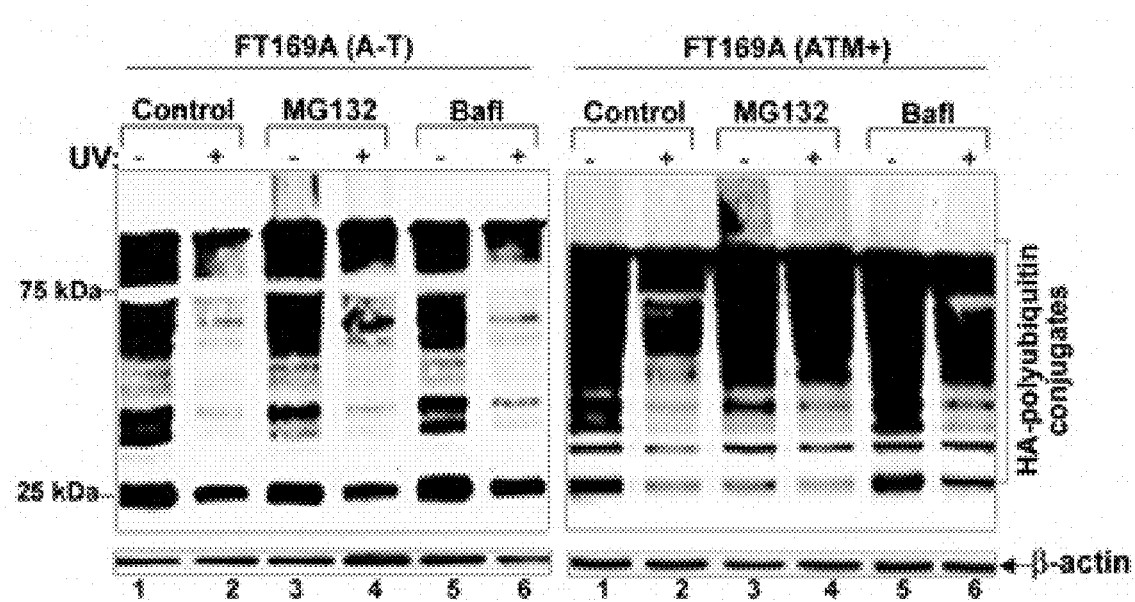
FIGS. 8B-8C illustrate A-T and ATM+ cells transfected with a HA-ubiquitin construct, then treated with MG132 or Bafl for 18 h, and exposed to UV radiation (25 mJ/m2). After recovery in the presence of inhibitors for 3 h, cells were lysed, and the lysates analyzed by Western blotting for HA-polyubiquitylated proteins and actin using anti-HA and anti-actin antibodies respectively. Intensity of the total HA-polyubiquitylated proteins was quantitated using BioRad Quantity One software. The bar graph in FIG. 8C shows average values (±SEM) of % degradation of HA-polyubiquitylated proteins from three independent experiments.
Figure 8C:
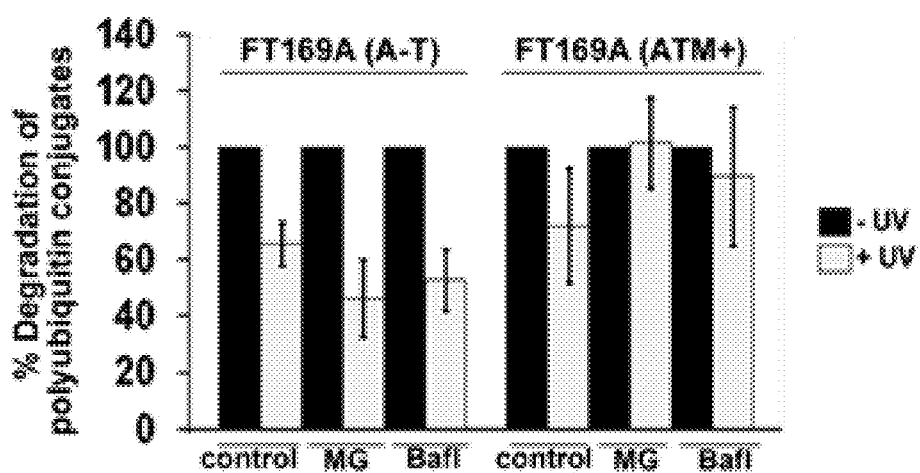

Decrease in the steady state levels of polyubiquitylated proteins could either be due to their increased deubiquitylation or increased degradation via the 26S proteasome. Also, the ubiquitin antibody used in the above experiment is known to cross-react with free ISG15/UCRP (44), and ISG15 protein is elevated in A-T cells (20). An HA-ubiquitin construct was transfected and then the steady state levels of the HA-polyubiquitylated proteins was assessed (to rule out the possibility of protein polyubiquitylation versus protein polyISGlyation), in the absence or presence of the proteasome inhibitor MG132 (to rule out the possibility of protein deubiquitylation versus protein degradation), in UV treated A-T and ATM+ cells. In FIG. 8B, A-T and ATM+ cells were transfected with a HA-ubiquitin construct. Cells were then treated with MG132 (1 µM) or Bafl (1 nM) for 18 hours and exposed to UV radiation (25 mJ/m2). After recovery in the presence of inhibitors for an additional three hours, cells were lysed. Cell extracts were analyzed by Western blotting for HA-polyubiquitylated proteins and actin using anti-HA and anti-actin antibodies respectively. Intensity of the total HA-polyubiquitylated proteins was quantitated using Bio-Rad Quantity One software and results shown in FIG. 8C. FIG. 8C shows average values (±SEM) of % degradation of HA-polyubiquitylated proteins from three independent experiments.

Consistent with the results shown in FIG. 8A, UV also induced degradation of HA-polyubiquitylated proteins in A-T cells (FIG. 8B, left panel, compare lanes 1 and 2). Intriguingly, MG 132 failed to protect UV-induced decrease of HA-polyubiquitylated proteins in A-T cells (left panel, lanes 3 and 4). UV also induced moderate degradation of HA-polyubiquitylated proteins in ATM+ cells (FIG. 8B, right panel, compare lanes 1 and 2). However, unlike in A-T cells, MG132 completely blocked the decrease of HA-polyubiquitylated proteins in ATM+ cells exposed to UV (FIG. 8B, right panel, lanes 3 and 4). Inhibition of protein disappearance in MG132-treated ATM+ cells indicated that the UV-induced disappearance of HA-polyubiquitylated proteins in A-T cells is not due to their deubiquitylation, but due to their degradation via the 26S proteasome. The MTT assay for cell survival revealed that the degradation of polyubiquitylated proteins was not due to the decreased viability of UV-treated A-T cells under these experimental conditions (data not shown).

The autophagy pathway is induced as a compensatory mechanism to degrade cellular proteins in cells defective in the ubiquitin pathway (31-34). In addition the MG132 proteasome inhibitor induces autophagy (45, 46). Whether the UV-induced degradation of polyubiquitylated proteins is via autophagy in the ubiquitin-pathway was tested in ablated A-T cells. To test the involvement of autophagy, the autophagy inhibitor Bafilomycin A1 (Bafl) (47) was used. Similar to MG132, Bafl also failed to block UV-mediated degradation of polyubiquitylated proteins in A-T cells (FIG. 8B, left panel, lanes 5 and 6). In contrast, Bafl significantly blocked the decrease of HA-polyubiquitylated proteins in ATM+ cells exposed to UV (FIG. 8B, right panel, lanes 5 and 6). Protein degradation in the presence of 50 nM Bafl was assessed, and even this high concentration of Bafl failed to protect UV-induced degradation of cellular proteins in A-T cells (data not shown). The results using ATM+ cells and inhibitors indicates that the failure of Bafl and MG132 to block UV-induced degradation of the polyubiquitylated proteins in A-T cells is not due to the limiting concentration of MG132 and Bafl used, as these inhibitors efficiently blocked the degradation of polyubiquitylated proteins in ATM+ cells. The bar graph of FIG. 8C shows average values (±SE) of % degradation of polyubiquitylated proteins measured from three independent experiments confirming reproducibility of the qualitative results shown in FIG. 8B. Together, these results revealed that UV induces MG132- and Bafilomycin-resistant degradation of polyubiquitylated proteins in A-T cells, but not in ATM+ cells.

Figure 8D:
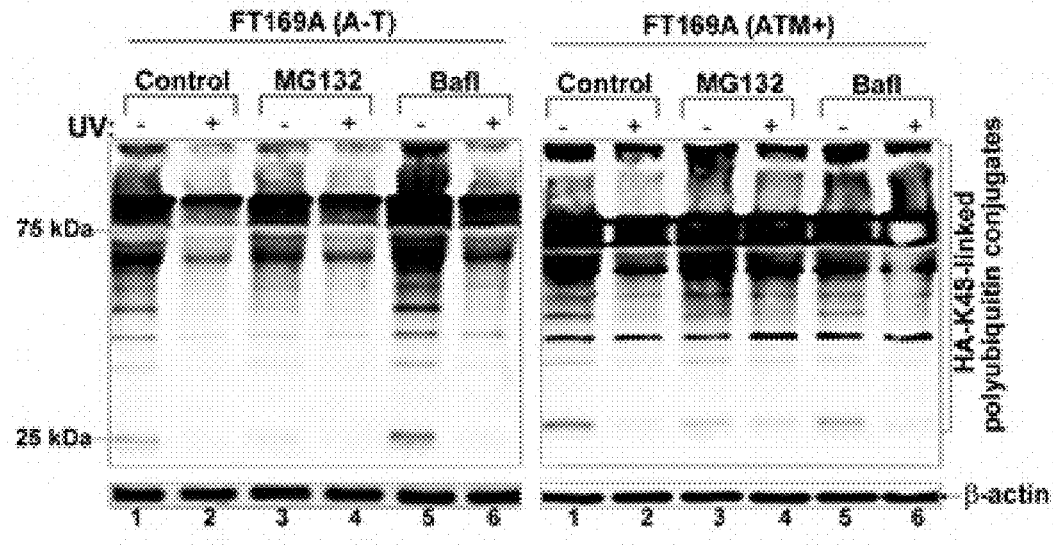
FIG. 8D illustrates A-T and ATM+ cells transfected with HA-Lys48 only ubiquitin construct, and similar treatment as in FIG. 8B. The experiment was repeated two times with reproducible results.

To complement the results shown in FIG. 8B, another construct was used that expresses HA-ubiquitin and that can preferentially make polyubiquitin chains linked through Lys48 on the substrates (20). In FIG. 8D, A-T and ATM+ cells were transfected with HA-Lys48 only ubiquitin construct. The inhibitor and UV treatments, cell lysis, SDS-PAGE, and immunoblotting analysis to detect HA-ubiquitin conjugated proteins using anti-HA antibodies was carried out as described above. The experiment was repeated two times with the reproducible results. Similar results were obtained using this distinct HA-ubiquitin construct (FIG. 8D) as obtained above (FIG. 8B); UV induced MG132- and Bafilomycin-resistant degradation of HA-Lys48-linked polyubiquitylated proteins in A-T cells, but not in ATM+ cells.

Figure 8E:
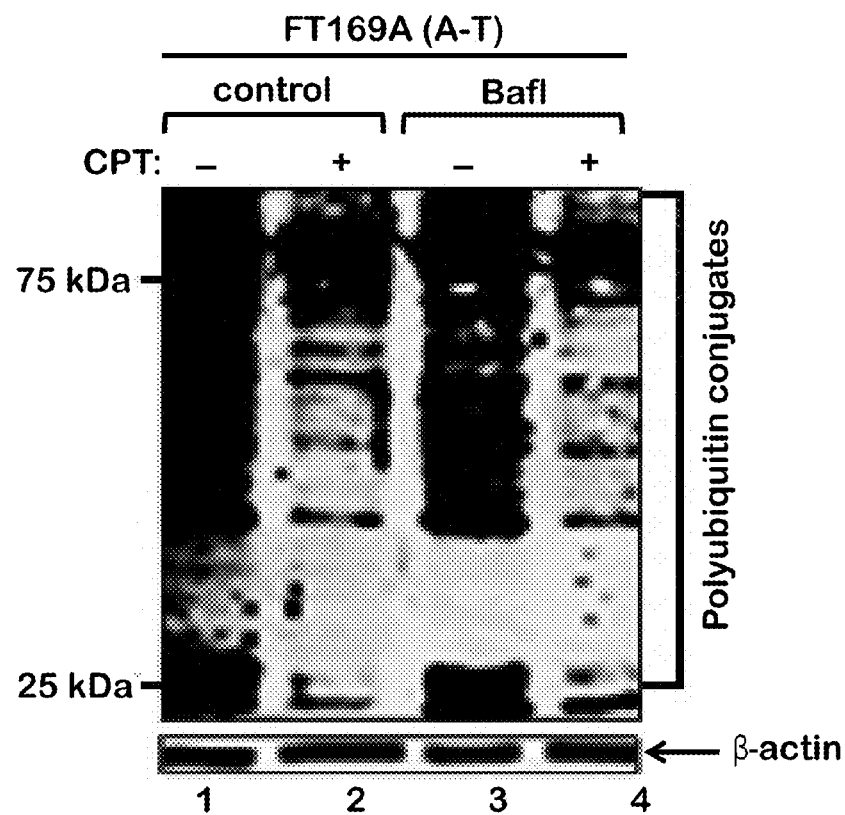
FIG. 8E illustrates A-T cells treated with camptothecin in the presence or absence of Bafl for 24 h, and then ubiquitin conjugated proteins using anti-ubiquitin antibodies detected as described in FIG. 8A.

To test the generality of this observation, the anticancer drug camptothecin (CPT), a genotoxic agent (37, 48-50), which is known to sensitize A-T cells (37), like UV, was used to induce degradation of polyubiquitylated proteins in A-T cells. In FIG. 8E, A-T cells were treated with camptothecin (CPT; 10 µm) in the presence or absence of Bafl (1 nm) for 24 hr. Ubiquitin conjugated proteins using anti-ubiquitin antibodies were detected as described above for FIG. 8A. The experiment was repeated three times. Similar to UV, CPT also induced degradation of endogenous polyubiquitylated proteins (FIG. 8D, lanes 1 and 2) (p<0.0001), and Bafl failed to protect CPT-mediated degradation of polyubiquitylated proteins (FIG. 8D, lanes 3 and 4) in A-T cells (p<0.0001). These results indicate that genotoxins such as UV and CPT induce aberrant degradation of polyubiquitylated cellular proteins in the proteasome function-ablated A-T cells.

Example 9

Basal Autophagy is Activated in A-T Cells Impaired in the Ubiquitin Pathway—

Figure 9A:
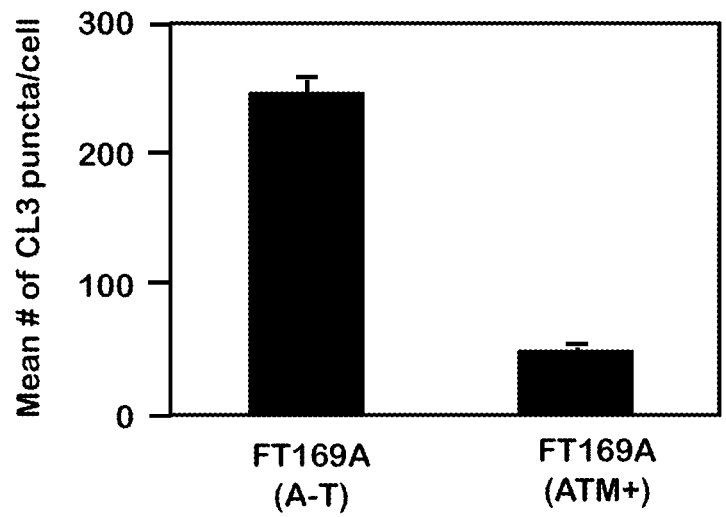
FIG. 9A illustrates the results from immunofluorescence imaging of LC3 puncta in A-T and ATM+ cells, and the average number (±SEM) of puncta counted in 50 cells in different fields shown in the bar graph.

Basal autophagy is activated in Atm knockout mice brains (51); and it is possible that basal autophagy is also activated and genotoxins deregulate activated autophagy leading to aberrant degradation of polyubiquitylated proteins in human A-T cells. To test this hypothesis, the status of endogenous LC3 puncta, a biological marker commonly used to trace induction of autophagy in mammalian cells (52-54), was measured. Immunofluorescence images of LC3 puncta in A-T and ATM+ cells were made and the average number (±SEM) of puncta counted in 50 cells in different fields was counted. The results are shown in FIG. 9A. As shown in FIG. 9A, A-T cells showed a significant increase in LC3 puncta as compared to ATM+ cells. These results reveal that, like in Atm knockout mice, basal autophagy was activated in human A-T cells that are impaired in the ubiquitin pathway.

Figure 9B:
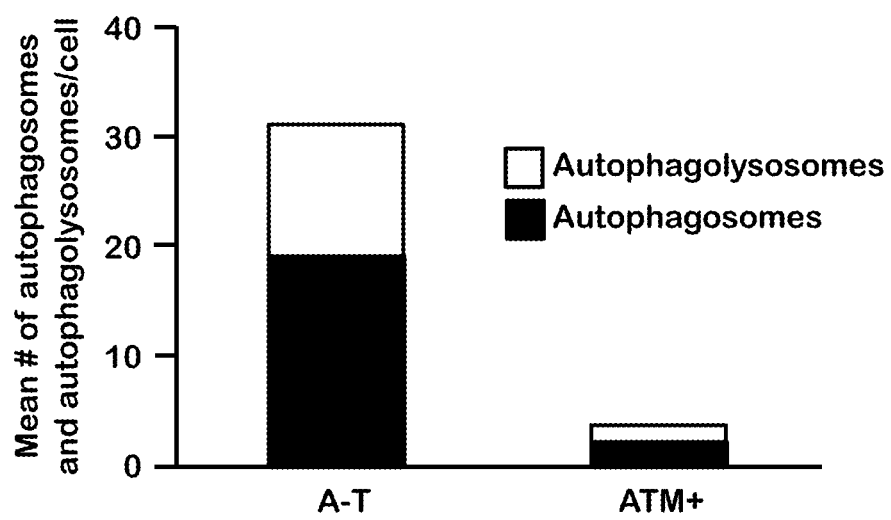
FIG. 9B illustrates the results from imaging A-T and ATM+ cells co-stained with Cyt-ID® and LysoTracker Red® dyes and green (autophagosomes; from Cyt-ID®-stained images; clear (or white) bars) and yellow (autophagolysosomes; from merged images; black bars) dots in cells counted manually using the ImageJ plug-in cell counter. The average number (±SEM) of dots/cell is shown in FIG. 9B. Experiments were repeated two times with similar results.

Autophagy was also examined using Cyto-ID® and LysoTracker Red stains. Cyto-ID® selectively labels autophagic vacuoles (pre-autophagosomes, autophagosomes, and autophagolysosomes) and a fluorescent acidotropic probe LysoTracker Red labels acidic organelles such as lysosomes and autophagolysosomes (54). Appearance of green dots indicated the formation of autophagosomes; red dots indicated lysosomes; and yellow dots in merged images (green dots that overlay red dots in merged images) indicated autophagolysosomes (autophagasomes fused with lysosomes) (Color images not shown). Images of A-T (panels 1-3) and ATM+ (panels 4-6) cells co-stained with Cyt-ID® and LysoTracker Red® dyes were made as described; and images were merged. Green (autophagosomes; from Cyt-ID®-stained panels) and yellow (autophagolysosomes; from merged panels) dots in cells were counted manually using the ImageJ plug-in cell counter. The average number (±SEM) of dots/cell is shown in FIG. 9B, with autophagolysosome number represented by the white bar; and autophagosome number represented by the black bar. Experiments were repeated two times with similar results.

As shown in FIG. 9B, increased autophagosome numbers were seen in A-T compared to ATM+ cells (compare the black bars in FIG. 9B), suggesting increased autophagic activity in A-T cells. In addition, there was a significant increase in autophagolysosome numbers in A-T compared to ATM+ cells (compare the white bars in FIG. 19B). Together, immunofluorescence data using anti-LC3 antibodies and Cyto-ID/LysoTrack Red dyes revealed that basal autophagy is activated in A-T cells.

Example 10

Degradation of Autophagy Substrates is Deregulated in UV-Exposed A-T Cells—

Figure 10A:
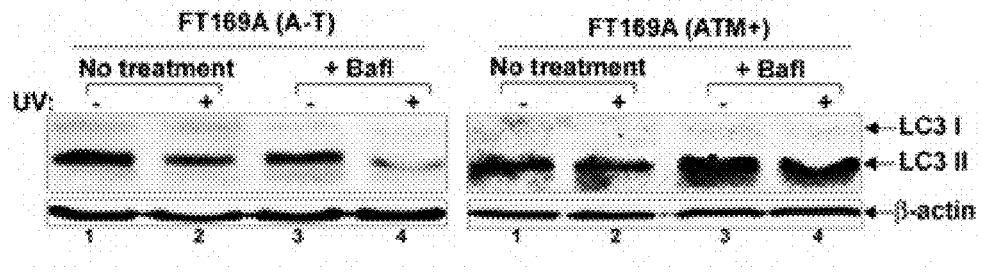
FIGS. 10A-10D illustrate Western blot analysis of A-T and ATM+ cells treated with Bafl, and then exposed to UV as indicated (25 mJ/m2). After recovery for 3 h in the presence of inhibitors, cells were lysed, and the lysates analyzed by Western blotting for LC3 (FIG. 10A), p62 (FIGS. 10C), and actin (lower panels, FIGS. 10A and 10D) using their specific antibodies. Intensity of the total LC3 (LC3-I+II) and p62 proteins was quantitated using BioRad Quantity One software, and the results shown in FIGS. 10B and 10D, respectively.
Figure 10B:
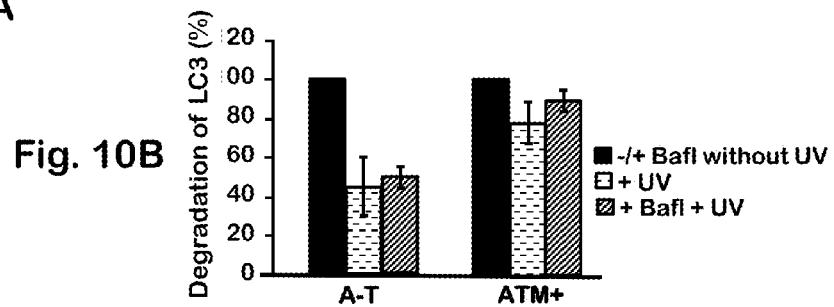
Figure 10C:
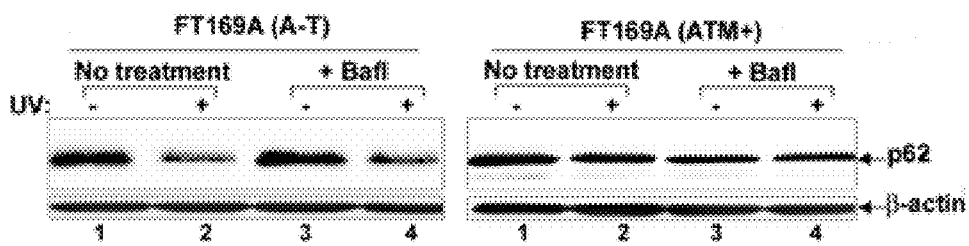
Figure 10D:
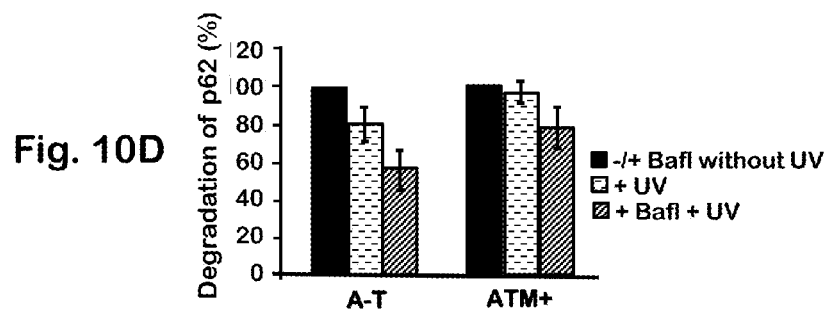

Because degradation of proteasome substrates is deregulated in A-T cells, the degradation of the autophagy substrates (autophagic flux) LC3 and p62 was assessed in UV-exposed A-T and ATM+ cells (55). For FIGS. 10A-10D, A-T and ATM+ cells were treated with Bafl (1 nM for 18 h) and then exposed to UV as indicated (25 mJ/m2). Three hours after recovery in the presence of inhibitors, cells were lysed. Cell lysates were analyzed by Western blotting for LC3 (FIG. 10A), p62 (FIG. 10CB), and actin (lower panels in FIGS. 10A and 10C) using their specific antibodies. Intensity of the total LC3 (LC3-I+II) and p62 proteins was quantitated using BioRad Quantity One software, and the results shown in FIGS. 10B and 10D, respectively. FIGS. 10B and 10C show average values (±SEM) of % degradation of LC3 and p62 from three independent experiments. All control values (−UV and +Bafl) are normalized to 100%, and values for experimental treatments were expressed as percent variations over control As shown in FIGS. 10A-10D, UV induced degradation of LC3 and p62 (FIGS. 10A and 10C, left panels, lanes 1 and 2) in A-T cells. The autophagy inhibitor Bafl failed to protect UV-mediated degradation of LC3 and p62 in A-T cells (FIGS. 10A and 10C, left panels, lanes 3 and 4). On the other hand, no apparent changes in LC3 and p62 levels were detected in ATM+ cells treated with UV in the absence or presence of Bafl (FIGS. 10A and 10C, right panels). FIGS. 10B and 10D show average (+/−SEM) degradation of LC3 (LC3-I and II) and p62 proteins in UV-exposed A-T and ATM+ cells treated with Bafl from three independent experiments. These results revealed that, like the proteasome substrates (Example 8), UV also induces aberrant degradation of autophagy substrates in A-T cells.

Figure 11A:
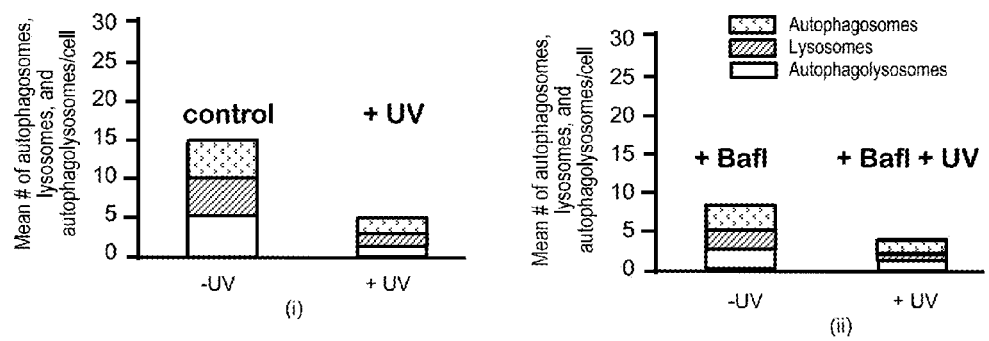
FIGS. 11A and 11B illustrate the results from A-T (FIG. 11A) and ATM+(FIG. 11B) cells treated with Bafl and exposed to UV. Three hours after recovery in the presence of inhibitors, cells were co-stained with Cyt-ID® and LysoTracker Red® dyes. Green (autophagosomes; from Cyt-ID®-stained panels; stippled bars), red (lysosomes; from LysoTracker Red-stained panels; lined bars), and yellow (autophagolysosomes; from merged panels; clear (or white) bars) dots in A-T (FIG. 11A) and ATM+(FIG. 11B) cells were counted manually using the ImageJ plug-in Cell Counter. Mean number of dots/cell are shown in FIGS. 11A and 11B. Experiments were repeated two times with similar results.
Figure 11B:
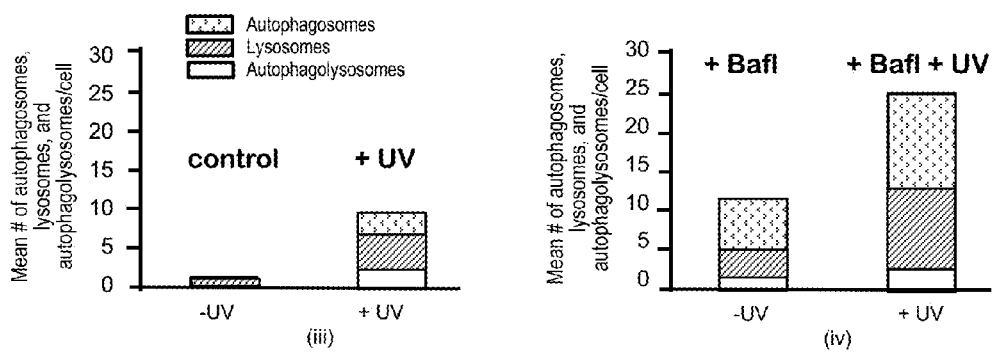

Autophagic flux was also monitored using Cyto-ID® and LysoTrack Red dyes. The quantitation of the immunofluorescence data is shown in FIGS. 11A and 11B. A-T and ATM+ cells were treated with Bafl (1 nM for 18 h) and then exposed to UV (25 mJ/m2) as indicated. Three hours after recovery in the presence of inhibitors, cells were co-stained with Cyt-ID® and LysoTracker Red® dyes. Fluorescence images of Cyt-ID® and LysoTracker Red® stained cells were made (Color images not shown). Green (autophagosomes; from Cyt-ID®-stained panels), red (lysosomes; from LysoTracker Red-stained panels), and yellow (autophagolysosomes; from merged panels) dots in A-T and ATM+ cells were counted manually using the ImageJ plug-in Cell Counter. Mean number of dots/cell is shown in FIGS. 11A and 11B, respectively. In FIGS. 11A and 11B, the number of autophagosomes (green dots) is represented by stippled bars; the number of lysosomes (red dots) is presented by lined bar; and the number of autophagolysosomes (yellow dots) is represented by clear (white) bars. Experiments were repeated two times with similar results.

As shown by the numbers in FIGS. 11A and 11B, autophagolysosomes were formed in UV/Bafl-treated/untreated cells. In the colored images, when the green dots did not overlay red dots and appeared as green in merged images, indicated a failure of fusion between autophagosomes and autolysosomes in UV/Bafl-treated/untreated cells. Decrease in the number of green, red and yellow dots was taken as an indication of increased autophagic flux in UV/Bafl-treated/untreated cells as the autophagolysosomes break down and disappear at the end of autophagy. As shown in FIGS. 11A and 11B, control A-T cells displayed increased autophagic activity over control ATM+ cells. However, upon UV-treatment, most colored dots disappeared in A-T cells. In contrast, the number of colored dots was markedly increased in UV-treated ATM+ cells (compare FIG. 11A(i) with FIG. 11B(iii). Disappearance of the autophagic organelles in A-T and appearance of the autophagic organelles in ATM+ cells revealed that UV induces autophagic flux in A-T, but not in ATM+ cells.

Bafilomycin inhibits autophagic flux by blocking fusion between autophagosomes and autolysosomes. A decreased appearance of autophagolysosomes (yellow dots) in cells treated with Bafl was expected. Surprisingly, increased number of autophagolysosomes were consistently seen in Bafl-treated A-T cells as compared to the Bafl-treated ATM+ cells. (See FIGS. 11A(ii) and 11B(iv)). In contrast, more autophagosomes were seen in Bafilomycin treated ATM+ cells as compared to A-T cells. These results suggested that Bafl blocked fusion between autophagosomes and lysosomes in ATM+ cells, but failed to do so in A-T cells.

Additionally, as shown in FIGS. 11A and 11B, UV/Bafl co-treatment decreased autophagy activity in A-T cells as compared to A-T cells treated with Bafl alone. The disappearance of yellow dots representing autophagolysosomes in A-T cells indicated that UV induced autophagic flux and Bafl failed to protect autophagic flux in UV/Bafl-treated A-T cells (See FIG. 11A(ii)). Since lysosomal number and size decreases upon autophagy maturation, decrease in lysosomal dots in UV-treated A-T cells further supports that UV-mediated induction of autophagy leads to increased autophagic flux in A-T cells. Although UV/Bafl co-treatment increased autophagosomes, the number of autophagolysosomes remained unaltered in UV/Bafl-treated ATM+ cells as compared to ATM+ cells treated with Bafl alone (FIG. 11B(iv)). This result suggested that UV induced formation of autophagosomes, but Bafl blocked their fusion with lysosomes, i.e. formation of autophagolysosomes, in ATM+ cells. In addition, the unaltered number of autophagolysosomes in Bafl-treated versus UV/Bafl-treated ATM+ cells provided evidence that UV did not induce autophagic flux in Bafl-treated ATM+ cells.

Together, results using A-T and ATM+ cells revealed that: (a) UV induces aberrant degradation of the proteasome substrates in A-T cells; (b) basal autophagy is activated in A-T cells; (c) UV induces aberrant autophagic flux in A-T cells; (d) Bafilomycin blocked formation of autophagolysosomes and, consequently, autophagic flux in UV-treated ATM+ cells; and (e) Bafilomycin failed to block fusion between autophagosomes and lysosomes resulting in sustained formation of autophagolysosomes and, thus, increased autophagic flux in UV-treated A-T cells. Similar findings were observed in cells treated with another autophagy inhibitor NH4C1 in A-T cells (data not shown).

Example 11

Figure 12A:
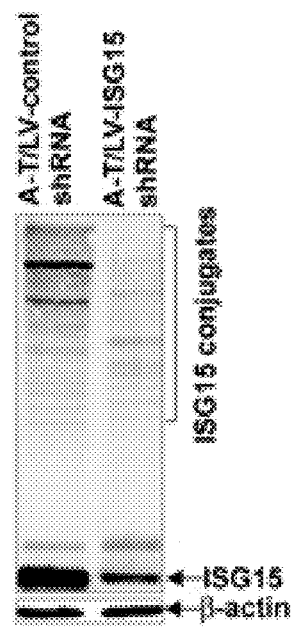
FIGS. 12A and 12B illustrate extracts of A-T/LV-control and ISG15 shRNA cells as analyzed by Western blotting for ISG15 and actin (FIG. 12A), and representative immunofluorescence images of LC3 puncta in A-T/control (left panel) and ISG15 (right panel) shRNA cells (Scale bar: 10 µM) (FIG. 12B).

Induction of Basal Autophagy is a Consequence of Constitutively Elevated ISG15 in A-T Cells As discussed above, ISG15 siRNA was shown to restore impaired proteasome function suggesting the involvement of the constitutively elevated ISG15 pathway in inhibiting the ubiquitin pathway in A-T cells. If induction of basal autophagy compensates ISG15-impaired proteasome function, ISG15 siRNA should restore the proteasome function and suppress activated autophagy in A-T cells. To test whether this is indeed the case, stable clones of FT169A (A-T) cells expressing lentiviral ISG15 shRNA (A-T/LV-ISG15 shRNA) or control shRNA (A-T/LV-control shRNA) were generated. In FIG. 12A, extracts of A-T/LV-control and ISG15 shRNA cells were analyzed by Western blotting for ISG15 and actin. The Western blot in FIG. 12A confirmed the efficient knock-down of ISG15 expression in A-T/LV-ISG15 shRNA cells.

Figure 12B:
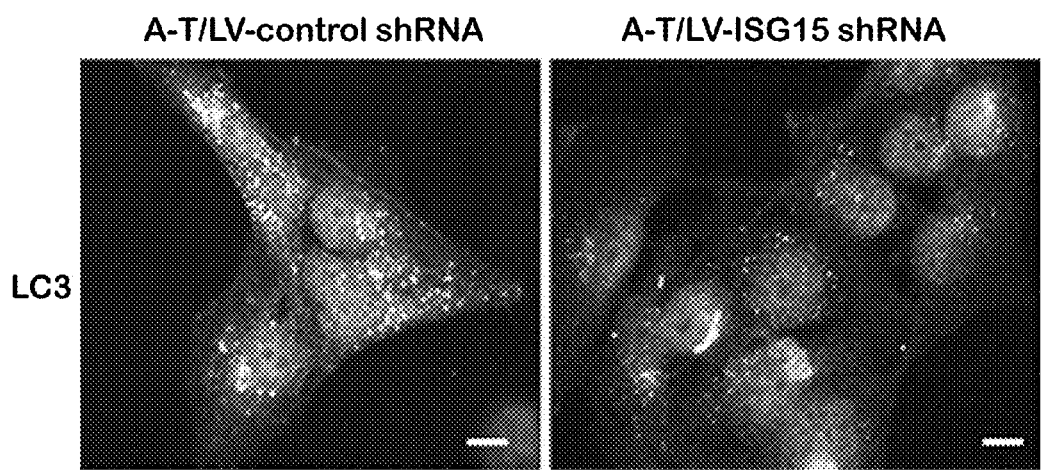

In FIG. 12B, representative immunofluorescence images of LC3 puncta in A-T/control (left panel) and ISG15 (right panel) shRNA cells are shown (Scale bar: 10 μM). To test if the autophagy pathway is restored, LC3 puncta was measured in ISG15-silenced A-T cells. As shown in FIG. 12B, A-T/LV-control shRNA cells exhibited increased number of LC3-positive puncta (average # of 67 puncta/cell) as compared to A-T/LV-ISG15 shRNA cells (average number of 5 puncta/cell). These results revealed that basal autophagy is activated, and activated autophagy is due to the elevated expression of ISG15 in A-T cells.

To further test whether silencing of ISG15 expression attenuated autophagy, these cells were stained with Cyto-ID® and LysoTracker Red dye as described in FIGS. 9A and 9B. The same criteria were used to judge autophagic activity in immunofluorescence analysis as described in FIGS. 9A and 9B. Images of A-T/control and ISG15 shRNA cells co-stained with Cyt-ID® and LysoTracker Red® (Red; for lysosomes) dyes were made, with a yellow color in the merged images indicating autophagolysosomes. (Images not shown). A decreased number of green and yellow dots was seen in A-T/LV-ISG15 shRNA as compared to A-T/LV-control shRNA cells (data not shown), suggesting attenuation of autophagic activity in A-T/ISG15-shRNA cells.

Together, immunofluorescence data using anti-LC3, Cyto-ID, and LysoTrack Red dyes revealed that, as shown above in FT169A (A-T) cells (FIGS. 10A-10C), basal autophagic activity is increased in A-T/LV-control shRNA cells, and activated autophagy is due to the elevated expression of ISG15 in A-T/LV control cells.

Example 12

Degradation of Autophagy Substrates is Restored in the ISG15-Silenced A-T Cells

Whether ISG15 gene knock down restores autophagy and rescues UV-induced autophagic flux was assessed using A-T/LV-control/ISG15-shRNA stable clones. In FIGS. 13A-13D, A-T/LV-control and ISG15 shRNA cells were treated with Bafl (1 nM for 18 h) or left untreated. Cells were then exposed to UV (25 mJ/m2). Three hours after recovery in the presence of inhibitors, cells were lysed and lysates were analyzed by Western blotting for LC3 (FIG. 13A) and p62 (FIG. 13C), and actin (lower panels, FIGS. 13A and 13C) using their specific antibodies. Intensity of the total LC3 (LC3-I+II) and p62 proteins was quantitated using BioRad Quantity One software, and the results shown in FIGS. 13B and 13D. FIGS. 13B and 13D show average values (±SEM) of % degradation of LC3 and p62 from three independent experiments. All control values (−UV and +Bafl) are normalized to 100%, and values for experimental treatments were expressed as percent variations over control.

Figure 13A:
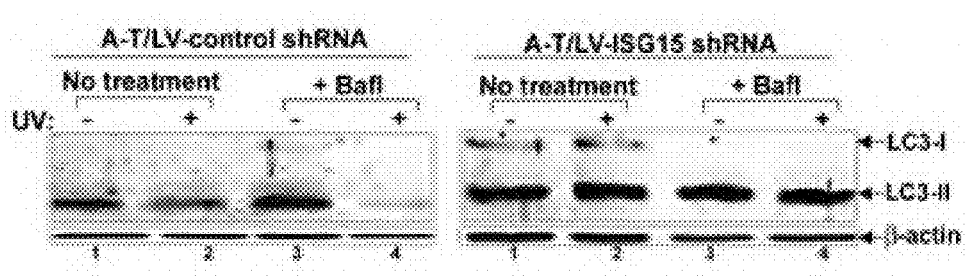
FIGS. 13A-13D illustrate Western blot analysis of A-T/LV-control and ISG15 shRNA cells treated with Bafl or left untreated, and then exposed to UV. Three hours after recovery in the presence of inhibitors, cells were lysed and lysates were analyzed by Western blotting for LC3 (FIG. 13A) and p62 (FIG. 13C), and actin (lower panels for FIGS. 13A and 13C) using their specific antibodies. Intensity of the total LC3 (LC3-I+II) and p62 proteins was quantitated using BioRad Quantity One software. The bar graphs in (FIGS. 13B and 13D) show average values (±SEM) of % degradation of LC3 and p62 from three independent experiments. All control values (−UV and +Bafl) are normalized to 100%, and values for experimental treatments were expressed as percent variations over control.
Figure 13B:
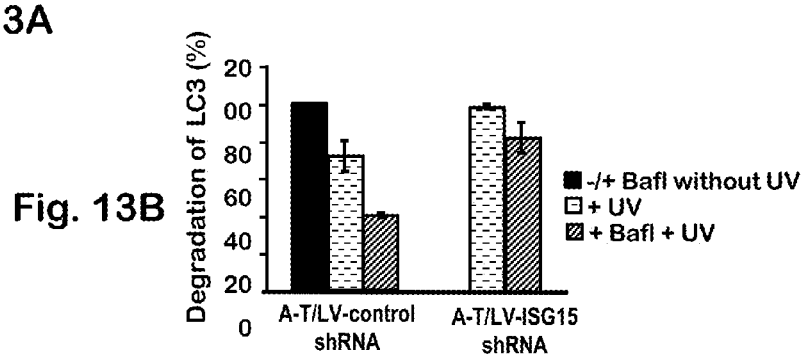
Figure 13C:
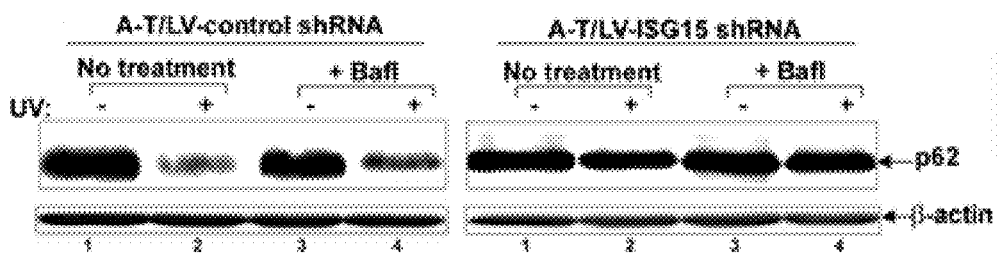
Figure 13D:
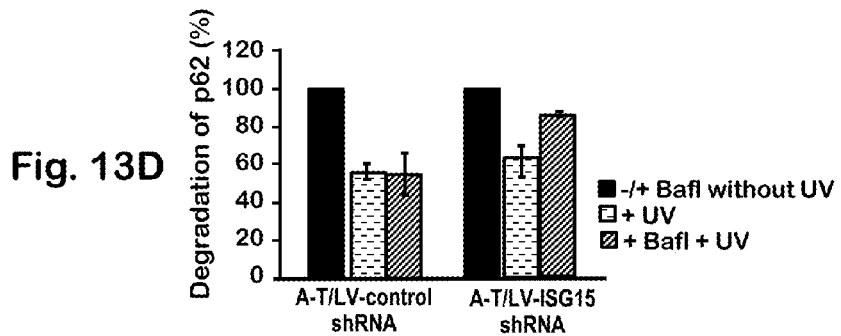

As shown in FIGS. 13A-13D, UV also was found to induce MG132 and Bafl-resistant degradation of LC3 and p62 in A-T/control-shRNA cells but not in A-T/ISG15-shRNA cells (FIGS. 13A and 13C). The bar graph in FIGS. 13B and 13D show average (±SEM) degradation of LC3 (LC3-I and II) and p62 proteins in UV-exposed A-T/LV-control/ISG15 shRNA cells treated with Bafl from three independent experiments. These results further revealed that the constitutively elevated ISG15 pathway contributes to the UV-induced aberrant autophagic flux in A-T cells.

Autophagic flux was also assessed using Cyto-ID® and LysoTrack Red dyes as described above in FIGS. 9A, 9B, and 11. The same criteria were used to judge autophagic activity in immunofluorescence analysis as described for FIGS. 11A and 11B. UV induced disappearance of autophagosomes (green dots) and autophagolysosomes (yellow dots) in bafilomycin untreated (mean # of green dots/cell=4.6 vs. 1.8 and mean # of yellow dots/cell=3.8 vs. 1) and treated [mean # of green dots/cell=6 vs. 0.8 and mean # of yellow dots/cell=5.8 vs. 1.5] A-T/control shRNA cells. (Color images not shown) Since disappearance of autophagolysosomes indicates increased autophagic flux, these results suggested that Bafilomycin failed to protect UV-mediated autophagic flux in A-T/LV-control shRNA cells.

Figure 14A:
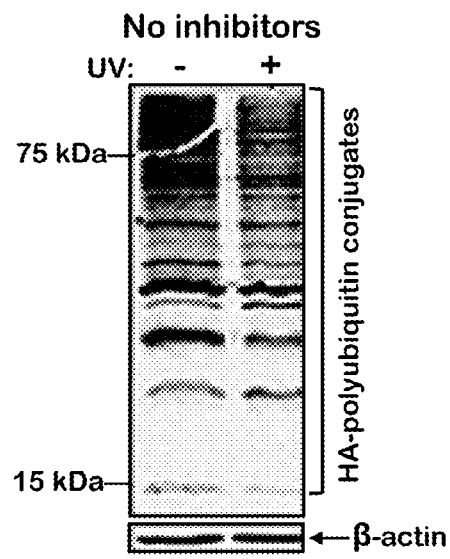
FIG. 14A illustrates HA-ubiquitin-transfected A-T/LV-control shRNA cells exposed to UV. After three hours of recovery, assessment of HA-polyubiquitylated proteins was carried out as described for FIG. 8B.
Figure 14B:
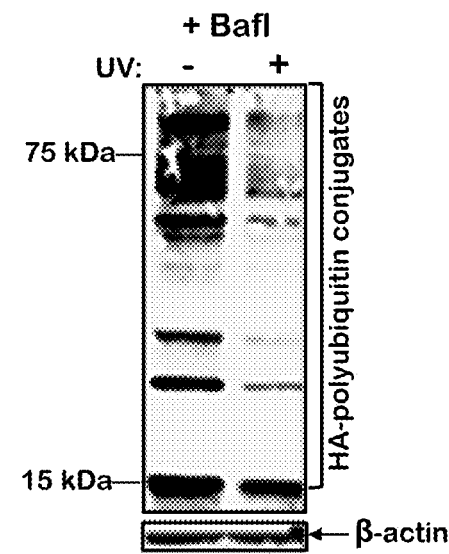
FIG. 14B illustrates HA-ubiquitin-transfected A-T/LV-control shRNA cells treated with Bafl, and then exposed to UV. After three hours of recovery in the presence of the inhibitor, assessment of HA-polyubiquitylated proteins was conducted as in FIG. 8B.

For FIG. 14A, HA-ubiquitin-transfected A-T/LV-control shRNA cells were exposed to UV (25 mJ/m2). After three hours of recovery, assessment of HA-polyubiquitylated proteins was carried out as described above for FIG. 8B. In FIG. 14B, HA-ubiquitin-transfected A-T/LV-control shRNA cells were treated with Bafl (1 nm for 18 h). Cells were then exposed to UV (25 mJ/m2). After three hours of recovery in the presence of the inhibitor, assessment of HA-polyubiquitylated proteins was carried out as described for FIG. 14A. For FIG. 14C, HA-ubiquitin-transfected A-T/LV-control shRNA cells were treated with MG132 (1 nm for 18 h). Cells were then exposed to UV (25 mJ/m2). After three hours of recovery in the presence of the inhibitor, assessment of HA-polyubiquitylated proteins was carried out as described for FIG. 14A. For FIG. 14D, HA-ubiquitin-transfected A-T/LV-control shRNA cells were treated with 3-MA (10 nm for 18 h). Cells were then exposed to UV (25 mJ/m2). After three hours of recovery in the presence of the inhibitor, assessment of HA-polyubiquitylated proteins was carried out as described for FIG. 14A. All experiments shown in FIGS. 14A-14D were performed at least three times and yielded similar results.

Figure 14C:
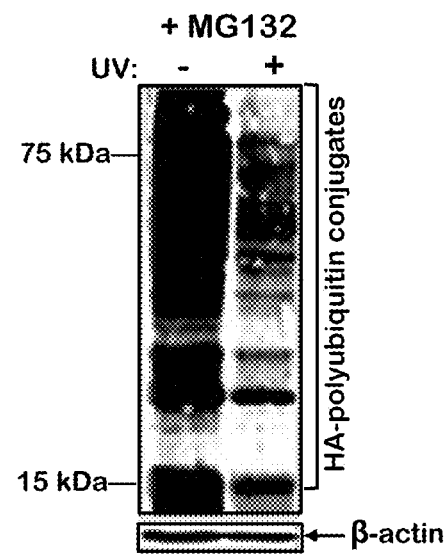
FIG. 14C illustrates HA-ubiquitin-transfected A-T/LV-control shRNA cells treated with MG132, and then exposed to UV. After three hours of recovery in the presence of the inhibitor, assessment of HA-polyubiquitylated proteins was carried out as described in FIG. 8B.

Using Western blot analysis, UV treatment was shown to induce degradation of HA-polyubiquitylated proteins in Bafilomycin-untreated (FIG. 14A)/treated (FIG. 14B) A-T/LV-control cells. This degradation was not due to the proteasome as MG132, a proteasome inhibitor failed to block UV-mediated degradation of proteins in A-T/LV-control shRNA cells (FIG. 14C).

Figure 14D:
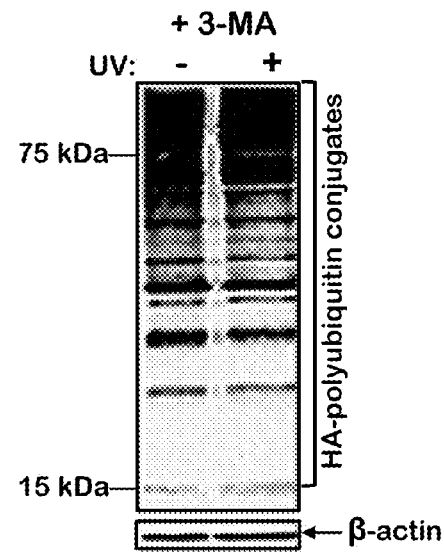
FIG. 14D illustrates HA-ubiquitin-transfected A-T/LV-control shRNA cells treated with 3-MA, and then exposed to UV. After three hours of recovery in the presence of the inhibitor, assessment of HA-polyubiquitylated proteins was carried out as described in FIG. 8B. All experiments shown in FIGS. 14A-14D were performed at least three times and yielded similar results.

Bafilomycin inhibits autophagy at a late stage (47). Whether 3-methyl adenine (3-MA), an autophagy inhibitor known to inhibit autophagy at early stage by inhibiting formation of autophagosomes (56), could block UV-induced autophagic flux was tested in A-T/LV-control shRNA cells. Using Cyto-ID® and LysoTrack Red dyes as described above in FIGS. 9A, 9B, 11A and 11B, the same criteria were used to judge autophagic activity in immunofluorescence analysis as described for FIGS. 11A and 11B. A marked decrease in both green (mean dots/cell=4.6 vs. 0.16) and yellow (mean dots/cell=3.8 vs. 0.5) dots was seen, suggesting decreased formation of autophagosomes and autophagolysosomes in 3-MA-treated A-T/LV-control shRNA cells. (Images not shown) Moreover, both green dots and yellow dots remained unaltered in A-T/LV-control shRNA cells co-treated with 3-MA and UV. These results suggested that 3-MA blocked autophagic activity and UV-mediated autophagic flux in A-T/LV-control shRNA cells. Consistent with these results, using Western blot analysis, UV-induced degradation of HA-polyubiquitylated proteins was markedly blocked in 3-MA/UV-treated A-T/LV/control shRNA cells (FIG. 14D). These results using 3-MA and Bafilomycin reveal that UV over-activates autophagy in A-T cells. Bafilomycin is unable to block the over-activated autophagy leading to aberrant autophagic flux in A-T cells. In contrast, 3-MA that inhibits autophagosome formation markedly blocked autophagic flux in A-T cells.

The effect of 3-MA on UV-induced autophagic flux was tested in A-T/LV-ISG15 shRNA cells. A-T/LV-ISG15 shRNA cells were either left untreated or treated with 3-MA (10 nM for 18 h), and cells were then exposed to UV (25 mJ/m2). Three hours after recovery in the presence of the inhibitor, cells were co-stained with Cyt-ID® and LysoTracker Red® dyes. Fluorescence images of Cyt-ID® and LysoTracker Red® stained cells were made. No apparent change was noted in autophagic activity in ISG15-silenced A-T and 3-MA-treated ISG15-silenced A-T cells exposed to UV (Images not shown).

Figure 15A:
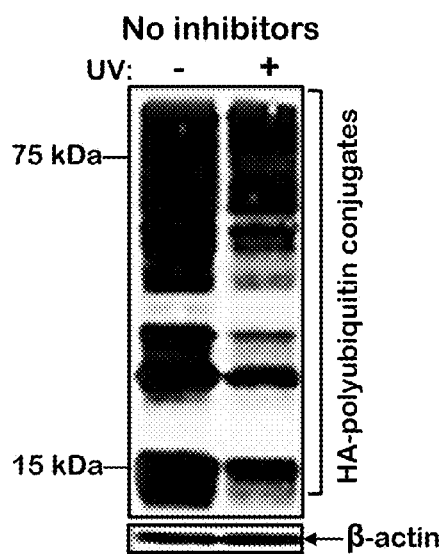
FIG. 15A illustrates HA-ubiquitin-transfected A-T/LV-ISG15 shRNA cells exposed to UV. After three hours of recovery, assessment of HA-polyubiquitylated proteins was carried out as described in FIG. 8B.

In FIG. 15A, HA-ubiquitin-transfected A-T/LV-ISG15 shRNA cells were exposed to UV (25 mJ/m2). After three hours of recovery, assessment of HA-polyubiquitylated proteins was carried out as described as above for FIGS. 8A-8E. For FIG. 15B, HA-ubiquitin-transfected A-T/LV-ISG15 shRNA cells were treated with 3-MA (10 nm for 18 h). Cells were then exposed to UV (25 mJ/m2). After three hours of recovery in the presence of the inhibitor, assessment of HA-polyubiquitylated proteins was carried out as described above. For FIG. 15C, HA-ubiquitin-transfected A-T/LV-control shRNA cells were treated with MG132 (1 nm for 18 h). Cells were then exposed to UV (25 mJ/m2). After three hours of recovery in the presence of inhibitor, assessment of HA-polyubiquitylated proteins was carried out as described. All experiments shown in FIGS. 15A-15C were performed at least three times and yielded similar results.

Figure 15B:
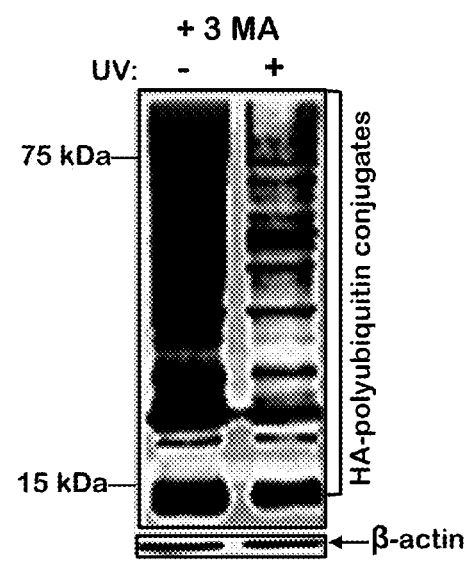
FIG. 15B illustrates HA-ubiquitin-transfected A-T/LV-ISG15 shRNA cells treated with 3-MA, and then exposed to UV. After three hours of recovery in the presence of the inhibitor, assessment of HA-polyubiquitylated proteins was carried out as described in FIG. 8B.
Figure 15C:
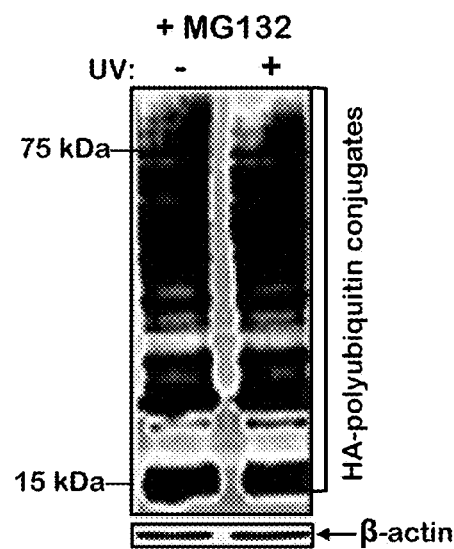
FIG. 15C illustrates HA-ubiquitin-transfected A-T/LV-control shRNA cells treated with MG132, and then exposed to UV. After three hours of recovery in the presence of inhibitor, assessment of HA-polyubiquitylated proteins was carried out as described in FIG. 8B. All experiments in FIGS. 15A-15C were performed at least three times and yielded similar results.

Although autophagy was attenuated, UV induced degradation of HA-polyubiquitylated proteins in both 3MA untreated and treated ISG15-silenced cells (FIGS. 15A and 15B). Without wishing to be bound by this theory, it is believed that the degradation of HA-polyubiquitylated proteins is due to the restoration of proteasome function in ISG15-silenced A-T cells. Indeed, the MG132 proteasome inhibitor was found to completely block degradation of HA-polyubiquitylated proteins, suggesting that UV-mediated degradation of HA-polyubiquitylated proteins in 3-MA-treated A-T cells was due to their degradation via the proteasome in ISG15-silenced A-T cells.

These results indicate that autophagy is activated in A-T cells presumably to compensate for the impaired proteasome function in A-T cells. Genotoxic stress over-activates this compensatory mechanism, triggering aberrant autophagic flux in A-T cells. 3-MA attenuated over-activated autophagy and resulted in attenuation of autophagic flux in genotoxin-treated autophagy.

Example 13

The Autophagy Pathway is Activated in Brains of Human A-T Patients—

Astroglial cell dysfunction has been implicated in the pathogenesis of various neurological disorders, (57) and ISG15 is elevated in A-T astrocytes as shown above. Evidence of autophagy induction was assayed in the A-T human brains. The deparaffinized human brain tissue sections from the normal subject and A-T patient were double stained with anti-LC3- and anti-GFAP-specific antibodies (scale bar: 100 μm), as described above. A dramatic increase in both LC3 (autophagy marker)/GFAP (astrocytes marker) double-positive stained inclusions was seen in the mid-brain sections obtained from the A-T patient. (Images not shown) Although LC3/GFAP inclusions were also present in brain sections of the normal individual, the intensity of the LC3/GFAP double-positive staining was much higher in the brain section A-T patient as compared to the normal individual. Similar increases in the LC3/GFAP double-positive staining were noted in the brain sections of the two other A-T patients (data not shown).

Figure 16:
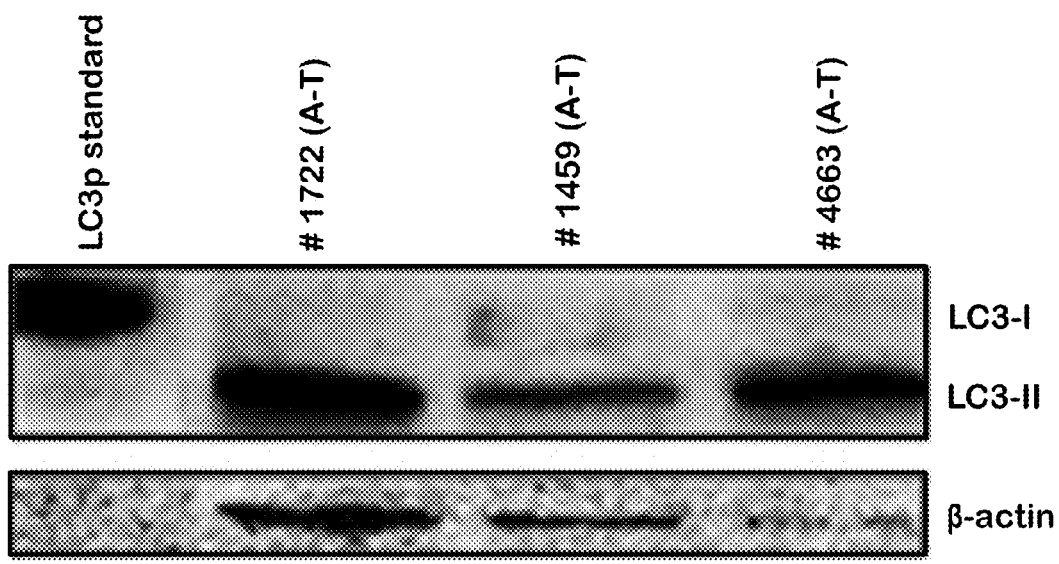
FIG. 16 illustrates Western blot analysis using anti-LC3 antibodies of frozen mid-brain postmortem tissue lysates from human brains of A-T patients. Positive control for anti-LC3 protein (HA-tagged) (MBL International) was loaded in lane 1.

Tissue lysates of mid-brain regions (specifically containing substantia nigra) obtained postmortem from A-T human patients with confirmed A-T disease were examined for autophagy induction by Western blotting using anti-LC3 antibodies. Frozen mid-brain postmortem tissue lysates were analyzed by Western blotting using anti-LC3 antibodies. Positive control for anti-LC3 protein (HA-tagged) (MBL International) was loaded in lane 1. The results are shown in FIG. 16. The presence of LC3-II form in brain tissue lysates is indicative of a strong induction of autophagy in these patients, as LC3-II form is an indicator of an active autophagy. Together, these results indicate that autophagy is aberrantly activated in A-T patients.

The above results are relevant for improving the health status of A-T patients who are constantly exposed to environmental genotoxic agents such as sunlight, viral infections, high temperature, and human made mutagenic chemicals during their life time. In addition, A-T patients are vulnerable to oxidative stress (69) which can lead to protein damage. Without wishing to be bound by this theory, I believe that genotoxic agents and oxidative stress can induce autophagic stress in A-T neurons which, in turn, leads to their autophagic death. Previously, the hypersensitivity to the genotoxic stress has been principally linked to defective DNA repair in A-T. The above results indicate that, in addition to the deregulated DNA repair, deregulation of the protein turnover in part contributes to the genotoxic stress-mediated hypersensitivity in A-T patients. Knowing that constitutively elevated ISG15 is causally related to the deregulation of both the major protein turnover pathways in A-T fibroblast cells allows targeting the ISG15 pathway to reduce neurodegeneration and ataxia associated with it in A-T patients. In addition, attenuating autophagy with pharmacological inhibitors of autophagy (e.g. 3-MA) can prevent neurodegeneration in A-T.

Example 14

Use of A-T Models

Past studies demonstrate that astrocytes are important players in various neurological disorders. As shown above, the autophagy marker LC3 was elevated in human A-T astrocytes. In addition, ISG15 is elevated in A-T astrocytes obtained from A-T knockout mice. These results indicate that ISG15-mediated defective turnover of proteins in A-T astrocytes could lead to astrocyte death which in turn could lead to non-cell-autonomous cerebellar neuronal cell death in A-T. Using A-T mouse model (ex vivo and in vivo), the genotoxins-induced ISG15-mediated defects in the protein turnover pathways (ISG15 proteinopathy) will be shown to contribute to A-T neurodegeneration. I will develop $Atm^{-/-}$/ $ISG15^{-/-}$ and $Atm^{-/-}$/GFP-LC3 double knockout mouse models to be used to test the role of ISG15 and autophagy in A-T neurodegeneration. Both mice models will be useful to understand the molecular mechanism(s) underlying neurodegeneration in A-T.

$Atm^{-/-}$ mice do not show obvious neuropathology, and this apparent lack of neuropathology acts as an obstacle in studying neurodegeneration in $Atm^{-/-}$ mice. The concept that the genotoxic stress is needed to trigger ISG15 proteinopathy-induced neurodegeneration in $Atm^{-/-}$ mice will be tested. These results will enable the use of $Atm^{-/-}$ mice for studying neurodegeneration. Also, experiments will be run to confirm that ISG15, which is elevated in A-T astrocytes, consequently impairs astrocyte function; impaired astrocyte function in turn leads to non-autonomous A-T cerebellar neuronal cell death.

Currently there is no cure or preventive therapy for A-T disease. Knowing that the constitutively elevated ISG15 pathway is causally related to the deregulation of both the major protein turnover pathways in A-T cells, a cause of neurodegeneration in A-T, provides targets for development of inhibitors to target the ISG15 pathway to reduce neurodegeneration and prevent or reduce ataxia associated with neurodegeneration. Small molecular inhibitors targeting the ISG15 pathway could be developed and tested using the model system for protein turnover in A-T cells.

Analysis of the autophagy substrates using fluorescence microscopy: To monitor autophagy in cerebellar astrocytes (in tissue sections), brain sections will be co-immunostained for p62 and/or LC3, both autophagy substrates and markers, together with the astrocytes specific marker GFAP or calbindin. To monitor autophagy in cerebellar neurons (in tissue sections), brain sections will be co-immunostained for p62 and/or LC3, together with the neuronal-specific marker Neu-N.

Analysis of autophagy substrates and ISG15 using immunoblotting. A-T mice and human brain sections, cells, and serum will be processed for the detection of ISG15 and autophagy markers using Western blotting analysis.

Autophagy organelles using transmission electron microscopy: The autophagic organelles [autophagasomes (double-membrane structures containing undigested cytoplasmic contents, which have not fused with a lysosome), and autophagolysosomes (a single limiting membrane structures that contains cytoplasmic materials at various stages of degradation)] will be analyzed using electron microscopy.

Tissue fractionation: Endogenous p62 becomes Triton X-100-insoluble in the presence of protein aggregates, a characteristic of neurodegenerative diseases. Triton X-100-insoluble proteins isolated from A-T human and mice brain sections will be analyzed using anti-p62 antibodies in Western analysis.

Quantitation of autophagy: The number of LC3- and/or lysotracker-positive puncta/total intensity of the stain in brain slices will be quantitated using image J software. Western blotting results will be quantitated using BioRad and/or Kodak data analysis software.

The ex vivo organotypic brain slice culture model: Several studies show that neuronal morphology, cellular, and anatomical relations and network connections are maintained in organotypic brain slice cultures. The organotypic brain slices obtained from A-T knockout mice have been used by others to examine the ATM-mediated DNA damage response in murine cerebellar neurons. This study demonstrated that ATM is autophosphorylated in the nuclei after DNA damage (X-ray irradiation) in ATM+, but not in A-T mouse brain slices. This result reveals that the DNA damage repair response pathway is intact in the organotypic brain slice cultures, and demonstrates the feasibility of using this ex vivo model for analysis of the ISG15 and autophagy pathways (presence/absence of putative ISG15 pathway inhibitors). There are three major advantages of using this ex-vivo model: a) it will reduce the number of experimental animals; b) it will generate quick information on whether genotoxic stress indeed induces neurodegeneration in A-T mice; and c) it will establish organotypic A-T brain slices as an ex vivo model to test the efficacy of potential drugs (e.g. small molecule inhibitors targeting the ISG15 pathway) in preventing A-T neurodegeneration.

Culturing of the organotypic brain slices: Organotypic brain slices will be prepared and maintained in culture. In brief, A-T and wild type mice (one-four weeks old) will be anesthetized and decapitated. The brain tissue will be removed and dissected in Hanks' balanced salt solution-based medium. Brain slices (400 µm thick) will be obtained using a McIlwain tissue chopper (The Mickle Lab Eng. Co. Ltd). Slices will be placed on Millicell culture plate inserts (Millipore, MA) and incubated for 3 days in OptiMem-based medium at 37° C. in a humidified atmosphere of 5% $CO_2$ and 95% air. Inserts will then be transferred and maintained in neurobasal medium. Slices will be used for experiments after 4 to 7 days in culture. I have previously standardized this procedure in the lab.

Postmortem examination of A-T patients showed significant loss of Purkinje cells in the cerebellum. The alpha synuclein inclusions were also found in the substantia nigra of $Atm^{-/-}$ mice. In addition, the ISG15/ubiquitin/LC3 inclusions were found in the midbrain regions (containing substantia nigral tissues) obtained from A-T human patients. Ex vivo brain slices of cerebellum and midbrain regions of the A-T and wild type mice will be used to monitor "protein inclusions" and neurodegeneration in $Atm^{-/-}$ mice.

Assessing neurodegeneration. Brain Slices will be prepared for immunofluorescence analysis using MTT, anti-tyrosine hydroxylase (substantia nigra neurons), anti-calbindin (cerebellum neurons) (for survived neurons) and Fluoro Jade B (for degenerating neurons). In addition, propidium iodide uptake and lactate dehydrogenase efflux will be measured to assess neuronal cell death.

Assessing serum levels of ISG15: Serum levels of ISG15 in mice and human A-T patients will be assessed using ELISA assays.

Example 15

UV-Induces Bafilomycin-Resistant Degradation of Polyubiquitylated Proteins in Organotypic Cerebellar Brain Slices Grown in Culture Experiments were conducted to determine if UV would induce degradation of the ubiquitin-conjugated cellular proteins in A-T organotypic brain slices grown in culture, similar to the above findings for A-T cells (See FIGS. 8A-8B). Two-month-old mice were used irrespective of the gender. Cerebellar organotypic brain slices (400 µm thick)

from three mice were obtained using a McIlwain tissue chopper (The Mickle Lab Eng. Co. Ltd). Slices from two A-T mice and three ATM+/− mice were pooled and randomly placed on Millicell culture plate inserts (Millipore, Mass.). Brain slices were then incubated for 1 day in OptiMem-based medium at 37° C. in a humidified atmosphere of 5% CO2 and 95% air. One day later, slices were treated with Bafilomycin A1 for 18 hrs. Slices were then exposed to UV (150 mJ)) or left untreated. After three hours, tissue lysates were prepared as described above. Lysates were then analyzed by Western analysis using anti-ubiquitin antibody as described above, and the results shown in FIG. 17A. Intensity of the total polyubiquitylated proteins and free ubiquitin was quantitated using BioRad Quantity One software. All control values (−UV and +Bafl) were normalized to 100%, and values for experimental treatments were expressed as percent variations over control to give the results shown in FIG. 17B. In the bar graphs in FIG. 17B, the labels for both A-T and ATM+/− are the following: bar 1: No drug and +Bafl controls; bar 2:+UV; and bar 3: +Bafl +UV.

Figure 17A:
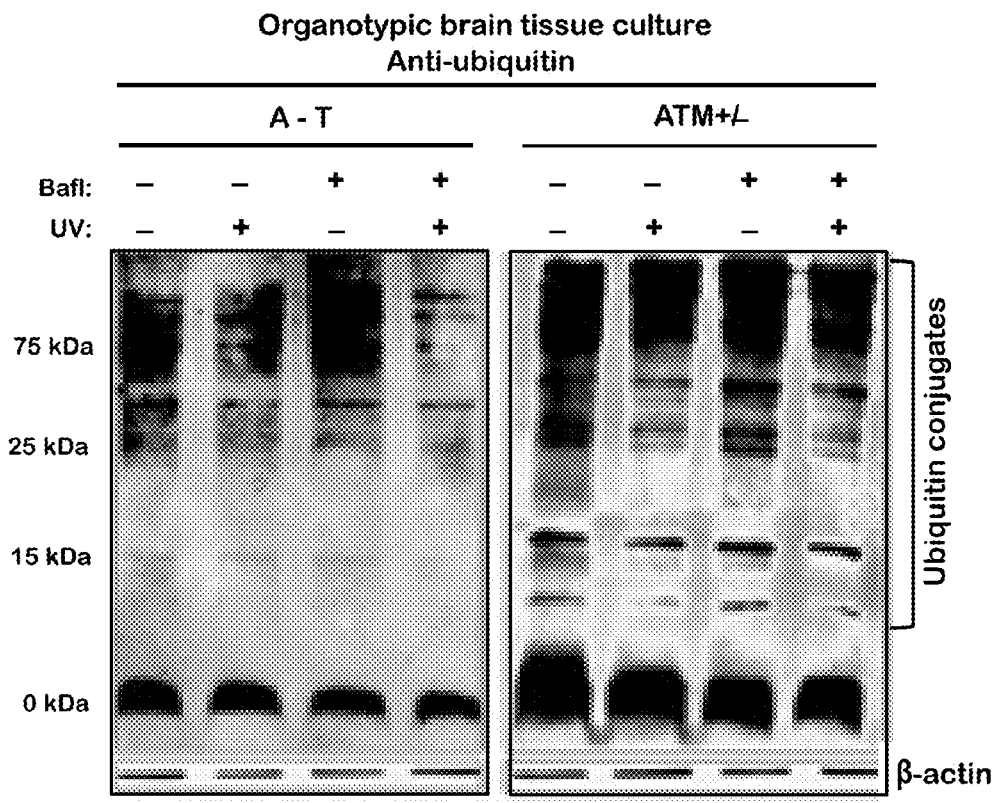
FIG. 17A-17B illustrate cerebellar organotypic brain slices from Atm knockout (A-T) and hetero (ATM+/−) mice incubated for 1 day in OptiMem-based medium at 37° C. in a humidified atmosphere of 5% CO2 and 95% air, then treated with Bafilomycin A1 for 18 hrs. Slices were then exposed to UV or left untreated. After three hours, tissue lysates were prepared and analyzed by Western analysis using anti-ubiquitin antibody (FIG. 17A). Intensity of the total polyubiquitylated proteins and free ubiquitin was quantitated using BioRad Quantity One software, and the results shown in FIG. 17B. All control values (−UV and +Bafl) are normalized to 100%, and values for experimental treatments were expressed as percent variations over control.
Figure 17B:
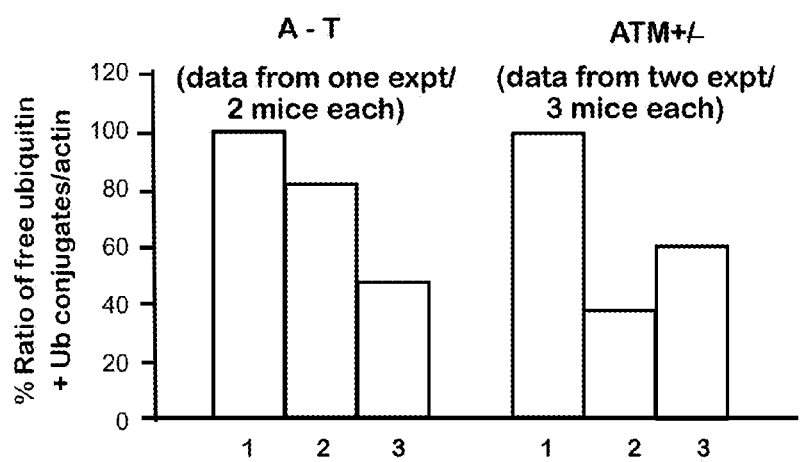

As shown in FIG. 17A (left panel), Bafilomycin failed to protect UV-mediated degradation of polyubiquitylated proteins in A-T brain slices. In contrast, similar to ATM+ cells, Bafilomycin markedly protected UV-induced degradation of polyubiquitylated proteins in ATM+/− brain slices (right panel). These results indicate that genotoxic stress induces bafilomycin-resistant aberrant autophagic flux (degradation) of polyubiquitylated proteins in the ubiquitin pathway ablated A-T cells, and in the cerebellar brain tissue. Above in FIGS. 8A and 8B is shown that ISG15 inhibits polyubiquitylation of cellular proteins in A-T cells. A similar decrease in the endogenous polyubiquitylated proteins is seen in A-T compared to ATM+/− mice brains (FIG. 17A, compare lane 1 of A-T and ATM+ panels). Hence, similar to A-T cells, polyubiquitylation is also defective in A-T mice brains. Polyubiquitylation is a prerequisite for degradation of cellular proteins via the proteasome. Because polyubiquitylation is defective, degradation of cellular proteins is impaired in A-T cells. ISG15-mediated proteinopathy leads to accumulation of neuronal proteins which in turn leads to neuronal cell death in A-T.

Example 16

UV Induces Massive Autophagy in A-T Cells and the Organotypic Mice Brain Slices.

Figure 18A:
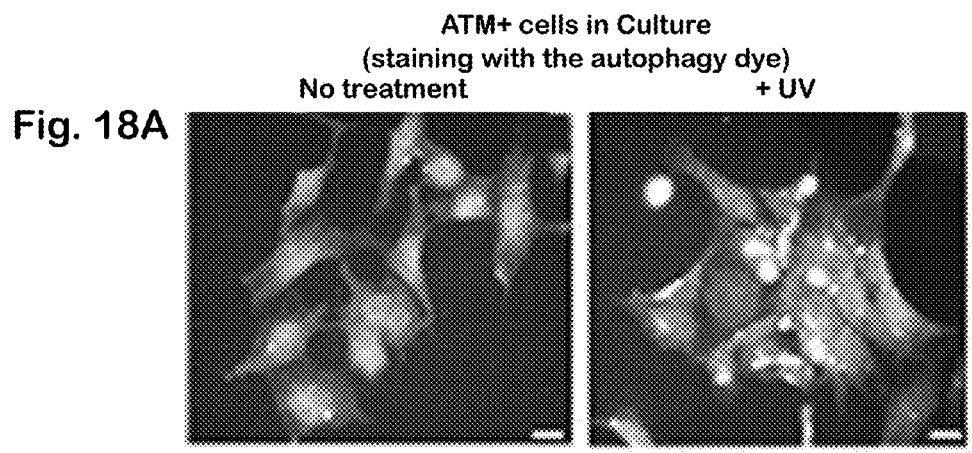
FIG. 18A illustrates ATM+ cells cultured on fibronectin-coated glass coverslips, and then exposed to UV radiation and allowed to recover for 3 hrs. Cells were then washed (2×1 min) with PBS and stained with Cyt-ID® (Cyt-ID® Autophagy Detection Kit from Enzo Lifesciences) for 30 min at 37° C. in a CO2 incubator. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations).

To determine whether UV induces autophagy in ATM+ cells and ATM+/− organotypic cerebellar brain slices grown in culture, the following experiment was conducted. ATM+ cells were cultured on fibronectin-coated glass coverslips. Cells were then exposed to UV radiation and allowed to recover for 3 hrs. Cells were then washed (2×1 min) with PBS and stained with Cyt-ID® (Cyt-ID® Autophagy Detection Kit from Enzo Lifesciences) for 30 min at 37° C. in a $CO_2$ incubator following manufacturer's protocol. Stained cells were then washed (2×1 min) with PBS and fixed with 4% paraformaldehyde for 20 min at room temperature. After washing with PBS (3×10 min), cells were mounted on slides in anti-fade mounting medium with DAPI (Invitrogen). Images were taken using a 63× oil immersion objective with a Leica DMRA2 upright microscope run through SlideBook software (Intelligent Imaging Innovations). The results are shown in FIG. 18A.

Figure 18B:
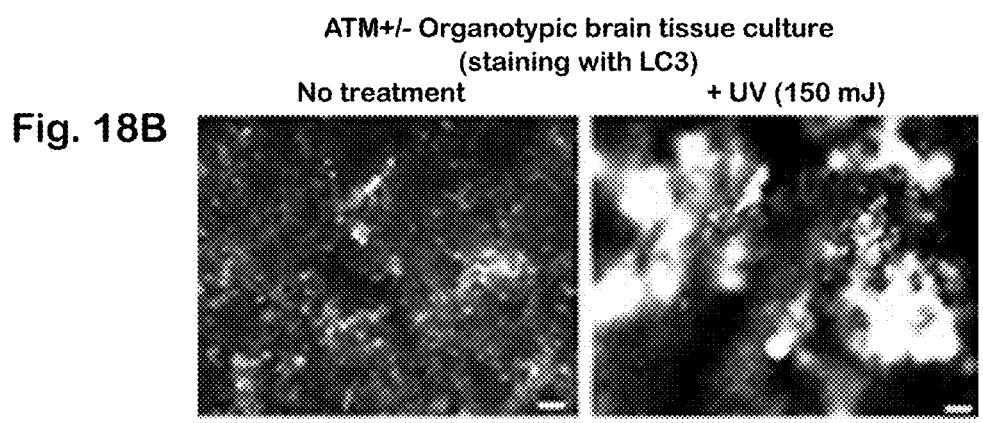
FIG. 18B illustrates murine organotypic cerebellar brain slices exposed to UV radiation and allowed to recover for 3 hrs. Slices were washed with PBS (2×5 min) and immunostained for LC3 (MBL International Corporation) for 1 h at room temperature. After washing with PBS (2×5 min), cells were incubated with Alexa-Fluor 488 goat anti-mouse IgG secondary antibody (1:100) (Invitrogen) for 1 hr. Brain slices were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations). The experiments have been repeated twice, and the results were reproducible.

In addition, UV induced autophagy in ATM+/− brain slices grown in culture. Using Immunofluorescence analysis, organotypic cerebellar brain slices were prepared as described above in Example 15. Slices were then exposed to UV radiation and allowed to recover for 3 hrs. Slices were washed with PBS (2×5 min) and immunostained for LC3 (MBL International Corporation) for 1 h at room temperature. After washing with PBS (2×5 min), cells were incubated with Alexa-Fluor 488 goat anti-mouse IgG secondary antibody (1:100) (Invitrogen) for 1 h. Brain slices were then washed with PBS and mounted on slides in anti-fade mounting medium with DAPI (Invitrogen). Images were taken using a 63× oil immersion objective with a Leica DMRA2 upright microscope run through SlideBook software (Intelligent Imaging Innovations). The experiments have been repeated twice, and the results were reproducible. Representative images are shown in FIG. 18B.

Figure 18C:
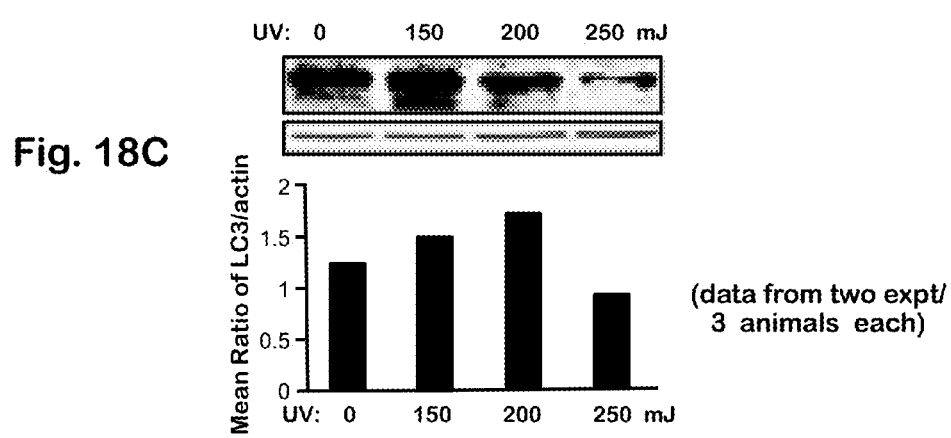
FIG. 18C illustrates murine organotypic brain slices exposed to different doses of UV and allowed to recover for 3 hrs. After three hours, tissue lysates were prepared and then analyzed by Western analysis using LC3 and actin-specific antibodies (FIG. 18C, top panel). Intensity of the total LC3 and corresponding actin bands was quantitated using BioRad Quantity One software, and the results shown in the bar graph (FIG. 18C, lower graph). The amounts of LC3 on the blots were calculated as a ratio between band intensities of LC3 (I and II) and actin (bar chart).

UV induces autophagy in ATM+/− brain slices grown in culture as shown in FIG. 18C. Using Western analysis, organotypic brain slices were prepared as described above. Slices were then exposed to different doses of UV and allowed to recover for 3 h. After 3 h, tissue lysates were prepared as described above. Lysates were then analyzed by Western analysis using LC3 and actin-specific antibodies as described above. Intensity of the total LC3 and corresponding actin bands was quantitated using BioRad Quantity One software. The amounts of LC3 on the blots were calculated as a ratio between band intensities of LC3 (I and II) and actin and the results shown in the bar chart. UV induced autophagy in ATM+ cells (FIG. 18A), and ATM+/− cerebellar brain slices (FIG. 18B-18C). Consistent with the immunofluorescence analysis (FIG. 18B), LC3 protein expression was also increased in ATM+/− brain tissue lysates in Western analysis (FIG. 18C). The effect of UV on autophagy in A-T brain slices grown in culture will also be assayed.

Example 17

UV-Induces Bafilomycin-Resistant Degradation of Autophagy Substrate LC3 in A-T Mice Brain Slices Grown in Culture.

Figure 19A:
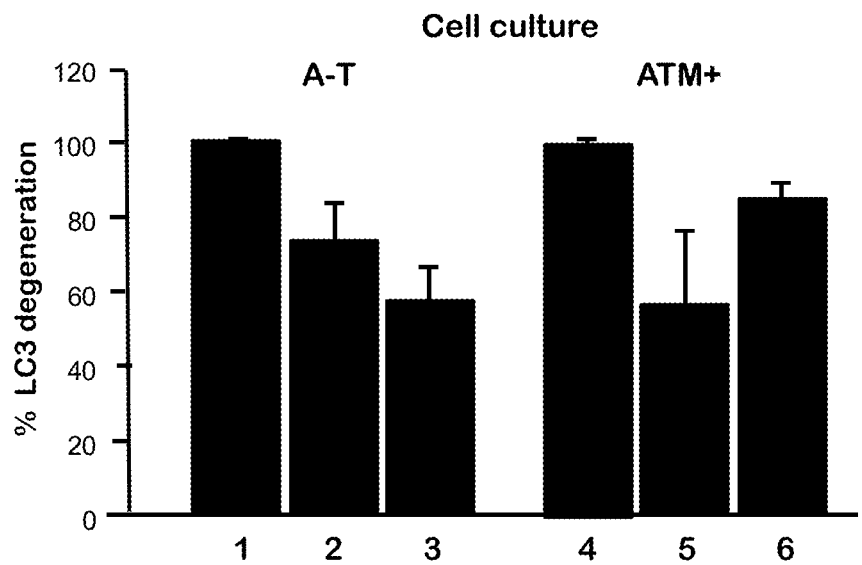
FIG. 19A illustrates A-T and ATM+ cells either left untreated or treated with the autophagy inhibitor Bafilomycin A1 for 18 h, and then exposed to UV radiation or left untreated. Cells were then allowed to recover in the presence of inhibitors for additional three hours. Cell lysis, SDS-PAGE, and immunoblotting analysis to detect LC3 was carried out. Intensities of the total LC3 bands were quantitated using BioRad Quantity One software, and the results shown in FIG. 19A. The bar graph shows average values (±SE) of % degradation of LC3 measured from three independent experiments.

UV induces aberrant degradation of autophagy substrate LC3 in A-T cells and brain slices. In FIG. 19A, LC3 degradation in UV-treated A-T cells is shown. A-T and ATM+ cells were either left untreated or treated with the autophagy inhibitor Bafilomycin A1 (1 nM) for 18 h. Cells were then exposed to UV radiation (25 mJ) or left untreated. Cells were then allowed to recover in the presence of inhibitors for additional 3 h. Cell lysis, SDS-PAGE, and immunoblotting analysis to detect LC3 were carried out as described above. Intensities of the total LC3 bands were quantitated using BioRad Quantity One software. The bar graph in FIG. 19A shows average values (±SE) of % degradation of LC3 measured from three independent experiments.

Figure 19B:
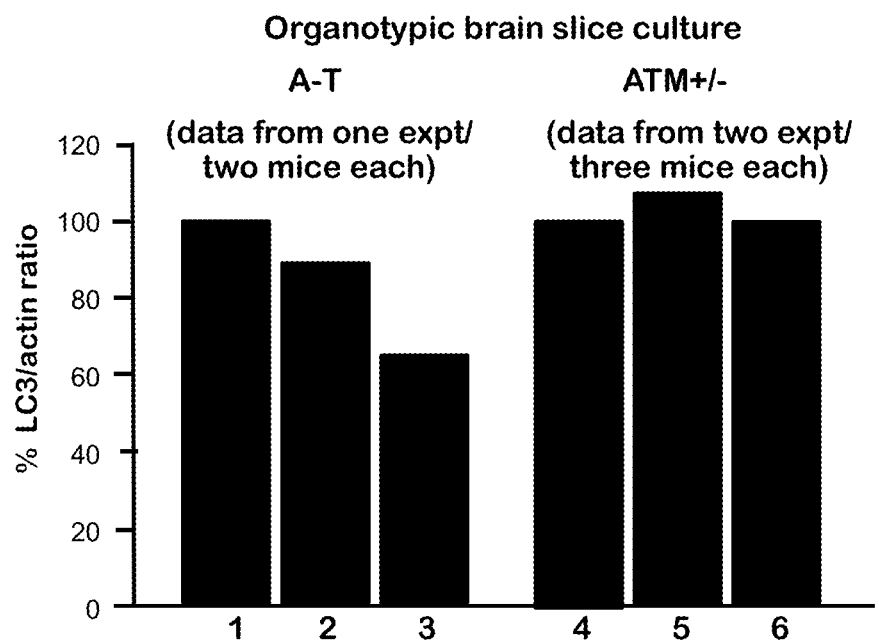
FIG. 19B illustrates tissue lysates prepared from A-T and ATM+/− brains described for FIG. 17A that were analyzed for LC3 and actin proteins. Intensity of the total LC3 and corresponding actin bands was quantitated using BioRad Quantity One software, and the results shown in FIG. 19B. The percent changes in LC3 amounts were calculated as a ratio between band intensities of LC3 (I and II) and actin (bar chart).

In FIG. 19B, LC3 degradation in UV-treated A-T brain slices is shown. The same tissue lysates prepared from A-T and ATM+/− brains used in FIG. 17A were analyzed for LC3 and actin proteins. Intensity of the total LC3 and corresponding actin bands was quantitated using BioRad Quantity One software. The percent changes in LC3 amounts were calculated as a ratio between band intensities of LC3 (I and II) and actin (bar chart). In FIGS. 19A and 19B, the bar graphs have the following legends: bars 1: No drug and +Bafl controls; bars 2:+UV; and bars 3: +Bafl +UV.

Result shown in FIGS. 19A and 19B indicate that similar to A-T cells (FIG. 19A, compare lanes 1 and 2) genotoxic stress induces bafilomycin-resistant aberrant autophagic flux (degradation) of autophagy substrates in A-T cerebellar brain slices (FIG. 19B, compare lanes 1 and 3) grown in culture. In contrast, Bafilomycin protected UV-induced autophagic flux in both ATM+ cells (FIG. 19A, compare lanes 4 and 6) and ATM+/− cerebellar slices (FIG. 19B, compare lanes 4 and 6).

Example 18

Elevated ISG15 Expression Causes Defective Mitophagy

Mitochondrial dysfunction due to oxidative stress is associated with various neurological disorders such as Parkinson's, Alzheimer's (76-78), and also implicated in A-T neurodegeneration (51, 79). Defective mitophagy, a selective form of autophagy that degrades abnormal mitochondria, was shown responsible for mitochondrial dysfunction in A-T (51, 79). Other mitochondrial abnormalities seen in A-T cells were elevated reactive oxygen species, increased aberrant mitochondria, high cellular respiratory capacity, and decreased mitophagy (51). As shown above, I have demonstrated that autophagy is activated, and autophagy is deregulated in response to genotoxic stress in A-T cells. In addition, as shown above, autophagy was restored in ISG15-silenced A-T cells.

Figure 20:
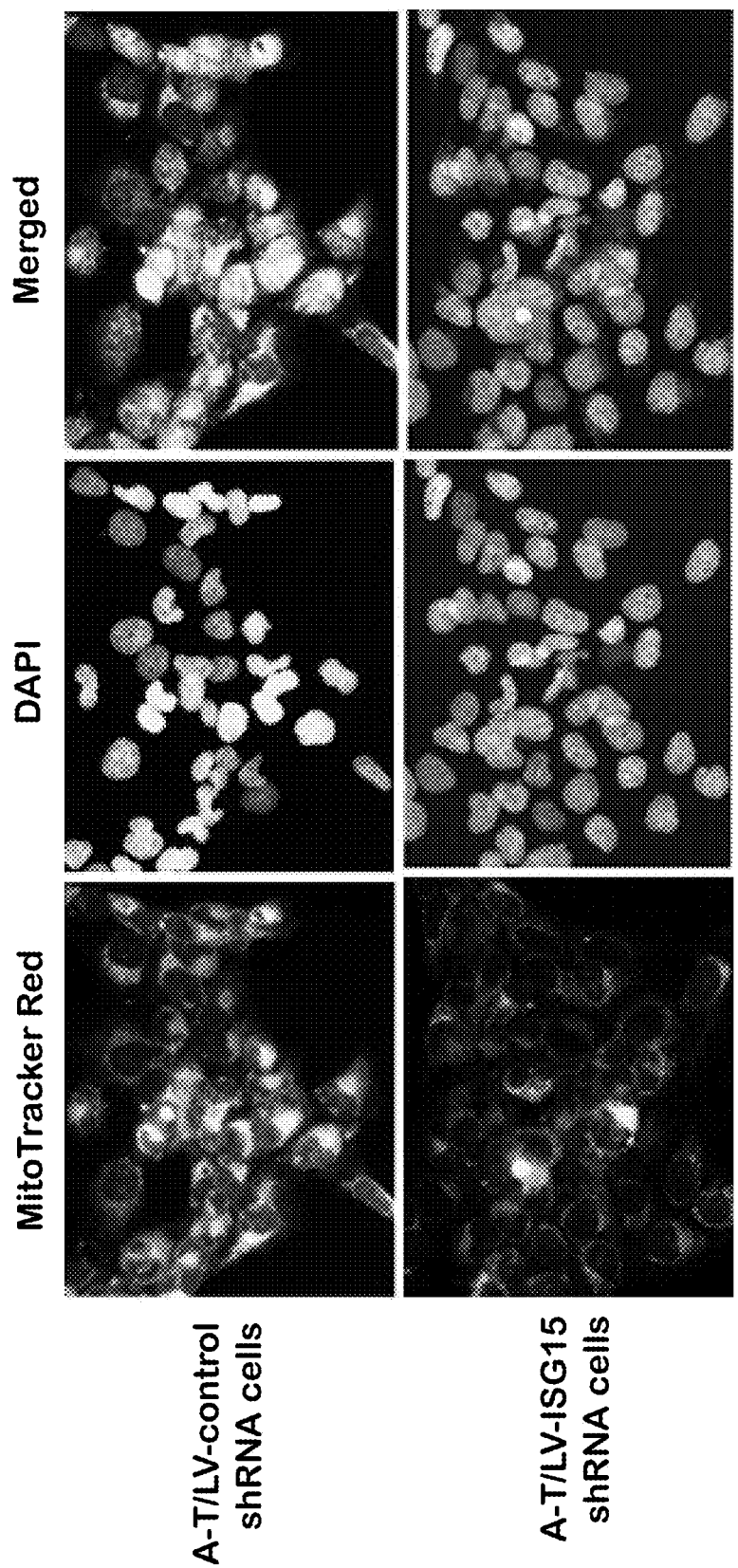
FIG. 20 illustrates representative fluorescence images of A-T/LV-control shRNA cells (upper panels) and A-T/LV- ISG15 shRNA cells (lower panels) co-stained with MitoTracker Red® dye and DAPI.

Representative fluorescence images of A-T/LV-control shRNA (upper panels) and A-T/LV-ISG15 shRNA (lower panels) cells co-stained with MitoTracker Red® dye and DAPI are shown (Scale bar: 10 μM) in FIG. 20. These cells were prepared as discussed above in Example 7. Using MitoTracker Red® dye, mitochondrial mass was shown to increase in A-T cells (see FIG. 20, top panels). However, mitochondrial mass was markedly decreased in ISG15-silenced A-T cells (FIG. 20, lower panels). Together our studies have revealed that defective mitophagy and macroautophagy in A-T cells is in part is caused by the elevated expression of ISG15.

In addition to ISG15 levels and macroautophagy markers, mitochondrial markers such as complex-I, decreased mitochondrial membrane potential, increased levels of mitochondrial superoxide, and mitochondrial mass, can be used to detect ISG15-mediated proteinopathies in blood mononuclear cells (or other cells) obtained from A-T patients. The example above shows the increased levels of mitochondrial mass in A-T cells. Future experiments will demonstrate that complex-I, mitochondrial membrane potential, and mitochondrial superoxide that change in A-T cells are also caused in part by increased ISG15 expression. These markers can also be used to diagnose a patient with ataxia telangiectasia prone to neurodegeneration.

REFERENCES

1. Frappart, P. O., and McKinnon, P. J. (2006) Ataxia-telangiectasia and related diseases. Neuromolecular Med. 8, 495-511
2. Lavin, M. F., and Khanna, K. K. (1999) ATM: the protein encoded by the gene mutated in the radiosensitive syndrome ataxia-telangiectasia. Int. J. Radiat. Biol. 75, 1201-1214
3. Boder, E. (1985) Ataxia-telangiectasia: an overview. Kroc Found. Ser. 19, 1-63
4. Chun, H. H., and Gatti, R. A. (2004) Ataxia-telangiectasia, an evolving phenotype. DNA Repair (Amst) 3, 1187-1196
5. Easton, D. F. (1994) Cancer risks in A-T heterozygotes. Int. J. Radiat. Biol. 66, S177-182
6. Sun, X., Becker-Catania, S. G., Chun, H. H., Hwang, M. J., Huo, Y., Wang, Z., Mitui, M., Sanal, O., Chessa, L., Crandall, B., and Gatti, R. A. (2002) Early diagnosis of ataxia-telangiectasia using radiosensitivity testing. J. Pediatr. 140, 724-731
7. Taylor, A. M., Hamden, D. G., Arlett, C. F., Harcourt, S. A., Lehmann, A. R., Stevens, S., and Bridges, B. A. (1975) Ataxia telangiectasia: a human mutation with abnormal radiation sensitivity. Nature, 258, 427-429
8. Lavin, M. F., Scott, S., Gueven, N., Kozlov, S., Peng, C., and Chen, P. (2004) Functional consequences of sequence alterations in the ATM gene. DNA Repair (Amst), 3, 1197-1205
9. Savitsky, K., Bar-Shira, A., Gilad, S., Rotman, G., Ziv, Y., Vanagaite, L., Tagle, D. A., Smith, S., Uziel, T., Sfez, S., Ashkenazi, M., Pecker, I., Frydman, M., Hamik, R., Patanjali, S. R., Simmons, A., Clines, G. A., Sartiel, A., Gatti, R. A., Chessa, L., Sanal, O., Lavin, M. F., Jaspers, N. G., Taylor, A. M., Arlett, C. F., Miki, T., Weissman, S. M., Lovett, M., Collins, F. S., and Shiloh, Y. (1995) A single ataxia telangiectasia gene with a product similar to PI-3 kinase. Science 268, 1749-1753
10. Matsuoka, S., Ballif, B. A., Smogorzewska, A., McDonald, E. R., 3rd, Hurov, K. E., Luo, J., Bakalarski, C. E., Zhao, Z., Solimini, N., Lerenthal, Y., Shiloh, Y., Gygi, S. P., and Elledge, S. J. (2007) ATM and ATR substrate analysis reveals extensive protein networks responsive to DNA damage. Science 316, 1160-1166
11. Shiloh, Y. and Rotman, G. (1996) Ataxia-telangiectasia and the ATM gene. linking neurodegeneration, immunodeficiency, and cancer to cell cycle checkpoints. J. Clin. Immunol. 16, 254-260
12. Katyal, S. and McKinnon, P. J. (2008) DNA strand breaks, neurodegeneration and aging in the brain. Mech. Ageing Dev. 129, 483-491
13. Biton, S., Barzilai, A., and Shiloh, Y. (2008) The neurological phenotype of ataxia-telangiectasia: solving a persistent puzzle. DNA Repair (Amst), 7, 1028-1038
14. Rolig, R. L., and McKinnon, P. J. (2000) Linking DNA damage and neurodegeneration. Trends Neurosci. 23, 417-424
15. Ross, C. A., and Pickart, C. M. (2004) The ubiquitin-proteasome pathway in Parkinson's disease and other neurodegenerative diseases. Trends Cell Biol. 14, 703-711
16. Schmitt, H. P. (2006) Protein ubiquitination, degradation and the proteasome in neurodegenerative disorders: no clear evidence for a significant pathogenetic role of proteasome failure in Alzheimer disease and related disorders. Med. Hypotheses 67, 311-317
17. Ciechanover, A. (2005) Early work on the ubiquitin proteasome system, an interview with Aaron Ciechanover. Interview by CDD. Cell Death Differ, 12, 1167-1177.
18. Eilam, R., Peter, Y., Groner, Y., and Segal, M. (2003) Late degeneration of nigro-striatal neurons in ATM−/− mice. Neuroscience 121, 83-98
19. Agamanolis, D. P., and Greenstein, J. I. (1979) Ataxia-telangiectasia. Report of a case with Lewy bodies and vascular abnormalities within cerebral tissue. J. Neuropathol. Exp. Neurol. 38, 475-489
20. Wood, L. M., Sankar, S., Reed, R. E., Haas, A. L., Liu, L. F., McKinnon, P., and Desai, S. D. (2011) A Novel Role for ATM in Regulating Proteasome-Mediated Protein Degradation through Suppression of the ISG15 Conjugation Pathway. PLoS One 6, e16422
21. Narasimhan, J., Potter, J. L., and Haas, A. L. (1996) Conjugation of the 15-kDa interferon-induced ubiquitin homolog is distinct from that of ubiquitin. J. Biol. Chem. 271, 324-330

22. Zhang, D., and Zhang, D. E. (2011) Interferon-stimulated gene 15 and the protein ISGylation system. J Interferon Cytokine Res. 31, 119-130.
23. Haas, A. L., Ahrens, P., Bright, P. M., and Ankel, H. (1987) Interferon induces a 15-kilodalton protein exhibiting marked homology to ubiquitin. J. Biol. Chem. 262, 11315-11323
24. Desai, S. D., Haas, A. L., Wood, L. M., Tsai, Y. C., Pestka, S., Rubin, E. H., Saleem, A., Nur, E. K. A., and Liu, L. F. (2006) Elevated expression of ISG15 in tumor cells interferes with the ubiquitin/26S proteasome pathway. Cancer Res. 66, 921-928
25. Lu, G., Reinert, J. T., Pitha-Rowe, I., Okumura, A., Kellum, M., Knobeloch, K. P., Hassel, B., and Pitha, P. M. (2006) ISG15 enhances the innate antiviral response by inhibition of IRF-3 degradation. Cell Mol. Biol. (Noisy-le-grand), 52, 29-41
26. Okumura, A., Pitha, P. M., and Harty, R. N. (2008) ISG15 inhibits Ebola VP40 VLP budding in an L-domain-dependent manner by blocking Nedd4 ligase activity. Proc. Natl. Acad. Sci. USA 105, 3974-3979
27. Malakhova, O. A., and Zhang, D. E. (2008) ISG15 inhibits Nedd4 ubiquitin E3 activity and enhances the innate antiviral response. J. Biol. Chem. 283, 8783-8787
28. Takeuchi, T., and Yokosawa, H. (2005) ISG15 modification of Ubc13 suppresses its ubiquitin-conjugating activity. Biochem. Biophys. Res. Commun. 336, 9-13
29. Zou, W., Papov, V., Malakhova, O., Kim, K. I., Dao, C., Li, J., and Zhang, D. E. (2005) ISG15 modification of ubiquitin E2 Ubc13 disrupts its ability to form thioester bond with ubiquitin. Biochem. Biophys. Res. Commun. 336, 61-68
30. Zou, W., Wang, J., and Zhang, D. E. (2007) Negative regulation of ISG15 E3 ligase EFP through its autoISGylation. Biochem. Biophys. Res. Commun. 354, 321-327
31. Pandey, U. B., Batlevi, Y., Baehrecke, E. H., and Taylor, J. P. (2007) HDAC6 at the intersection of autophagy, the ubiquitin-proteasome system and neurodegeneration. Autophagy 3, 643-645
32. Pandey, U. B., Nie, Z., Batlevi, Y., McCray, B. A., Ritson, G. P., Nedelsky, N. B., Schwartz, S. L., DiProspero, N. A., Knight, M. A., Schuldiner, O., Padmanabhan, R., Hild, M., Berry, D. L., Garza, D., Hubbert, C. C., Yao, T. P., Baehrecke, E. H., and Taylor, J. P. (2007) HDAC6 rescues neurodegeneration and provides an essential link between autophagy and the UPS. Nature 447, 859-863
33. Nedelsky, N. B., Todd, P. K., and Taylor, J. P. (2008) Autophagy and the ubiquitin-proteasome system: collaborators in neuroprotection. Biochim. Biophys. Acta. 1782, 691-699
34. Rubinsztein, D. C. (2007) Autophagy induction rescues toxicity mediated by proteasome inhibition. Neuron 54, 854-856
35. Mizushima, N. (2007) Autophagy: process and function. Genes Dev. 21, 2861-2873
36. Klionsky, D. J., and Emr, S. D. (2000) Autophagy as a regulated pathway of cellular degradation. Science 290, 1717-1721
37. Desai, S. D., Wood, L. M., Tsai, Y. C., Hsieh, T. S., Marks, J. R., Scott, G. L., Giovanella, B. C., and Liu, L. F. (2008) ISG15 as a novel tumor biomarker for drug sensitivity. Mol. Cancer Ther. 7, 1430-1439
38. Liu, L. F. (1989) DNA topoisomerase poisons as antitumor drugs. Annu Rev. Biochem. 58, 351-375
39. Wu, X., Rathbun, G., Lane, W. S., Weaver, D. T., and Livingston, D. M. (2000) Interactions of the Nijmegen breakage syndrome protein with ATM and BRCA1. Cold Spring Harb. Symp. Quant. Biol. 65, 535-545
40. Desai, S. D., Reed, R. E., Burks, J., Wood, L. M., Pullikuth, A. K., Haas, A. L., Liu, L. F., Breslin, J. W., Meiners, S., and Sankar, S. (2012) ISG15 disrupts cytoskeletal architecture and promotes motility in human breast cancer cells. Exp. Biol. Med. (Maywood), 237, 38-49.
41. Pear, W. S., Nolan, G. P., Scott, M. L., and Baltimore, D. (1993) Production of high-titer helper-free retroviruses by transient transfection. Proc. Natl. Acad. Sci. USA, 90, 8392-8396
42. Thomson, T. M., and Guerra-Rebollo, M. (2010) Ubiquitin and SUMO signaling in DNA repair. Biochem. Soc. Trans. 38, 116-131
43. Lavin, M. F., Birrell, G., Chen, P., Kozlov, S., Scott, S., and Gueven, N. (2005) ATM signaling and genomic stability in response to DNA damage. Mutat. Res. 569, 123-132
44. Loeb, K. R., and Haas, A. L. (1992) The interferon-inducible 15-kDa ubiquitin homolog conjugates to intracellular proteins. J. Biol. Chem. 267, 7806-7813
45. Wu, W. K., Wu, Y. C., Yu, L., Li, Z. J., Sung, J. J., and Cho, C. H. (2008) Induction of autophagy by proteasome inhibitor is associated with proliferative arrest in colon cancer cells. Biochem. Biophys. Res. Commun. 374, 258-263
46. Ge, P. F., Zhang, J. Z., Wang, X. F., Meng, F. K., Li, W. C., Luan, Y. X., Ling, F., and Luo, Y. N. (2009) Inhibition of autophagy induced by proteasome inhibition increases cell death in human SHG-44 glioma cells. Acta Pharmacol. Sin. 30, 1046-1052
47. Yamamoto, A., Tagawa, Y., Yoshimori, T., Moriyama, Y., Masaki, R., and Tashiro, Y. (1998) Bafilomycin A1 prevents maturation of autophagic vacuoles by inhibiting fusion between autophagosomes and lysosomes in rat hepatoma cell line, H-4-II-E cells. Cell Struct. Funct. 23, 33-42
48. Desai, S. D., Li, T. K., Rodriguez-Bauman, A., Rubin, E. H., and Liu, L. F. (2001) Ubiquitin/26S proteasome-mediated degradation of topoisomerase I as a resistance mechanism to camptothecin in tumor cells. Cancer Res. 61, 5926-5932
49. Desai, S. D., Liu, L. F., Vazquez-Abad, D., and D'Arpa, P. (1997) Ubiquitin-dependent destruction of topoisomerase I is stimulated by the antitumor drug camptothecin. J. Biol. Chem. 272, 24159-24164
50. Desai, S. D., Zhang, H., Rodriguez-Bauman, A., Yang, J. M., Wu, X., Gounder, M. K., Rubin, E. H., and Liu, L. F. (2003) Transcription-dependent degradation of topoisomerase I-DNA covalent complexes. Mol. Cell Biol. 23, 2341-2350
51. Valentin-Vega, Y. A., Maclean, K. H., Tait-Mulder, J., Milasta, S., Steeves, M., Dorsey, F. C., Cleveland, J. L., Green, D. R., and Kastan, M. B. (2012) Mitochondrial dysfunction in ataxia-telangiectasia. Blood, 119: 1490-1500.
52. Tanida, I., Ueno, T., and Kominami, E. (2004) LC3 conjugation system in mammalian autophagy. Int. J. Biochem. Cell Biol. 36, 2503-2518
53. Kabeya, Y., Mizushima, N., Ueno, T., Yamamoto, A., Kirisako, T., Noda, T., Kominami, E., Ohsumi, Y., and Yoshimori, T. (2000) LC3, a mammalian homologue of yeast Apg8p, is localized in autophagosome membranes after processing. EMBO J. 19, 5720-5728

54. Klionsky, D. J., et al. (2008) Guidelines for the use and interpretation of assays for monitoring autophagy in higher eukaryotes. Autophagy 4, 151-175
55. Komatsu, M., and Ichimura, Y. (2010) Physiological significance of selective degradation of p62 by autophagy. FEBS Lett. 584, 1374-1378
56. Seglen, P. O., and Gordon, P. B. (1982) 3-Methyladenine: specific inhibitor of autophagic/lysosomal protein degradation in isolated rat hepatocytes. Proc. Natl. Acad. Sci. USA, 79, 1889-1892
57. Maragakis, N. J., and Rothstein, J. D. (2006) Mechanisms of Disease: astrocytes in neurodegenerative disease. Nat. Clin. Pract. Neurol. 2, 679-689
58. Wang, R., Yang, B., and Zhang, D. (2011) Activation of interferon signaling pathways in spinal cord astrocytes from an ALS mouse model. Glia 59, 946-958
59. Figueiredo-Pereira, M. E., and Cohen, G. (199) The ubiquitin/proteasome pathway: friend or foe in zinc-, cadmium-, and H2O2-induced neuronal oxidative stress. Mol. Biol. Rep. 26, 65-69
60. Barlow, C., Ribaut-Barassin, C., Zwingman, T. A., Pope, A. J., Brown, K. D., Owens, J. W., Larson, D., Harrington, E. A., Haeberle, A. M., Mariani, J., Eckhaus, M., Herrup, K., Bailly, Y., and Wynshaw-Boris, A. (2000) ATM is a cytoplasmic protein in mouse brain required to prevent lysosomal accumulation. Proc. Natl. Acad. Sci. USA, 97, 871-876
61. Bregman, D. B., Halaban, R., van Gool, A. J., Henning, K. A., Friedberg, E. C., and Warren, S. L. (1996) UV-induced ubiquitination of RNA polymerase II: a novel modification deficient in Cockayne syndrome cells. Proc. Natl. Acad. Sci. USA 93, 11586-11590
62. Sharma, A., Kaur, M., Kar, A., Ranade, S. M., and Saxena, S. (2010) Ultraviolet radiation stress triggers the down-regulation of essential replication factor Mcm10. J. Biol. Chem. 285, 8352-8362
63. Metcalf, D. J., Garcia-Arencibia, M., Hochfeld, W. E., and Rubinsztein, D. C. (2012) Autophagy and misfolded proteins in neurodegeneration. Exp Neurol. 238, 22-28
64. Lehman, N. L. (2009) The ubiquitin proteasome system in neuropathology. Acta Neuropathol. 118, 329-347
65. Cherra, S. J. and Chu, C. T. (2008) Autophagy in neuroprotection and neurodegeneration: A question of balance. Future Neurol. 3, 309-323
66. Chu, C. T. (2006) Autophagic stress in neuronal injury and disease. J. Neuropathol. Exp. Neurol. 65, 423-432.
67. Okumura A, Lu G, Pitha-Rowe I, Pitha P M (2006) Innate antiviral response targets HIV-1 release by the induction of ubiquitin-like protein ISG15. Proc Natl Acad Sci USA 103: 1440-1445.
68. Lu G, Reinert J T, Pitha-Rowe I, Okumura A, Kellum M, et al. (2006) ISG15 enhances the innate antiviral response by inhibition of IRF-3 degradation. Cell Mol Biol (Noisy-le-grand) 52: 29-41.
69. Takeuchi T, Iwahara S, Saeki Y, Sasajima H, Yokosawa H (2005) Link between the Ubiquitin Conjugation System and the ISG15 Conjugation System: ISG15 Conjugation to the UbcH6 Ubiquitin E2 Enzyme. J Biochem (Tokyo) 138: 711-719.
70. Siddoo-Atwal C, Haas A L, Rosin M P (1996) Elevation of interferon beta-inducible proteins in ataxia telangiectasia cells. Cancer Res. 56: 443-447.
71. Wu X, Ranganathan V, Weisman D S, Heine W F, Ciccone D N, et al. (2000) ATM phosphorylation of Nijmegen breakage syndrome protein is required in a DNA damage response. Nature 405: 477-482.
72. Herzog K H, Chong M J, Kapsetaki M, Morgan J I, McKinnon P J (1998) Requirement for Atm in ionizing radiation-induced cell death in the developing central nervous system. Science 280: 1089-1091.
73. Sakaguchi A, Kikuchi A (2004) Functional compatibility between isoform alpha and beta of type II DNA topoisomerase. J Cell Sci 117: 1047-1054.
74. Ikeda F, Dikic I (2008) Atypical ubiquitin chains: new molecular signals. 'Protein Modifications: Beyond the Usual Suspects' review series. EMBO Rep 9: 536-542.
75. Menendez-Benito V, Verhoef L G, Masucci M G, Dantuma N P (2005) Endoplasmic reticulum stress compromises the ubiquitin-proteasome system. Hum Mol Genet 14: 2787-2799.
76. Browne, S. E. and Beal, M. F. Oxidative damage and mitochondrial dysfunction in neurodegenerative diseases. Biochem Soc Trans, 22: 1002-1006, 1994.
77. Lin, M. T. and Beal, M. F. Mitochondrial dysfunction and oxidative stress in neurodegenerative diseases. Nature, 443: 787-795, 2006.
78. Johri, A. and Beal, M. F. Mitochondrial dysfunction in neurodegenerative diseases. J Pharmacol Exp Ther, 342: 619-630.
79. Ambrose, M., Goldstine, J. V., and Gatti, R. A. Intrinsic mitochondrial dysfunction in ATM-deficient lymphoblastoid cells. Hum Mol Genet, 16: 2154-2164, 2007.

The complete disclosures of all references cited in this specification are hereby incorporated by reference. Also incorporated by reference are the complete disclosures of the following: (1) L. M. Wood et al., "A novel role for ATM in regulating proteasome-mediated protein degradation through suppression of the ISG15 conjugation pathway," PLoS ONE, vol. 6(1): e16422, published Jan. 26, 2011; (2) S. D. Desai and R. E. Reed, "Rethinking neurodegeneration in Ataxia Telangiectasia: Role of proteinopathy," an abstract submitted for the 14th International Workshop on Ataxia-Telangiectasia and ATM, to be held in Delhi, India, Feb. 7-11, 2012; (3) S. D. Desai et al., "ISG15 disrupts cytoskeletal architecture and promotes motility to human breast cancer cells," Exp. Biol. Med. (Maywood), 237: 38-49 (2012); (4) S. D. Desai, "Therapeutic and Diagnostic Method for Ataxia-Telangiectasia," Provisional Application Ser. No. 61/565,715, filed 1 Dec. 2011; and (5) S. D. Desai, "An Improvement to Targeting the ISG15 Pathway in Ataxia-Telangiectasia: A Novel Therapeutic Approach for Treating A-T," U.S. Provisional Application Ser. No. 61/706,863, filed 28 Sep. 2012. In the event of an otherwise irreconcilable conflict, however, the present specification shall control.

What is claimed:

1. A method to decrease neurodegeneration in a patient with Ataxia telangiectasia, said method comprising administering to the patient an effective amount of an agent that inhibits the expression of a protein selected from the group consisting of ISG15 and UbcH8 (E2-ISG15).

2. The method of claim 1, wherein the agent is selected from the group consisting of shRNA and siRNA molecules that are targeted to the nucleic acid molecule encoding ISG15 as in GENBANK Accession No. AY168648 (SEQ ID NO:1).

3. The method of claim 1, wherein the agent is an shRNA that targets the nucleotides numbered from 232-250 in the nucleic acid molecule encoding ISG15 as in GENBANK Accession No. AY168648 (SEQ ID NO:1).

4. The method of claim 1, wherein the agent is selected from the group consisting of shRNA and siRNA molecules that are targeted to the nucleic acid molecule encoding UbcH8 as in GENBANK Accession No. AF031141 (SEQ ID NO:2).

5. The method of claim 1, wherein the agent is an shRNA that targets the nucleotides numbered from 237-255 in the nucleic acid molecule encoding UbcH8 as in GENBANK Accession No. AF031141 (SEQ ID NO:2).

* * * * *